United States Patent [19]

Watanabe et al.

[11] Patent Number: 5,610,009

[45] Date of Patent: Mar. 11, 1997

[54] MAMMALIAN EXPRESSION SYSTEMS FOR HEPATITIS C VIRUS ENVELOPE GENES

[75] Inventors: Shinichi Watanabe, Northbrook; Julie Yamaguchi, Chicago; Suresh M. Desai, Libertyville; Sushil G. Devare, Northbrook, all of Ill.

[73] Assignee: Abbott Laboratories, Abbott Park, Ill.

[21] Appl. No.: 188,281

[22] Filed: Jan. 28, 1994

[51] Int. Cl.⁶ ............................... C12Q 1/70; C07K 16/08
[52] U.S. Cl. ........................ 435/5; 436/820; 530/388.3; 530/389.4
[58] Field of Search ........................ 435/5, 69.7, 69.3, 435/69.8; 436/820; 530/388.3, 389.4

[56] References Cited

U.S. PATENT DOCUMENTS

| | | | |
|---|---|---|---|
| 5,106,726 | 4/1992 | Wang | 435/5 |
| 5,350,671 | 9/1994 | Houghton et al. | 435/5 |

FOREIGN PATENT DOCUMENTS

| | | |
|---|---|---|
| 2098253 | 11/1993 | Canada. |
| 0318216 | 5/1989 | European Pat. Off.. |
| 0388232 | 9/1990 | European Pat. Off.. |
| 2212511 | 7/1989 | United Kingdom. |
| WO9208734 | 5/1992 | WIPO. |
| WO9304088 | 3/1993 | WIPO. |
| WO93/15193 | 8/1993 | WIPO. |
| WO9321303 | 10/1993 | WIPO. |

OTHER PUBLICATIONS

Matsuura et al., Expression of Processed Envelope Protein of Hepatitis C Virus in Mammalian and Insect Cells. Journal of Virology 66(3):1425–1431, 1992.

M. Haijikata et al., "Gene mapping of the putative structural region of the hepatitis C virus genome by in vitro processing analysis" *Proc. Natl. Acad. Sci. USA, Biochemistry* vol. 88 (Jul. 1991) pp. 5547–5551.

Malon Kit, et al., "Bovine herpesvirus–1 . . . , " *Vaccine*, 9:564–572 Aug. 1991.

Shelley B. Blam, et al., "Addition of growth hormone secretion . . . ", *Oncogene*, 3:129–136.

N. Kato, et al., "Molecular cloning of the human . . . ", *Natl Acad. of Science USA*, 87:9524–9528, (1990).

H. Okamoto, et al., "Nucleotide sequence of the . . . ", *Journal of General Virology*, 72:2697–2704.

A. Weidemann, et al., "Identification, Biogenesis . . . ", *Cell*, 57:115–126 (1989).

D. E. Lowery, et al., "Alzheimer's Amyloid . . . ", *The Journal of Biological Chemistry*, 266:19842–19850 (1991).

J. Li, et al., "Two French Genotypes . . . ", *Gene*, 105:167–172 (1991).

D. Kremsdorf, et al., "Partial nucleotide . . . ", *Journal of General Virology*, 72:2557–2561 (1991).

A. Takamizawa, et al., "Structure and Organization of the Hepatitis C Virus . . . ", *Journal of Virology*, 65:1105–1113 (1991).

Uhlen et al., "Gene Fusions for Purpose of Expression: An Introduction", *Methods In Enzymology*, 185:129–143 (1981).

H. Hada, et al., "Detection by Western Blotting of an Antibody to the Hepatitis C Virus E1 Envelope Protein in Sera of Patients with Chronic Liver Disease", Acta Med. Okayama, vol. 46, 1992.

T. Goeser, et al., "Analysis of Immune Response of Patients Against the HCV E1 and E2 . . . ", Eur. J. Clin. Invest., vol. 23 (Suppl. 1), 1993, p. A15, abstract No. 73.

Michael Houghton, et al., *Special Article,* vol. 14, No. 2, 1991, "Molecular Biology of the Hepatitis C Viruses: Implications for Diagnosis, Development and Control of Viral Disease".

Genevieve Inchauspe, et al., *Proc. Natl. Acad. Sci. USA*, vol. 88, pp. 10292–10296, Nov. 1991, Biochemistry, "Genomic structure of the human prototype strain H of hepatitis C virus: Comparison with American and Japanese isolates".

Q.–L. Choo, et al., *Proc. Natl. Acad. Sci. USA*, vol. 88, pp. 2451–2455, Mar. 1991, Biochemistry, "Genetic organization and diversity of the hepatitis C virus".

*Primary Examiner*—Christine M. Nucker
*Assistant Examiner*—Donna C. Wortman
*Attorney, Agent, or Firm*—Cheryl L. Becker; Priscilla E. Porembski

[57] ABSTRACT

Mammalian expression systems for the production of HCV E1-E2 fusion proteins. Such expression systems provide high yields of HCV proteins extracelluarly, and enable the development of diagnostic, vaccine and therapeutic reagents which contain glycosylated structural antigens and also allow for the isolation of the HCV etiological agent.

7 Claims, 8 Drawing Sheets

Leu-Leu-Arg-Ile-Pro-Gln-Ala-Ile-Leu-Asp-Met-Ile-Ala-
Gly-Ala-His-Trp-Gly-Val-Leu-Ala-Gly-ILe-Ala-Tyr-Phe-
Ser-Met-Val-Gly-Asn-Trp-Ala-Lys-Val-Leu-Val-Val-Leu-
Leu-Leu-Phe-Ala

FIG.8

MAMMALIAN EXPRESSION SYSTEMS FOR HEPATITIS C VIRUS ENVELOPE GENES

RELATED APPLICATION

This application is related to U.S. patent application Ser. No. 08/144,099, filed Oct. 28, 1993, abandoned, entitled "Mammalian Expression Systems for Hepatitis C Virus," which is a continuation of U.S. Ser. No. 07/830,024, abandoned, both of which enjoy common ownership and are incorporated herein by reference.

BACKGROUND OF THE INVENTION

This invention relates generally to mammalian expression systems, and more particularly, relates to mammalian expression systems capable of generating hepatitis C virus (HCV) envelope proteins and the use of these proteins. These HCV envelope proteins, designated as E1 and E2, are fused by removing a cleavage site different from the conventionally observed site. These proteins are expressed in culture medium as well as in mammalian cells.

Hepatitis is one of the most important diseases transmitted from a donor to a recipient by transfusion of blood or blood products, transplantation of organs, and hemodialysis. Viral hepatitis is now known to include a group of viral agents with distinctive viral genes and mode of replication, causing hepatitis with different degrees of severity of hepatic damage through different routes of transmission. Acute viral hepatitis is clinically diagnosed by well-defined patient symptoms including jaundice, hepatic tenderness and an elevated level of liver transaminases such as Aspartate Transaminase (AST) and Alanine Transaminase (ALT).

Non-A Non-B Hepatitis (NANBH) is a term first used in 1975 that described cases of post-transfusion hepatitis not caused by either hepatitis A virus or hepatitis B virus. Feinstone et al., *New Engl. J. Med.* 292:454–457 (1975). The diagnosis of NANBH was made primarily by means of exclusion on the basis of serological analysis for the presence of hepatitis A and hepatitis B. Currently, NANBH is responsible for about 90% of the cases of post-transfusion hepatitis. Hollinger et al. in N. R. Rose et al., eds., *Manual of Clinical Immunology*, American Society for Microbiology, Washington, D.C., 558–572 (1986).

The identification of a putative non-A non-B (NANB) agent, Hepatitis C Virus (HCV), has been made. Kuo et al., *Science* 244:359–361 (1989); Choo et al., *Science* 244:362–364 (1989). Cloning and sequencing of HCV, now recognized as the primary agent of parenterally transmitted NANBH, has fostered interest and studies in the epidemiology, pathogenesis, and natural history of this disease. Kuo et al., *Science* 244:362–364 (1989).

Sequences from HCV which encode antigens that react immunologically with antibodies present in a majority of the patients clinically diagnosed with NANBH have been identified. Based on the information available and on the molecular structure of HCV, the genetic makeup of the virus consists of single stranded linear RNA (positive strand) of approximately 9.5 kb, and of one continuous translational open reading frame (ORF) encoding a polyprotein precursor of approximately 3000 amino acids. This precursor protein undergoes cotranslational and posttranslational processing, including cleavage and glycosylation, to the final structural and non-structural proteins. Houghton et al., *Hepatology* 14: 381–388 (1991). Structural proteins are identified as core protein and highly glycosylated envelope proteins E1 of molecular weight 33,000 and E2 of molecular weight 72,000. Hijitaka et al., *Gene* 88: 5547–5551 (1991). Replication of HCV occurs early following HCV infection in chimpanzees and a long period of viremia may occur prior to the appearance of antibodies against HCV proteins. Shimizu et al., *Proc. Natl. Acad. Sci. USA* 87:3392–6444 (1990); Farci et al., *New Eng. J. Med.* 325: 98–104 (1991).

HCV infection also has been reported in the development of chronic hepatitis, cirrhosis and HCC. Genesca et al., *Semin Liver Dis* 11: 147–164 (1991). The lack of effective neutralizing humoral immune response to HCV may be related to virus persistence and disease progression. Farci et al., *Science* 258: 135–140 (1992).

The availability of laboratory tests for serological diagnosis of hepatitis C viral infection has contributed to clarifying the role of HCV in the etiology of hepatitis in patients who have received blood or blood products, or undergone transplantation and hemodialysis. The detection of HCV antibodies in donor samples eliminates 70 to 80% of NANBH infected blood from the blood supply system. However, while the antibodies apparently are readily detectable during the chronic state of the disease, only 60% of the samples from the acute NANBH stage are HCV antibody positive. H. Alter et al., *New Eng. J. Med.* 321:1994–1500 (1989).

Although assay reagents and methods are available to detect the presence of either HCV antibody and/or HCV RNA, some individuals seropositive for HCV antibody, as well as some individuals infected with the HCV virus, are not diagnosed with HCV by these available assay reagents and methods. For example, it is known that the prevalence of HCV infection is high in kidney transplant recipients; it is hypothesized that active HCV replication may occur in the absence of HCV antibody detectable with current kits. Lau et al., *Hepatology* 18: 1027–1031 (1993). Moreover, when potential blood donors having a high risk of HCV infection were originally tested with sensitive serological screening assays, 13 of 19 tested were detected by those methods (68%), compared to all 19 blood donors testing positive for HCV RNA by polymerase chain reaction (PCR). Sugitani et al., *The Lancet* 339: 1018–1019 (1992).

Thus, there is a need for the development of additional assay reagents and assay systems to identify acute infection and viremia which may be present, and not currently detectable by commercially-available screening assays. These reagents and assay systems are needed in order to help distinguish between those individuals with acute and persistent, on-going and/or chronic infection and those individuals whose HCV infections are likely to be resolved, and to define the prognostic course of NANB hepatitis infection in order to develop preventive and/or therapeutic strategies. Also, the expression systems that allow for secretion of these glycosylated antigens would be helpful to purify and manufacture diagnostic and therapeutic reagents.

SUMMARY OF THE INVENTION

This invention provides novel mammalian expression systems that are capable of generating high levels of expressed proteins of HCV. In particular, the invention provides the construction of fusion proteins comprising of amyloid precursor protein (APP) and HCV E1 and E2, which are useful for generating high levels of expression in mammalian cells. These constructs may contain deletions in HCV E1 and E2 genes which allow the production of secretable fusion protein of APP-HCV E1-E2. These unique expression systems allow for the production of high levels of HCV proteins, allowing to the proper processing, glycosylation and folding of the viral protein(s) in the system. In particular, the present invention provides the plasmids pHCV-176, pHCV-172, pHCV-351 and pHCV-425. A small deletion introduced in HCV E1 gene and fused to truncated HCV E2, produces uncleavable fusion protein in the disclosed mammalian expression system. APP-HCV E1-E2 fusion protein, expressed from pHCV-425 in the mammalian expression system of the invention, can be recovered extracellularly as well as intracellularly.

The present invention also provides a method for detecting HCV antigen or antibody in a test sample suspected of containing HCV antigen or antibody, wherein the improvement comprises contacting the test sample with a glycosylated HCV antigen produced in a mammalian expression system. Also provided is a method for detecting HCV antigen or antibody in a test sample suspected of containing HCV antigen or antibody, wherein the improvement comprises contacting the test sample with an antibody produced by using a glycosylated HCV antigen produced in a mammalian expression system. The antibody can be monoclonal or polyclonal.

The present invention further provides a test kit for detecting the presence of HCV antigen or HCV antibody in a test sample suspected of containing said HCV antigen or antibody, comprising a container containing a glycosylated HCV antigen produced in a mammalian expression system. The test kit also can include a container containing an antibody produced by using a glycosylated HCV antigen produced in a mammalian expression system. The antibody provided by the test kits can be monoclonal or polyclonal.

BRIEF DESCRIPTION OF THE DRAWINGS

FIG. 8 presents the HCV sequence SEQ. ID. NO. 22 essential for cleavage of HCV E1-E2 and for E1 epitope.

DETAILED DESCRIPTION OF THE INVENTION

Figure 1:
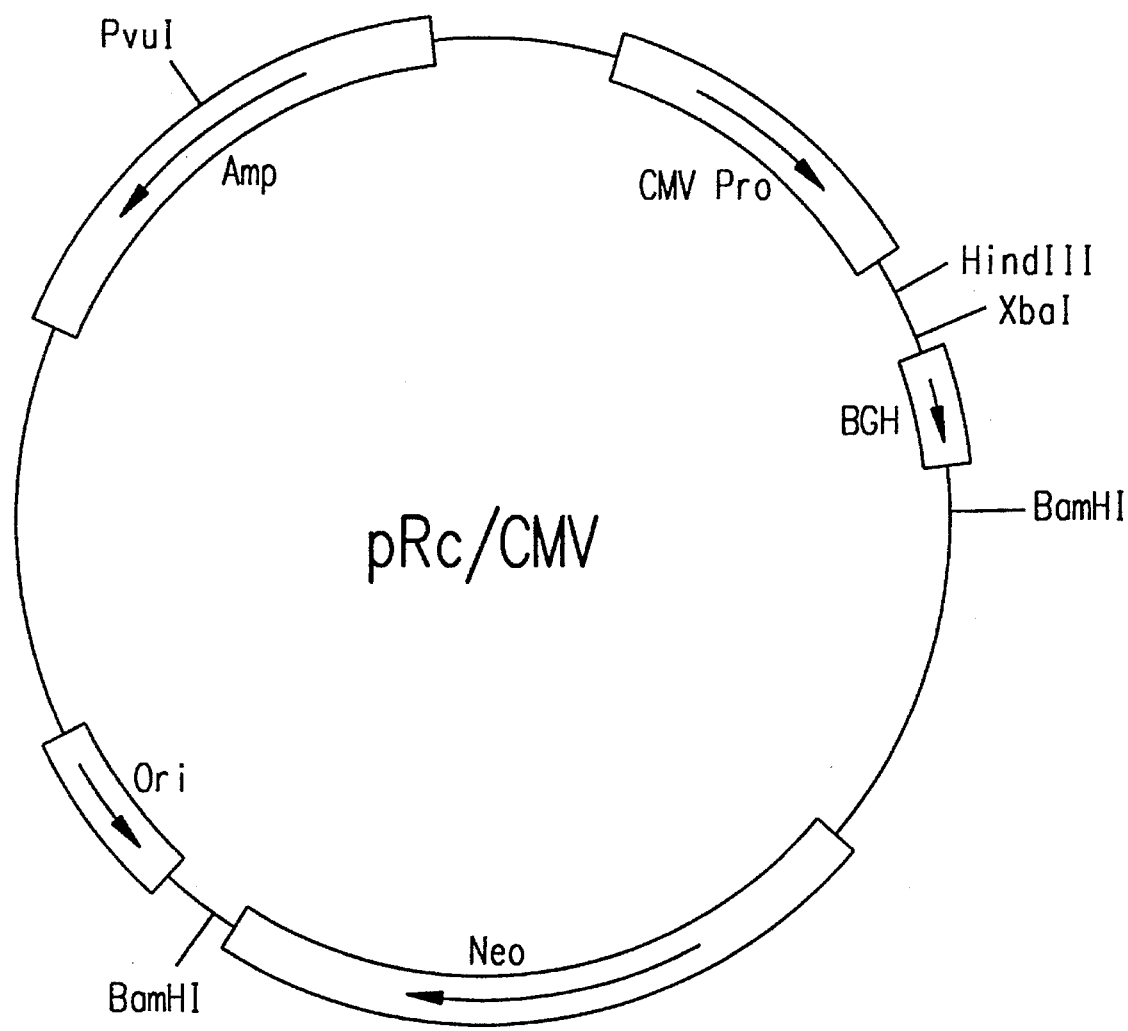
FIG. 1 presents a schematic representation of the mammalian expression vector pRc/CMV.

The present invention provides ways to produce glycosylated HCV E1 and E2 or E1-E2 fusion proteins expressed in mammalian expression systems. These glycosylated proteins have diagnostic utility in a variety of aspects, including, for example, assay systems for screening and prognostic applications. These HCV viral envelope proteins expressed in mammalian cells also allow for inhibitor studies including elucidation of specific viral attachment sites or sequences and/or viral receptors on susceptible cell types, for example, liver cells and the like.

The procurement of specific expression clones developed as described herein in mammalian expression systems provides antigens for diagnostic assays which can aid in determining the stage of HCV infection, such as, for example, acute versus on-going or persistent infections, and/or recent infection versus past exposure. These specific expression clones also provide prognostic markers for resolution of disease such as to distinguish resolution of disease from chronic hepatitis caused by HCV. It is contemplated that earlier seroconversion to glycosylated structural antigens may be detectable by using proteins produced in these mammalian expression systems. Antibodies, both monoclonal and polyclonal, also may be produced from the proteins derived from these mammalian expression systems which then in turn may be used for diagnostic, prognostic and therapeutic applications.

Proteins produced from these mammalian expression systems, as well as reagents produced from these proteins, can be provided in the form of a kit with one or more containers such as vials or bottles, with each container containing a separate reagent such as a monoclonal antibody, or a cocktail of monoclonal antibodies, or a recombinant polypeptide, packaged as test kits for convenience in performing assays. Other aspects of the present invention include a polypeptide comprising an HCV epitope attached to a solid phase and an antibody to an HCV epitope attached to a solid phase. Also included are methods for producing a polypeptide containing an HCV epitope by incubating host cells transformed with a mammalian expression vector containing a sequence encoding a polypeptide containing an HCV epitope under conditions which allow expression of the polypeptide, and a polypeptide containing an HCV epitope produced by this method.

The present invention provides assays which utilize the recombinant proteins provided by the invention, as well as the antibodies described herein in various formats, any of which may employ a signal generating compound which generates a measurable signal in the assay. Assays which do not utilize signal generating compounds to provide a means of detection also are provided. All of the assays described generally detect either antigen or antibody, or both, and include mixing a test sample with at least one reagent provided herein to form at least one antigen/antibody complex and detecting the presence of the complex. These assays are described in detail herein.

Vaccines for treatment of HCV infection comprising an immunogenic peptide obtained from a mammalian expression system containing envelope genes from HCV as described herein are included in the present invention. Also included in the present invention is a method for producing antibodies to HCV comprising administering to an individual an isolated immunogenic polypeptide containing an HCV epitope in an amount sufficient to produce an immune response in the inoculated individual.

The term "antibody containing body component" (or test sample) refers to a component of an individual's body which is the source of the antibodies of interest. These components are well known in the art. These test samples include biological samples which can be tested by the methods of the present invention described herein and include human and animal body fluids such as whole blood, serum, plasma, cerebrospinal fluid, urine, lymph fluids, and various external sections of the respiratory, intestinal and genitourinary tracts, tears, saliva, milk, white blood cells, myelomas and the like, biological fluids such as cell culture supernatants, fixed tissue specimens and fixed cell specimens.

After preparing the recombinant proteins as described by the present invention, these recombinant proteins can be used to develop unique assays as described herein to detect either the presence of antigen or antibody to HCV. These compositions also can be used to develop monoclonal and/or polyclonal antibodies with a specific recombinant protein which specifically binds to the immunological epitope of HCV. Also, it is contemplated that at least one recombinant protein of the invention can be used to develop vaccines by following methods known in the art.

Typically, such vaccines are prepared as injectables, either as liquid solutions or suspensions; solid forms suitable for solution in or suspension in liquid prior to injection also may be prepared. The preparation may be emulsified, or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum hydroxide, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), and RIBI (RIBI Immunochemicals Res., U.S.A.) in a 2% squalene/Tween-80® emulsion. The effectiveness of an adjuvant may be determined by measuring the amount of antibodies directed against an immunogenic polypeptide containing an HCV antigenic sequence resulting from administration of this polypeptide in vaccines which also are comprised of the various adjuvants.

The vaccines usually are administered by intraveneous or intramuscular injection. Additional formulations which are suitable for other modes of administration include suppositories and, in some cases, oral formulations. For suppositories, traditional binders and carriers may include but are not limited to polyalkylene glycols or triglycerides. Such suppositories may be formed from mixtures containing the active ingredient in the range of about 0.5% to about 10%, preferably, about 1% to about 2%. Oral formulation include such normally employed excipients as, for example pharmaceutical grades of mannitol, lactose, starch, magnesium stearate, sodium saccharine, cellulose, magnesium carbonate and the like. These compositions may take the form of solutions, suspensions, tablets, pills, capsules, sustained release formulations or powders and contain about 10% to about 95% of active ingredient, preferably about 25% to about 70%.

The proteins used in the vaccine may be formulated into the vaccine as neutral or salt forms. Pharmaceutically acceptable salts such as acid addition salts (formed with free amino groups of the peptide) and which are formed with inorganic acids such as hydrochloric or phosphoric acids, or such organic acids such as acetic, oxalic, tartaric, maleic, and others known to those skilled in the art. Salts formed with the free carboxyl groups also may be derived from inorganic bases such as sodium, potassium, ammonium, calcium or ferric hydroxides and the like, and such organic bases such as isopropylamine, trimethylamine, 2-ethylamino ethanol, histidine procaine, and others known to those skilled in the art.

Vaccines are administered in a way compatible with the dosage formulation, and in such amounts as will be prophylactically and/or therapeutically effective. The quantity to be administered generally is in the range of about 5 micrograms to about 250 micrograms of antigen per dose, and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reenforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic HCV envelope antigen(s) may be administered in conjunction with other immunoregulatory agents, for example, with immune globulins.

It is contemplated that the reagent employed for the assay can be provided in the form of a kit with one or more containers such as vials or bottles, with each container containing a separate reagent such as a monoclonal antibody, or a cocktail of monoclonal antibodies, or a polypeptide (either recombinant or synthetic) employed in the assay.

"Solid phases" ("solid supports") are known to those in the art but not critical and include the walls of wells of a reaction tray, test tubes, polystyrene beads, magnetic or non-magnetic beads, nitrocellulose strips, membranes, microparticles such as latex particles, plastic tubes, glass or silicon chips and sheep red blood cells are all suitable examples and others. Suitable methods for immobilizing peptides on solid phases include ionic, hydrophobic, covalent interactions and the like. A "solid phase," as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is attached to the solid phase and which has the ability to immobilize the capture reagent through a specific binding reaction. The receptor molecule enables the indirect binding of the capture reagent to a solid phase material before the performance of the assay or during the performance of the assay.

It is contemplated and within the scope of the invention that the solid phase also can comprise any suitable porous material with sufficient porosity to allow access by detection antibodies and a suitable surface affinity to bind antigens.

Microporous structures are generally preferred, but materials with gel structure in the hydrated state may be used as well. Such useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carders, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described herein above are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272.

The "indicator reagent" comprises a "signal generating compound" (label) which is capable of generating, and generates, a measurable signal detectable by external means conjugated to a specific binding member for HCV. "Specific binding member" as used herein means a member of a specific binding pair. That is, two different molecules where one of the molecules through chemical or physical means specifically binds to the second molecule. In addition to being an antibody member of a specific binding pair for HCV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immuno-reactive specific binding member can be an antibody, an antigen, or an antibody/antigen complex that is capable of binding either to HCV as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds such as acridinium, phenanthfidinium and dioxetane compounds, radioactive elements, and direct visual labels. Examples of enzymes include alkaline phosphatase, horseradish peroxidase, β-galactosidase, and the like. The selection of a particular label is not critical, but it will be capable of producing a signal either by itself or in conjunction with one or more additional substances.

Other embodiments which utilize various other solid phases also are contemplated and are within the scope of this invention. For example, ion capture procedures for separating an immobilizable reaction complex with a negatively charged polymer, described in co-pending U.S. patent application Ser. No. 150,278 corresponding to EP publication 0326100, and U.S. patent application Ser. No. 375,029 (EP publication no. 0406473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115, which enjoys common ownership and which is incorporated herein by reference.

Also, the methods of the present invention can be adapted for use in systems which utilize microparticle technology including in automated and semi-automated systems wherein the solid phase comprises a microparticle. Such systems include those described in pending U.S. patent application Ser. Nos. 425,651 and 425,643, which correspond to published EPO applications Nos. EP 0 425 633 and EP 0 424 634, respectively, which are incorporated herein by reference.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercaptopropyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio]propionate), SMCC (succinimidyl-4-[N-maleimidomethyl]cyclohexane-1-carboxylate), SIAB (succinimidyl [4-iodoacetyl]aminobenzoate), and SMPB (succinimidyl 4-[1-maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000), Dextran T-110 (molecular weight 110,000), Dextran T-500 (molecular weight 500,000), Dextran T-2M (molecular weight 2,000,000) (all of which are available from Pharmacia, Piscataway, N.J.), or Ficoll (molecular weight 70,000 (available from Sigma Chemical Co., St. Louis, Mo.). Also, polyelectrolyte interactions may be used to immobilize a specific binding partner on a surface of a test piece by using techniques and chemistries described by pending U.S. patent application Ser. No. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

Recombinant proteins may be utilized to detect the presence of anti-HCV in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of HCV antibody. Other assay formats utilizing the proteins of the present invention are contemplated. These include contacting a test sample with a solid phase to which at least one recombinant protein produced in the mammalian expression system has been attached, incubating the solid phase and test sample for a time and under conditions sufficient to form antigen/antibody complexes, and then contacting the solid phase with a labeled recombinant antigen. Assays such as this and others are described in pending U.S. patent application Ser. No. 07/787,710, which enjoys common ownership and is incorporated herein by reference.

It is within the scope of the invention that antibodies, both monoclonal and polyclonal, can be generated using the fusion proteins of the invention as immunogens. The monoclonal antibodies or fragments thereof can be provided individually to detect HCV antigens. Combinations of the monoclonal antibodies (and fragments thereof) provided herein also may be used together as components in a mixture or "cocktail" of at least one anti-HCV antibody of the invention with antibodies to other HCV regions, each having different binding specificities. Thus, this cocktail can include monoclonal antibodies which are directed to HCV envelope proteins and other monoclonal antibodies to other antigenic determinants of the HCV genome. Methods for making monoclonal or polyclonal antibodies are well-known in the art. See, for example, Kohler and Milstein, *Nature* 256:494 (1975); J. G. R. Hurrel, ed., *Monoclonal Hybridoma Antibodies: Techniques and Applications*, CRC Press, Inc., Boco Raton, Fla. (1982); and L. T. Mimms et al., *Virology* 176:604–619 (1990), which are incorporated herein by reference.

The polyclonal antibody or fragment thereof which can be used in the assay formats should specifically bind to a specific HCV region or other HCV proteins used in the assay. The polyclonal antibody used preferably is of mammalian origin; human, goat, rabbit or sheep anti-HCV polyclonal antibody can be used. Most preferably, the polyclonal antibody is rabbit polyclonal anti-HCV antibody. The polyclonal antibodies used in the assays can be used either alone or as a cocktail of polyclonal antibodies. Since the cocktails used in the assay formats are comprised of either monoclonal antibodies or polyclonal antibodies having different HCV specificity, they would be useful for diagnosis, evaluation and prognosis of HCV infection, as well as for studying HCV protein differentiation and specificity.

In another assay format, the presence of antibody and/or antigen to HCV can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes.

The presence of one or more analytes is determined by detecting a signal generated in connection with the complexes formed on either or both solid phases as an indication of the presence of one or more analytes in the test sample. In this assay format, proteins derived from human expression systems may be utilized as well as monoclonal antibodies produced from the proteins derived from the mammalian expression systems as disclosed herein. Such assay systems are described in greater detail in pending U.S. patent application Ser. No. 07/574,821 entitled Simultaneous Assay for Detecting One Or More Analytes, filed Aug. 29, 1990, which enjoys common ownership and is incorporated herein by reference.

In yet another detection method, monoclonal antibodies produced by using the fusion proteins of the present invention can be employed in the detection of HCV antigens in fixed tissue sections, as well as fixed cells by immunohistochemical analysis. In addition, these monoclonal antibodies can be bound to matrices similar to CNBr-activated Sepharose and used for the affinity purification of specific HCV proteins from cell cultures, or biological tissues such as blood and liver. The monoclonal antibodies further can be used for the generation of chimeric antibodies for therapeutic use, or other similar applications.

In another alternate assay format, one or a combination of one or more monoclonal antibodies produced by using the fusion proteins of the present invention can be employed as a competitive probe for the detection of antibodies to HCV protein. For example, HCV proteins, either alone or in combination, can be coated on a solid phase. A test sample suspected of containing antibody to HCV antigen then is incubated with an indicator reagent comprising a signal generating compound and at least one monoclonal antibody for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANB hepatitis test sample indicates the presence of anti-HCV antibody in the test sample.

While the present invention discloses the preference for the use of solid phases, it is contemplated that the proteins of the present invention can be utilized in non-solid phase assay systems. These assay systems are known to those skilled in the art, and are considered to be within the scope of the present invention.

The present invention will now be described by way of examples, which are meant to illustrate, but not to limit, the spirit and scope of the invention.

EXAMPLES

Example 1

Generation of APP-HCV E1, APP-HCV E2, and APP-HCV E1-E2 fusion clones

All mammalian expression constructs were made in the vector pRc/CMV (available from Invitrogen, San Diego, Calif.), as shown in FIG. 1. However, it is contemplated that other expression vectors can be utilized for this and the other constucts described hereinbelow by following standard procedures known in the art. Some of the HCV and APP sequences used herein were described previously in U.S. patent application Ser. No. 08/144,099, previously incorporated herein by reference.

Figure 2:
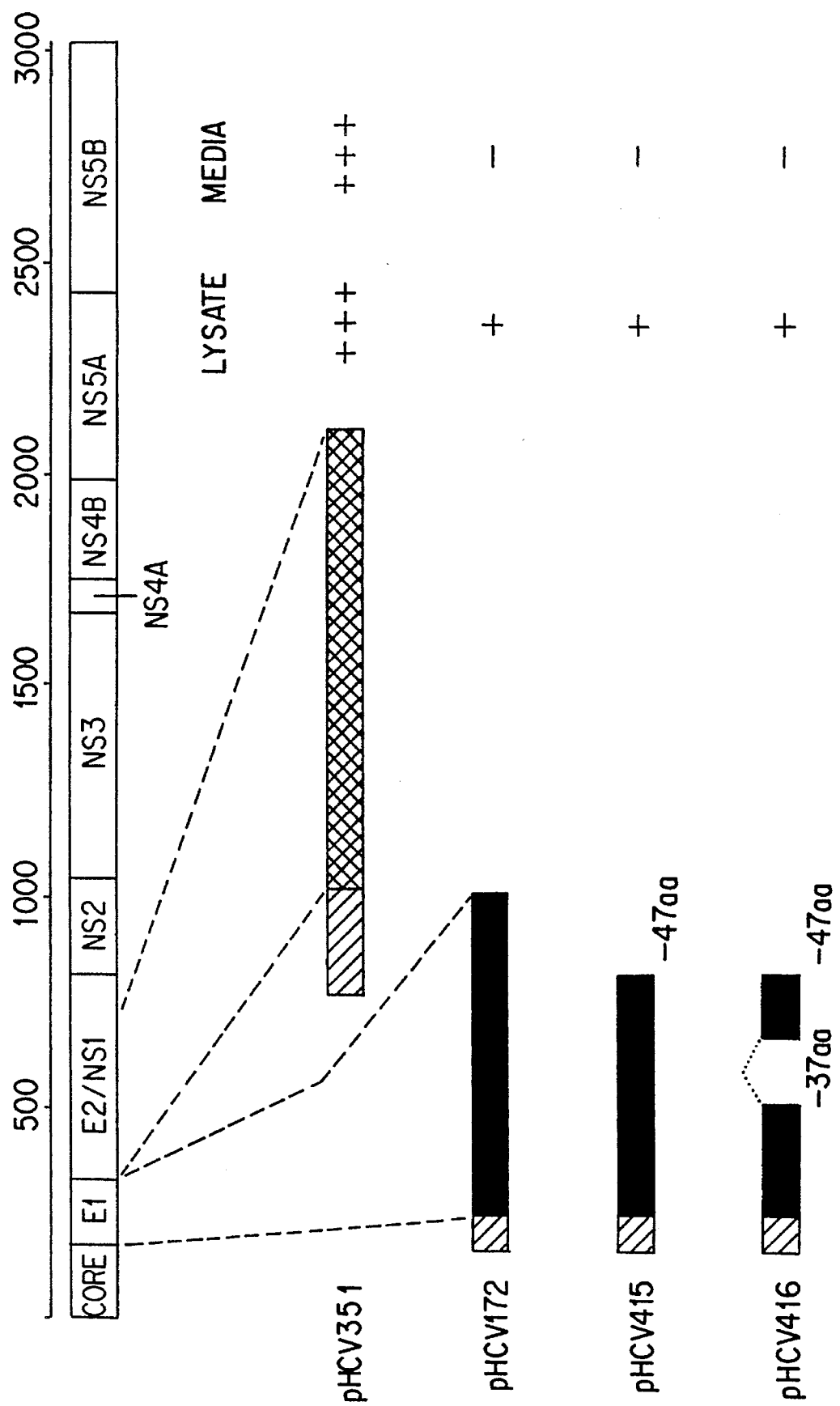
FIG. 2 presents a schematic representation of the location of amino acids of the APP-HCV E2 and APP-HCV E1 fusion proteins expressed by the mammalian expression vectors pHCV351, pHCV172, pHCV415, and pHCV416.

Clone pHCV172 (SEQ. ID. NO. 2) was constructed by combining amyloid precursor protein (APP) sequence, previously described by Kang et al., *Nature* 325:733–736 (1987), instead of human growth hormone signal sequence of pHCV168 (the nucleic acid sequence of pHCV 168 is presented as SEQ. ID. NO. 3, and the amino acid sequence of pHCV168 is presented as SEQ. ID. NO. 4) and full length of HCV E1, as shown in FIG. 2. A HindIII-KpnI fragment of the APP sequence was initially subcloned in HindIII and KpnI sites of pUC19. A HindIII-EcoRI fragment from this clone was ligated with an EcoRI-XbaI fragment of pHCV168 at HindIII and XbaI sites of pRc/CMV, resulting pHCV172 (SEQ. ID. NO. 2).

Clone pHCV415 (SEQ. ID. NO. 5), which has a deletion of the C-terminal hydrophobic region, was constructed as follows: pHCV172 (SEQ. ID. NO. 2) was digested with PvuII and HindIII and a fragment containing APP, and most part of E1 was cloned in HindIII and XbaI sites of the pRc/CMV, as shown in FIG. 2. Clone pHCV415 (SEQ. ID. NO. 5) has a deletion of amino acid 337 to 383 of HCV E1.

Clone pHCV 416 (SEQ. ID. NO. 6) was derived from pHCV415 (SEQ. ID. NO. 5), by removing a AcyI—AcyI fragment which contained the internal hydrophobic amino acid sequence 260 to 296 of E1, as shown in FIG. 2. Clone pHCV416 (SEQ. ID. NO. 6) contains HCV amino acid sequence from 192 to 259 and 297 to 336 of HCV.

Clone pHCV351 (SEQ. ID. NO. 7) was derived from pHCV167 (the nucleic acid sequence of pHCV167 is presented as SEQ. ID. NO. 8 and the amino acid sequence of pHCV167 is presented as SEQ. ID. NO. 9). pHCV 167 previously was described in the U.S. patent application Ser. No. 08/144,099. pHCV 351 (SEQ. ID. NO. 7) was cloned by inserting a termination codon after amino acid 654 of HCV E2, as shown in FIG. 2. Thus, this clone lacks C-terminal hydrophobic residues.

Figure 4:
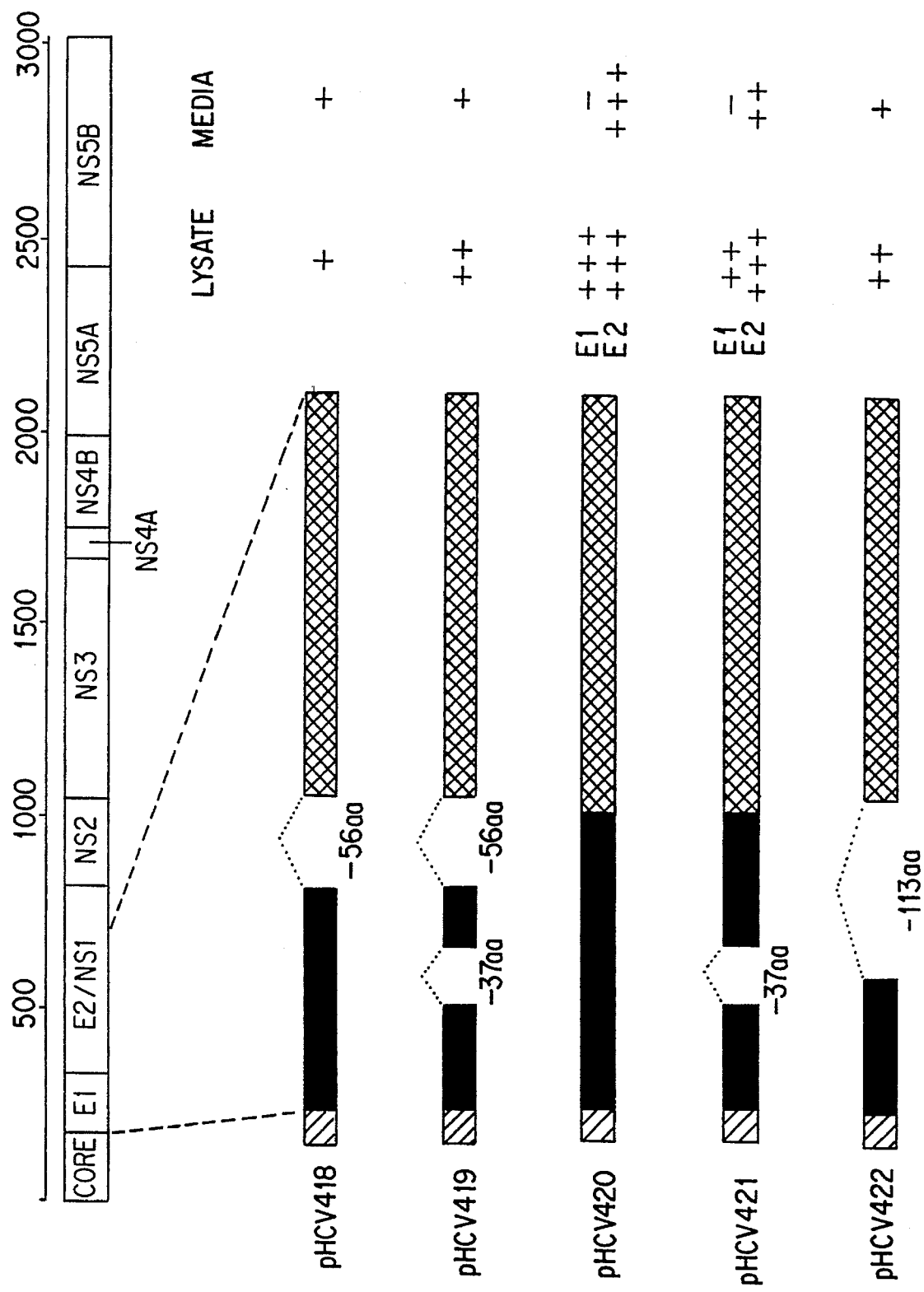
FIG. 4 presents a schematic representation of the location of amino acids of the APP-HCV E1-E2 fusion proteins expressed by the mammalian expression vectors pHCV418, pHCV419, pHCV420, pHCV421 and pHCV422.

Clone pHCV418 (SEQ. ID. NO. 10) was constructed as follows: pHCV172 (SEQ. ID. NO. 2) was digested with HindIII and PvuII and a fragment containing APP and E1 sequence (from amino acid 192 to 336) was isolated. Clone pHCV351 (SEQ. ID. NO. 7) was also digested with NaeI and XbaI, and a fragment containing amino acid 393 to 654 of E2 was isolated. These fragments were cloned between HindIII and XbaI sites of pRc/CMV, as shown in FIG. 4.

Clone pHCV419 (SEQ. ID. NO. 11) was constructed by removing an internal hydrophobic region residing on an AcyI—AcyI fragment from clone pHCV418 (SEQ. ID. NO. 10), as shown in FIG. 4. Thus, pHCV419 (SEQ. ID. NO. 11) contains HCV amino acid sequence from 192 to 259, 297 to 336 and 393 to 654.

Clone pHCV176 (SEQ. ID. NO. 12) contains a 5' half 5281 base pairs of the HCV sequence identified as SEQUENCE ID NO. 1. Briefly, RNA isolated from the serum or plasma of a chimpanzee (designated as "CO") experimentally infected with HCV was transcribed to cDNA using reverse transcriptase employing either random hexamer primers or specific anti-sense primers derived from the prototype HCV-1 sequence. The sequence has been reported by Choo et al. (Choo et al., *Proc. Nat'l. Acad, Sci. USA* 88:2451–2455 [1991], and is available through GenBank data base, Accession No. M62321). This cDNA then was amplified using PCR and AmpliTaq® DNA polymerase employing either a second sense primer located approximately 1000–2000 nucleotides upstream of the specific antisense primer or a pair of sense and antisense primers flanking a 1000–2000 nucleotide fragment of HCV. After 25 to 35 cycles of amplification following standard procedures known in the art, an aliquot of this reaction mixture was subjected to nested PCR (or "PCR-2"), wherein a pair of sense and antisense primers located internal to the original pair of PCR primers was employed to further amplify HCV gene segments in quantities sufficient for analysis and subcloning, utilizing endonuclease recognition sequences present in the second set of PCR primers. In this manner, seven adjacent HCV DNA fragments were generated which then could be assembled using the generic cloning strategy. Prior to assembly, the DNA sequence of each of the individual fragments was determined and translated into the genomic amino acid sequences presented in SEQUENCE ID. NO. 1. Two fragments (EcoRi-BglII 3231 bp and BglII-XbaI 2050 bp fragments) from two clones (pHCV141 [SEQ. ID. NO. 13] and pHCV150 [SEQ. ID. NO. 14]) were combined to generate pHCV176 (SEQ. ID. NO. 12). This method has been described in U.S. Ser. No. 08/144,099, which previously was incorporated herein by reference.

Clone pHCV420 (SEQ. ID. NO. 15) was constructed by combining three fragments: a PvuI-BamHI fragment from pHCV172 (SEQ. ID. NO. 2) containing 5' half of ampicilin resistance gene (PvuI site) to APP and E1 (BamHI site), a PvuI-SalI fragment from pHCV351 (SEQ. ID. NO. 7) containing 3' half of ampicilin resistance gene (PvuI site) to 3' end of E2 (SalI site) and a BamHI-SalI fragment from pHCV176 (SEQ. ID. NO. 12) containing 3' half of E1 and 5' half of E2, FIG. 4. Thus, pHCV420 (SEQ. ID. NO. 15) contains HCV amino acid sequence 192 to 654.

Clone pHCV421 (SEQ. ID. NO. 16) was derived from pHCV420 (SEQ. ID. NO. 15) by removing an internal hydrophobic region residing on an AcyI—AcyI fragment, as shown in FIG. 4.

Clone pHCV422 (SEQ. ID. NO. 17) was derived by ligating three fragments: a HindIII-AvaII fragment containing APP and amino acid 192 to 279 from pHCV420 (SEQ. ID. NO. 15) of E1 sequence, a NaeI-XbaI fragment containing amino acid sequence 393 to 654 of E2 from pHCV351 (SEQ. ID. NO. 7) and a HindIII-XbaI fragment from pRc/CMV, as shown in FIG. 4.

Figure 6:
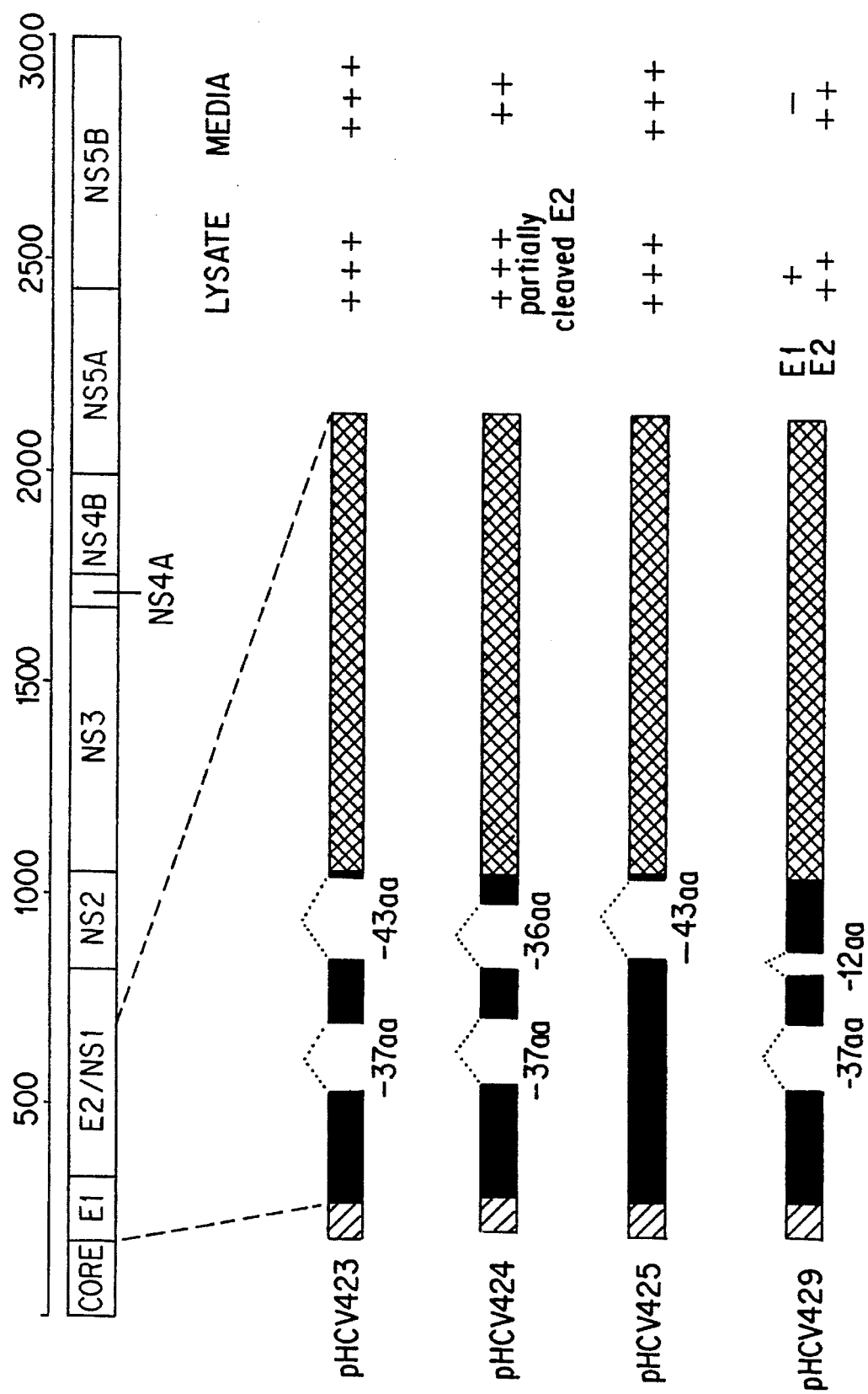
FIG. 6 presents a schematic representation of the location of amino acids of the APP-HCV E1-E2 fusion proteins expressed by the mammalian expression vectors pHCV423, pHCV424, pHCV425, and pHCV429.

Clones pHCV423 (SEQ. ID. NO. 18) and pHCV424 (SEQ. ID. NO. 19) were constructed as follows: pHCV421 (SEQ. ID. NO. 16) was digested with AvaII and NaeI to remove amino acid sequence 337 to 379 of E1 or was digested with PvuII and NcoI to remove amino acid sequence 337 to 363 of E1, as shown in FIG. 6.

Clone pHCV425 (SEQ. ID. NO. 20) was assembled from three fragments: a HindIII-PvuII from pHCV172 (SEQ. ID. NO. 2) containing APP and E1 up to amino acid sequence 336, a NaeI-XbaI fragment from pHCV420 (SEQ. ID. NO. 15) containing amino acid 380 to 383 of E1 and 384 to 654 of E2 and a HindIII-XbaI fragment from pRc/CMV, as shown in FIG. 6. Thus pHCV425 (SEQ. ID. NO. 20) contains HCV amino acid sequence 192 to 336 and 380 to 654.

Clone pHCV429 (SEQ. ID. NO. 21) was generated by removing a fragment containing amino acid sequence 328 to 339 residing on an AvaII-BamHI fragment of pHCV421 (SEQ. ID. NO. 16), as shown in FIG. 6.

Example 2

Detection of HCV Antigens by RIPA

A primary Human Embryonic Kidney (HEK) cell line transformed with human adenovirus type 5, designated as HEK-293 (available from the American Type Culture Collection, Rockville, Md.), was used for all transfections and expression analyses. HEK-293 cells were maintained in Minimum Essential Medium (MEM) which was supplemented with 10% fetal bovine serum (FBS), penicillin, streptomycin and fungizone.

Figure 3:
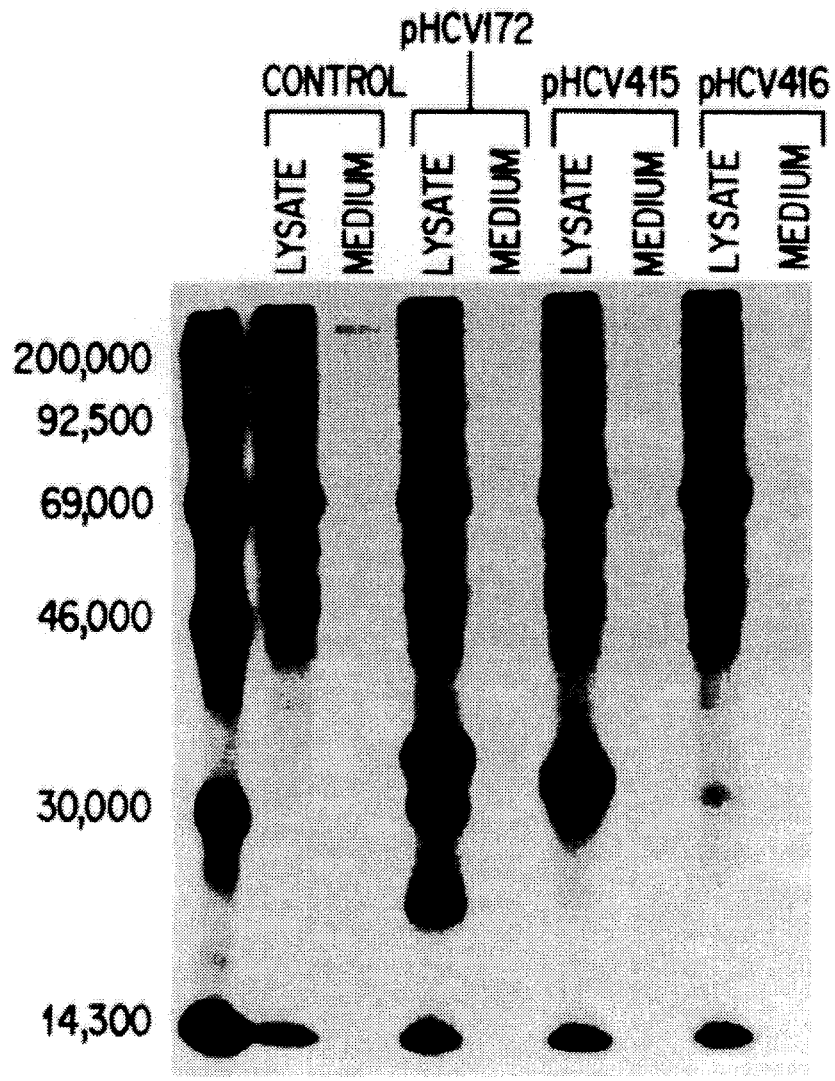
FIG. 3 presents radioimmunoprecipitation assay(RIPA) results obtained for APP-HCV E1 fusion proteins expressed by pHCV172, pHCV415 and pHCV416 in HEK-293 cells usidg HCV positive human sera.
Figure 5:
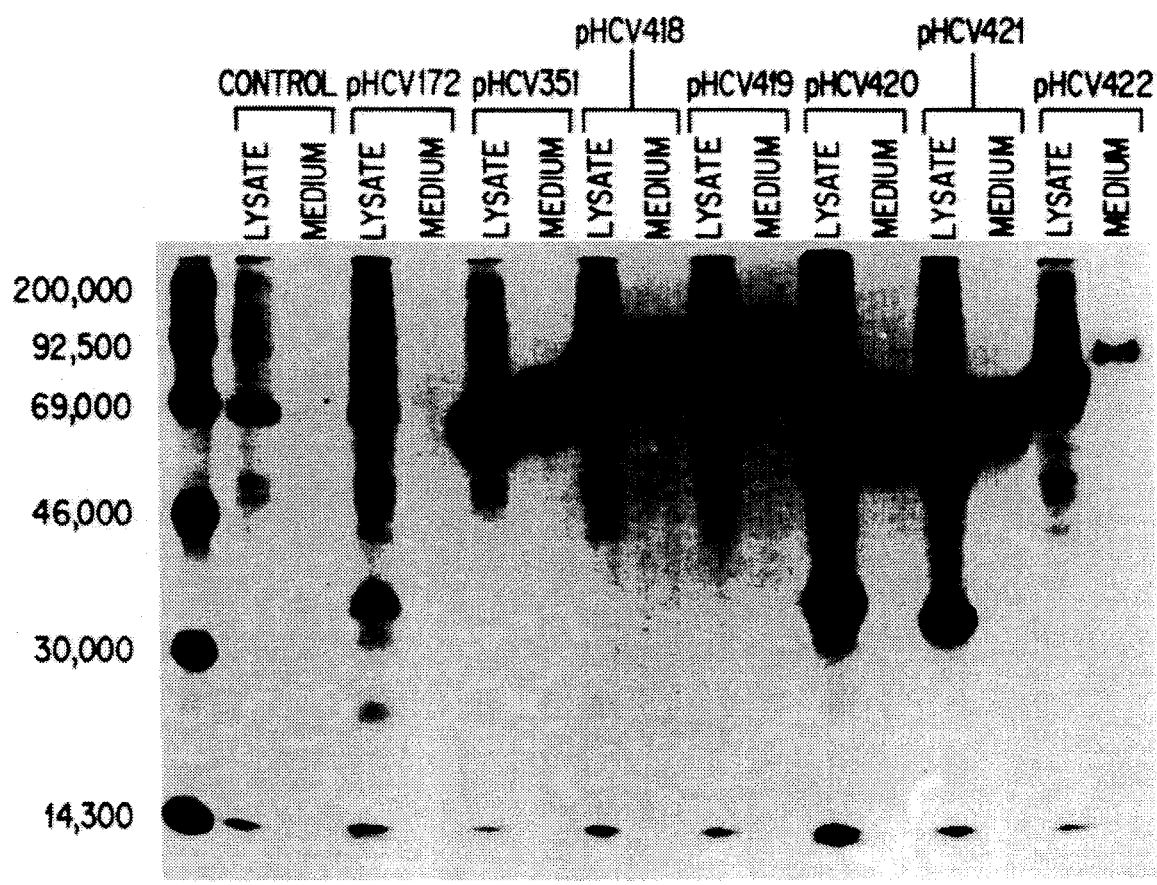
FIG. 5 presents RIPA results obtained for APP-HCV E1-E2 fusion proteins expressed by pHCV418, pHCV419, pHCV 420, pHCV 421 and pHCV422 in HEK-293 cells using human HCV patient sera.

Approximately 30 μg of purified DNA was transfected into HEK-293 cells using the modified calcium phosphate protocol as reported by Chen et al., *Molecular and Cellular Biology* 7(8):2745–2752 (1987). The calcium-phosphate-DNA solution was incubated on the HEK-293 cells for about 4 to 6 hours. The solution was removed, and then the cells were incubated in MEM for an additional 24 to 48 hours. In order to analyze protein expression, the transfected cells were metabolically labeled with 100 μCi/ml each of S-35 labeled methionine and cysteine for 8 to 14 hours. The culture media was removed and stored, and the cells were first washed in MEM and then lysed in phosphate buffered saline (PBS) containing 1% Triton X-100® (available from Sigma Chemical Co., St. Louis, Mo.), 0.1% sodium dodecyl sulfate (SDS), and 0.5% deoxychloate, designated as PBS-TDS. These cell lysates were left on ice for 10 to 15 minutes, and then clarified by centrifugation at 12,000×g for 45 minutes at 4° C. Standard radio-immunoprecipitation assays (RIPAs) then were conducted on those labeled cell lysates and/or culture medium. Briefly, labeled cell lysates (150 μl) and/or culture medium (400 μl) were incubated with 3 μl of HCV patient sera, designated as J728, at 4° C for one hour. Protein-A Sepharose, previously treated with cold HEK-293 cell lysate, then was added and the mixtures were further incubated for one hour at 4° C. with agitation. The samples were then centrifuged and the pellets were washed 3 times with PBS-TDS buffer. Proteins recovered by immunoprecipitation were eluted by heating in an electrophoresis sample buffer (50 mM Tris-HCl, pH 6.8, 100 mM dithiothreitol [DTT], 2% SDS, 0.1% bromophenol blue, and 10% glycerol) for six minutes in boiling water. The eluted proteins with carbon-14 labeled molecular weight standards (obtained from Amersham, Arlington Heights, Ill.) were separated by 13.5% polyacrylamide-SDS gels which were subsequently treated with a fluorographic reagent such as Enlightening® (available from NEN [DuPont], Boston, Mass.), dried under vacuum and exposed to x-ray film at −70° C. with intensifying screens. FIG. 3 shows that neither HCV E1 as a full length gene nor with the deletion of C-terminal hydrophobic region from E1, fused to APP (pHCV172 [SEQ. ID. NO. 2] or pHCV415 [SEQ. ID. NO. 5] in FIG. 2), was able to secrete its product. Removing an internal as well as a C-terminal hydrophobic regions was not sufficient to secrete E1 by APP signal sequence (pHCV416 [SEQ. ID. NO. 6] in FIG. 2). Thus, fusion of HCV E1-E2 with APP constructs were tested for possible ways to secrete E1 efficiently. FIG. 5 shows E2 with a C-terminal deletion was able to secrete its product into media efficiently using APP signal sequence (pHCV351 [SEQ. ID. NO. 7] in FIG. 2).

First, pHCV418 (SEQ. ID. NO. 10), pHCV419 (SEQ. ID. NO. 11) and pHCV422 (SEQ. ID. NO. 17) (FIG. 4), all lacking the cleavage site of HCV E1 and E2 at amino acid sequence 383/384 (Hijikata et al., *Proc. Natl. Acad. Sci. USA* 88: 5547–5551 [1991]), were tested for secretion of E1-E2 fusion protein. FIG. 5 shows that E1-E2 could be expressed in the culture medium and as well as in cells. Also, secreted materials seemed to be further glycosylated compared to the materials expressed in cell lysates. A second set of constructs (pHCV420 [SEQ. ID. NO. 15] and pHCV421 [SEQ. ID. NO. 16], FIG. 4) did not contain deletion at cleavage site of E1 and E2 at amino acid sequence 383/384. The RIPA in FIG. 5 shows that E1 and E2 were cleaved and that only E2 could be secreted into the medium. FIG. 5 also shows that the expression of E1 is much more efficient from pHCV420 (SEQ. ID. NO. 5) or pHCV421 (SEQ. ID. NO. 6) compared to expression from pHCV172, which does not contain E2 at the 3' side of E1. It is hypothesized that these types of fusion constructs, E2 after E1, may be a good way to increase expression levels and to secrete E1 as well as E2 into medium.

Figure 7:
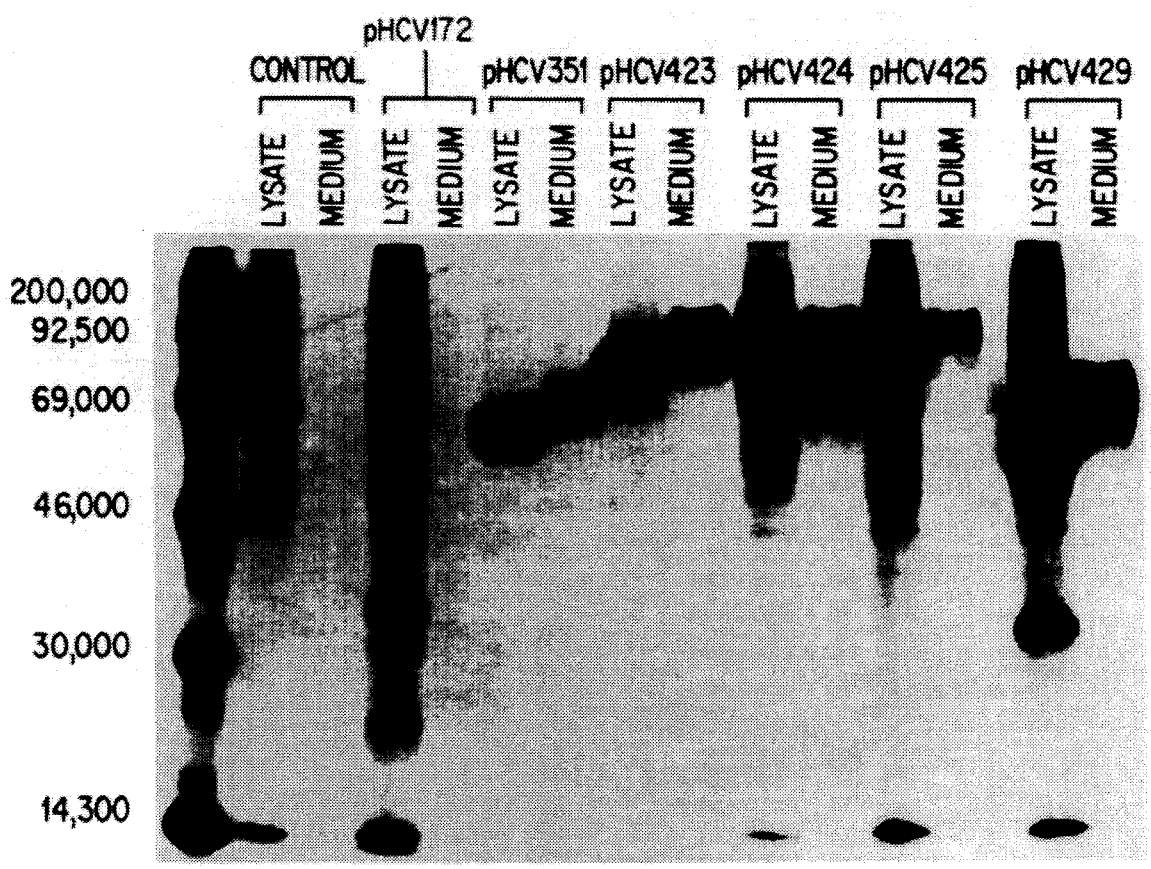
FIG. 7 presents RIPA results obtained for APP-HCV E1-E2 fusion proteins expressed by pHCV423, pHCV424, pHCV 425, and pHCV429 in HEK-293 cells using human HCV patient sera.

Clones pHCV 423 (SEQ. ID. NO. 18), pHCV424 (SEQ. ID. NO. 19), pHCV425 (SEQ. ID. NO. 20) and pHCV429 (SEQ. ID. NO. 21) (FIG. 6) were constructed to test the secretion of E1 as well as E2 from the same construct, as they contained the cleavage site of E1-E2 (amino acid 383/384). It was surprising and unexpected to discern that two constructs (pHCV423 [SEQ. ID. NO. 18] and pHCV425 [SEQ. ID. NO. 20]), containing the cleavage site of E1 and E2 (4 amino acids at the end of E1, and the same E2 as pHCV420), did not cleave E1 and E2, as shown in FIG. 7). However, their products were secreted into the medium as fusion proteins of E1-E2 (FIG. 7). The C-terminal sequence of E1 was increased in clones pHCV424 (SEQ. ID. NO. 19) and pHCV429 (SEQ. ID. NO. 21) compared to pHCV423 (SEQ. ID. NO. 18). Thus, various amounts of C-terminal hydrophobic sequence and a constant amount of internal hydrophobic sequence were removed to test the secretion of E1 and E2 from a same construct. FIG. 7 shows that the 20 amino acids at the end of E1 with E2 gave partial cleavage of E1 and E2. However, a 44 amino acid sequence (pHCV429, SEQ. ID. NO. 21) produced complete cleavage of E1 and E2, judging from the mobility of E2 on a gel. Although E1 expressed from pHCV429 (SEQ. ID. NO. 21) was readily detected in the cell lysate, E1 expressed from pHCV424 (SEQ. ID. NO. 19) was never detected in either the cell lysate or media. Further, E1 was never secreted from any constructs tested in the series of clones described herein.

These data demonstrate that HCV amino sequence 340 to 363 contains the E1 epitope. Thus, it was unexpected that the HCV E1 antigen could be secreted in a mammalian expression system. The clone pHCV425 (SEQ. ID. NO. 20) which contained the smallest deletion in the C-terminal of E1 ( the sequence shown in FIG. 8 (and presented as SEQ. ID. NO. 22) and the proposed cleavage site (amino acid 383/384) of E1-E2, secretes E1 and E2 as a fusion protein consisting amino acid sequence of HCV amino acid 192 to 336 and amino acid 383 to 654.

Clones pHCV172 (SEQ. ID. NO. 2), pHCV176 (SEQ. ID. NO. 12), pHCV351 (SEQ. ID. NO. 7 and pHCV425 (SEQ. ID. NO. 20) have been deposited at the American Type Culture Collection, 12301 Parklawn Drive, Rockville, Md., 20852, as of Jan. 14, 1994 under the terms of the Budapest Treaty, and accorded the following ATCC Designation Numbers: Clone pHCV172 was accorded ATCC deposit number 69533, clone pHCV176 was accorded ATCC deposit number 69534, clone pHCV351 was accorded ATCC deposit number 69535 and clone pHCV425 was accorded ATCC deposit number 69536. The designated deposits will be maintained for a period of thirty (30) years from the date of deposit, or for five (5) years after the last request for the deposit; or for the enforceable life of the U.S. patent, whichever is longer. All restrictions on the availability of the deposited materials will be irrevocably removed upon the granting of the patent. These deposits and other deposited materials mentioned herein are intended for convenience only, and are not required to practice the invention in view of the descriptions herein.

Other variations of applications of the use of the proteins and mammalian expression systems provided herein will be apparent to those skilled in the art. Accordingly, the invention is intended to be limited only in accordance with the appended claims.

What is claimed is:

1. A method of detecting hepatitis C virus, HCV, antigen or antibody in a test sample suspected of containing HCV antigen or antibody comprising contacting the test sample with a glycosylated HCV envelope antigen fusion protein expressed by plasmid pHCV425, wherein said fusion protein is produced in a mammalian expression system; and detecting the presence of binding complexes containing said HCV envelope antigen fusion protein, said binding complexes indicating the presence of HCV antigen or antibody in said test sample.

2. A method for detecting HCV antigen or antibody in a test sample suspected of containing HCV antigen or antibody comprising contacting the test sample with an antibody that specifically binds HCV antigen, said antibody having been produced in response to a glycosylated HCV envelope antigen fusion protein, wherein said fusion protein is expressed by plasmid pHCV425 and said fusion protein is produced in a mammalian expression system; and detecting the presence of binding complexes containing said antibody produced in response to said fusion protein, said binding complexes indicating the presence of HCV antigen or antibody in said test sample.

3. The method of claim 2 wherein said antibody produced in response to said glycosylated HCV envelope antigen fusion protein is a monoclonal antibody.

4. The method of claim 2 wherein said antibody produced in response to said glycosylated HCV envelope antigen fusion protein is a polyclonal antibody.

5. A test kit for detecting the presence of HCV antigen or antibody, comprising:

a container containing an antibody that specifically binds HCV antigen, said antibody having been produced in response to a glycosylated HCV envelope antigen fusion protein, wherein said fusion protein is expressed by a plasmid selected from the group consisting of pHCV172, pHCV351 and pHCV425, and said fusion protein is produced in a mammalian expression system.

6. The test kit of claim 5 wherein said antibody produced in response to said glycosylated HCV envelope antigen fusion protein is a polyclonal antibody.

7. The test kit of claim 5 wherein said antibody produced in response to said glycosylated HCV envelope antigen fusion protein is a monoclonal antibody.

\* \* \* \* \*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 3011 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80
```

-continued

```
Tyr  Pro  Trp  Pro  Leu  Tyr  Gly  Asn  Glu  Gly  Cys  Gly  Trp  Ala  Gly  Trp
               85                      90                      95

Leu  Leu  Ser  Pro  Arg  Gly  Ser  Arg  Pro  Ser  Trp  Gly  Pro  Thr  Asp  Pro
              100                     105                     110

Arg  Arg  Arg  Ser  Arg  Asn  Leu  Gly  Lys  Val  Ile  Asp  Thr  Leu  Thr  Cys
         115                     120                     125

Gly  Phe  Ala  Asp  Leu  Met  Gly  Tyr  Ile  Pro  Leu  Val  Gly  Ala  Pro  Leu
     130                     135                     140

Gly  Gly  Ala  Ala  Arg  Ala  Leu  Ala  His  Gly  Val  Arg  Val  Leu  Glu  Asp
145                     150                     155                     160

Gly  Val  Asn  Tyr  Ala  Thr  Gly  Asn  Leu  Pro  Gly  Cys  Ser  Phe  Ser  Ile
                165                     170                     175

Phe  Leu  Leu  Ala  Leu  Leu  Ser  Cys  Leu  Thr  Val  Pro  Ala  Ser  Ala  Tyr
               180                     185                     190

Gln  Val  Arg  Asn  Ser  Ser  Gly  Leu  Tyr  His  Val  Thr  Asn  Asp  Cys  Pro
              195                     200                     205

Asn  Ser  Ser  Ile  Val  Tyr  Glu  Ala  Ala  Asp  Ala  Ile  Leu  His  Thr  Pro
     210                     215                     220

Gly  Cys  Val  Pro  Cys  Val  Arg  Glu  Gly  Asn  Ala  Ser  Arg  Cys  Trp  Val
225                     230                     235                     240

Ala  Val  Thr  Pro  Thr  Val  Ala  Thr  Arg  Asp  Gly  Lys  Leu  Pro  Thr  Thr
                245                     250                     255

Gln  Leu  Arg  Arg  His  Ile  Asp  Leu  Leu  Val  Gly  Ser  Ala  Thr  Leu  Cys
              260                     265                     270

Ser  Ala  Leu  Tyr  Val  Gly  Asp  Leu  Cys  Gly  Ser  Val  Phe  Leu  Val  Gly
               275                     280                     285

Gln  Leu  Phe  Thr  Phe  Ser  Pro  Arg  Arg  His  Trp  Thr  Thr  Gln  Asp  Cys
     290                     295                     300

Asn  Cys  Ser  Ile  Tyr  Pro  Gly  His  Ile  Thr  Gly  His  Arg  Met  Ala  Trp
305                     310                     315                     320

Asp  Met  Met  Met  Asn  Trp  Ser  Pro  Thr  Ala  Ala  Leu  Val  Val  Ala  Gln
              325                     330                     335

Leu  Leu  Arg  Ile  Pro  Gln  Ala  Ile  Leu  Asp  Met  Ile  Ala  Gly  Ala  His
              340                     345                     350

Trp  Gly  Val  Leu  Ala  Gly  Ile  Ala  Tyr  Phe  Ser  Met  Val  Gly  Asn  Trp
          355                     360                     365

Ala  Lys  Val  Leu  Val  Val  Leu  Leu  Leu  Phe  Ala  Gly  Val  Asp  Ala  Glu
     370                     375                     380

Thr  His  Val  Thr  Gly  Gly  Ser  Ala  Gly  His  Thr  Thr  Ala  Gly  Leu  Val
385                     390                     395                     400

Arg  Leu  Leu  Ser  Pro  Gly  Ala  Lys  Gln  Asn  Ile  Gln  Leu  Ile  Asn  Thr
              405                     410                     415

Asn  Gly  Ser  Trp  His  Ile  Asn  Ser  Thr  Ala  Leu  Asn  Cys  Asn  Glu  Ser
               420                     425                     430

Leu  Asn  Thr  Gly  Trp  Leu  Ala  Gly  Leu  Phe  Tyr  His  His  Lys  Phe  Asn
          435                     440                     445

Ser  Ser  Gly  Cys  Pro  Glu  Arg  Leu  Ala  Ser  Cys  Arg  Arg  Leu  Thr  Asp
     450                     455                     460

Phe  Ala  Gln  Gly  Gly  Gly  Pro  Ile  Ser  Tyr  Ala  Asn  Gly  Ser  Gly  Leu
465                     470                     475                     480

Asp  Glu  Arg  Pro  Tyr  Cys  Trp  His  Tyr  Pro  Pro  Arg  Pro  Cys  Gly  Ile
               485                     490                     495
```

```
Val  Pro  Ala  Lys  Ser  Val  Cys  Gly  Pro  Val  Tyr  Cys  Phe  Thr  Pro  Ser
               500                      505                     510

Pro  Val  Val  Val  Gly  Thr  Thr  Asp  Arg  Ser  Gly  Ala  Pro  Thr  Tyr  Ser
               515                      520                     525

Trp  Gly  Ala  Asn  Asp  Thr  Asp  Val  Phe  Val  Leu  Asn  Asn  Thr  Arg  Pro
     530                      535                     540

Pro  Leu  Gly  Asn  Trp  Phe  Gly  Cys  Thr  Trp  Met  Asn  Ser  Thr  Gly  Phe
545                      550                      555                          560

Thr  Lys  Val  Cys  Gly  Ala  Pro  Pro  Cys  Val  Ile  Gly  Gly  Val  Gly  Asn
               565                      570                          575

Asn  Thr  Leu  Leu  Cys  Pro  Thr  Asp  Cys  Phe  Arg  Lys  His  Pro  Glu  Ala
               580                      585                     590

Thr  Tyr  Ser  Arg  Cys  Gly  Ser  Gly  Pro  Trp  Ile  Thr  Pro  Arg  Cys  Met
          595                      600                     605

Val  Asp  Tyr  Pro  Tyr  Arg  Leu  Trp  His  Tyr  Pro  Cys  Thr  Ile  Asn  Tyr
     610                      615                     620

Thr  Ile  Phe  Lys  Val  Arg  Met  Tyr  Val  Gly  Gly  Val  Glu  His  Arg  Leu
625                      630                      635                          640

Glu  Ala  Ala  Cys  Asn  Trp  Thr  Arg  Gly  Glu  Arg  Cys  Asp  Leu  Glu  Asp
                    645                      650                     655

Arg  Asp  Arg  Ser  Glu  Leu  Ser  Pro  Leu  Leu  Ser  Thr  Thr  Gln  Trp
               660                      665                     670

Gln  Val  Leu  Pro  Cys  Ser  Phe  Thr  Thr  Leu  Pro  Ala  Leu  Ser  Thr  Gly
               675                      680                     685

Leu  Ile  His  Leu  His  Gln  Asn  Ile  Val  Asp  Val  Gln  Tyr  Leu  Tyr  Gly
          690                      695                     700

Val  Gly  Ser  Ser  Ile  Ala  Ser  Trp  Ala  Ile  Lys  Trp  Glu  Tyr  Val  Val
705                      710                      715                          720

Leu  Leu  Phe  Leu  Leu  Leu  Ala  Asp  Ala  Arg  Val  Cys  Ser  Cys  Leu  Trp
               725                      730                     735

Met  Met  Leu  Leu  Ile  Ser  Gln  Ala  Glu  Ala  Ala  Leu  Glu  Asn  Leu  Val
               740                      745                     750

Ile  Leu  Asn  Ala  Ala  Ser  Leu  Ala  Gly  Thr  His  Gly  Phe  Val  Ser  Phe
          755                      760                     765

Leu  Val  Phe  Phe  Cys  Phe  Ala  Trp  Tyr  Leu  Lys  Gly  Arg  Trp  Val  Pro
     770                      775                     780

Gly  Ala  Ala  Tyr  Ala  Leu  Tyr  Gly  Ile  Trp  Pro  Leu  Leu  Leu  Leu  Leu
785                      790                      795                          800

Leu  Ala  Leu  Pro  Gln  Arg  Ala  Tyr  Ala  Leu  Asp  Thr  Glu  Val  Ala  Ala
               805                      810                     815

Ser  Cys  Gly  Gly  Val  Val  Leu  Val  Gly  Leu  Met  Ala  Leu  Thr  Leu  Ser
               820                      825                     830

Pro  Tyr  Tyr  Lys  Arg  Tyr  Ile  Ser  Trp  Cys  Met  Trp  Trp  Leu  Gln  Tyr
          835                      840                     845

Phe  Leu  Thr  Arg  Val  Glu  Ala  Gln  Leu  His  Val  Trp  Val  Pro  Pro  Leu
     850                      855                     860

Asn  Val  Arg  Gly  Gly  Arg  Asp  Ala  Val  Ile  Leu  Leu  Met  Cys  Ala  Val
865                      870                      875                          880

His  Pro  Thr  Leu  Val  Phe  Asp  Ile  Thr  Lys  Leu  Leu  Leu  Ala  Ile  Phe
               885                      890                     895

Gly  Pro  Leu  Trp  Ile  Leu  Gln  Ala  Ser  Leu  Leu  Lys  Val  Pro  Tyr  Phe
               900                      905                     910

Val  Arg  Val  Gln  Gly  Leu  Leu  Arg  Ile  Cys  Ala  Leu  Ala  Arg  Lys  Ile
               915                      920                     925
```

```
Ala  Gly  Gly  His  Tyr  Val  Gln  Met  Ile  Phe  Ile  Lys  Leu  Gly  Ala  Leu
     930                      935                 940

Thr  Gly  Thr  Tyr  Val  Tyr  Asn  His  Leu  Thr  Pro  Leu  Arg  Asp  Trp  Ala
945                      950                 955                           960

His  Asn  Gly  Leu  Arg  Asp  Leu  Ala  Val  Ala  Val  Glu  Pro  Val  Val  Phe
               965                      970                           975

Ser  Arg  Met  Glu  Thr  Lys  Leu  Ile  Thr  Trp  Gly  Ala  Asp  Thr  Ala  Ala
               980                 985                      990

Cys  Gly  Asp  Ile  Ile  Asn  Gly  Leu  Pro  Val  Ser  Ala  Arg  Arg  Gly  Gln
               995                 1000                     1005

Glu  Ile  Leu  Leu  Gly  Pro  Ala  Asp  Gly  Met  Val  Ser  Lys  Gly  Trp  Arg
     1010                     1015                 1020

Leu  Leu  Ala  Pro  Ile  Thr  Ala  Tyr  Ala  Gln  Gln  Thr  Arg  Gly  Leu  Leu
1025                     1030                 1035                          1040

Gly  Cys  Ile  Ile  Thr  Ser  Leu  Thr  Gly  Arg  Asp  Lys  Asn  Gln  Val  Glu
               1045                 1050                     1055

Gly  Glu  Val  Gln  Ile  Val  Ser  Thr  Ala  Thr  Gln  Thr  Phe  Leu  Ala  Thr
          1060                 1065                      1070

Cys  Ile  Asn  Gly  Val  Cys  Trp  Thr  Val  Tyr  His  Gly  Ala  Gly  Thr  Arg
               1075                 1080                     1085

Thr  Ile  Ala  Ser  Pro  Lys  Gly  Pro  Val  Ile  Gln  Met  Tyr  Thr  Asn  Val
     1090                     1095                 1100

Asp  Gln  Asp  Leu  Val  Gly  Trp  Pro  Ala  Pro  Gln  Gly  Ser  Arg  Ser  Leu
1105                     1110                 1115                          1120

Thr  Pro  Cys  Thr  Cys  Gly  Ser  Ser  Asp  Leu  Tyr  Leu  Val  Thr  Arg  His
               1125                 1130                     1135

Ala  Asp  Val  Ile  Pro  Val  Arg  Arg  Gln  Gly  Asp  Ser  Arg  Gly  Ser  Leu
               1140                 1145                     1150

Leu  Ser  Pro  Arg  Pro  Ile  Ser  Tyr  Leu  Lys  Gly  Ser  Ser  Gly  Gly  Pro
               1155                 1160                     1165

Leu  Leu  Cys  Pro  Ala  Gly  His  Ala  Val  Gly  Leu  Phe  Arg  Ala  Ala  Val
     1170                     1175                 1180

Cys  Thr  Arg  Gly  Val  Ala  Lys  Ala  Val  Asp  Phe  Ile  Pro  Val  Glu  Asn
1185                     1190                 1195                          1200

Leu  Glu  Thr  Thr  Met  Arg  Ser  Pro  Val  Phe  Thr  Asp  Asn  Ser  Ser  Pro
               1205                 1210                     1215

Pro  Ala  Val  Pro  Gln  Ser  Phe  Gln  Val  Ala  His  Leu  His  Ala  Pro  Thr
               1220                 1225                     1230

Gly  Ser  Gly  Lys  Ser  Thr  Lys  Val  Pro  Ala  Ala  Tyr  Ala  Ala  Gln  Gly
               1235                 1240                     1245

Tyr  Lys  Val  Leu  Val  Leu  Asn  Pro  Ser  Val  Ala  Ala  Thr  Leu  Gly  Phe
     1250                     1255                 1260

Gly  Ala  Tyr  Met  Ser  Lys  Ala  His  Gly  Val  Asp  Pro  Asn  Ile  Arg  Thr
1265                     1270                 1275                          1280

Gly  Val  Arg  Thr  Ile  Thr  Thr  Gly  Ser  Pro  Ile  Thr  Tyr  Ser  Thr  Tyr
               1285                 1290                     1295

Gly  Lys  Phe  Leu  Ala  Asp  Gly  Gly  Cys  Ser  Gly  Gly  Ala  Tyr  Asp  Ile
               1300                 1305                     1310

Ile  Ile  Cys  Asp  Glu  Cys  His  Ser  Thr  Asp  Ala  Thr  Ser  Ile  Leu  Gly
               1315                 1320                     1325

Ile  Gly  Thr  Val  Leu  Asp  Gln  Ala  Glu  Thr  Ala  Gly  Ala  Arg  Leu  Val
     1330                     1335                 1340
```

```
Val  Leu  Ala  Thr  Ala  Thr  Pro  Pro  Gly  Ser  Val  Thr  Val  Pro  His  Pro
1345                1350                1355                     1360

Asn  Ile  Glu  Glu  Val  Ala  Leu  Ser  Thr  Thr  Gly  Glu  Ile  Pro  Phe  Tyr
                    1365                1370                     1375

Gly  Lys  Ala  Ile  Pro  Leu  Glu  Val  Ile  Lys  Gly  Gly  Arg  His  Leu  Ile
               1380                1385                     1390

Phe  Cys  His  Ser  Lys  Lys  Lys  Cys  Asp  Glu  Leu  Ala  Ala  Lys  Leu  Val
               1395                1400                     1405

Ala  Leu  Gly  Ile  Asn  Ala  Val  Ala  Tyr  Tyr  Arg  Gly  Leu  Asp  Val  Ser
     1410                1415                1420

Val  Ile  Pro  Ala  Ser  Gly  Asp  Val  Val  Val  Ser  Thr  Asp  Ala  Leu
1425                1430                1435                     1440

Met  Thr  Gly  Phe  Thr  Gly  Asp  Phe  Asp  Pro  Val  Ile  Asp  Cys  Asn  Thr
                    1445                1450                     1455

Cys  Val  Thr  Gln  Thr  Val  Asp  Phe  Ser  Leu  Asp  Pro  Thr  Phe  Thr  Ile
               1460                1465                     1470

Glu  Thr  Thr  Thr  Leu  Pro  Gln  Asp  Ala  Val  Ser  Arg  Thr  Gln  Arg  Arg
               1475                1480                     1485

Gly  Arg  Thr  Gly  Arg  Gly  Lys  Pro  Gly  Ile  Tyr  Arg  Phe  Val  Ala  Pro
     1490                1495                1500

Gly  Glu  Arg  Pro  Ser  Gly  Met  Phe  Asp  Ser  Ser  Val  Leu  Cys  Glu  Cys
1505                1510                1515                     1520

Tyr  Asp  Ala  Gly  Cys  Ala  Trp  Tyr  Glu  Leu  Thr  Pro  Ala  Glu  Thr  Thr
                    1525                1530                     1535

Val  Arg  Leu  Arg  Ala  Tyr  Met  Asn  Thr  Pro  Gly  Leu  Pro  Val  Cys  Gln
               1540                1545                     1550

Asp  His  Leu  Glu  Phe  Trp  Glu  Gly  Val  Phe  Thr  Gly  Leu  Thr  His  Ile
               1555                1560                     1565

Asp  Ala  His  Phe  Leu  Ser  Gln  Thr  Lys  Gln  Ser  Gly  Glu  Asn  Phe  Pro
1570                1575                1580

Tyr  Leu  Val  Ala  Tyr  Gln  Ala  Thr  Val  Cys  Ala  Arg  Ala  Gln  Ala  Pro
1585                1590                1595                     1600

Pro  Pro  Ser  Trp  Asp  Gln  Met  Trp  Lys  Cys  Leu  Ile  Arg  Leu  Lys  Pro
                    1605                1610                     1615

Thr  Leu  His  Gly  Pro  Thr  Pro  Leu  Leu  Tyr  Arg  Leu  Gly  Ala  Val  Gln
               1620                1625                     1630

Asn  Glu  Ile  Thr  Leu  Thr  His  Pro  Val  Thr  Lys  Tyr  Ile  Met  Thr  Cys
               1635                1640                     1645

Met  Ser  Ala  Asn  Pro  Glu  Val  Val  Thr  Ser  Thr  Trp  Val  Leu  Val  Gly
     1650                1655                1660

Gly  Val  Leu  Ala  Ala  Leu  Ala  Ala  Tyr  Cys  Leu  Ser  Thr  Gly  Cys  Val
1665                1670                1675                     1680

Val  Ile  Val  Gly  Arg  Ile  Val  Leu  Ser  Gly  Lys  Pro  Ala  Ile  Ile  Pro
                    1685                1690                     1695

Asp  Arg  Glu  Val  Leu  Tyr  Gln  Glu  Phe  Asp  Glu  Met  Glu  Glu  Cys  Ser
               1700                1705                     1710

Gln  His  Leu  Pro  Tyr  Ile  Glu  Gln  Gly  Met  Met  Leu  Ala  Glu  Gln  Phe
          1715                1720                     1725

Lys  Gln  Glu  Ala  Leu  Gly  Leu  Leu  Gln  Thr  Ala  Ser  Arg  Gln  Ala  Glu
     1730                1735                1740

Val  Ile  Thr  Pro  Ala  Val  Gln  Thr  Asn  Trp  Gln  Lys  Leu  Glu  Ala  Phe
1745                1750                1755                     1760

Trp  Ala  Lys  His  Met  Trp  Asn  Phe  Ile  Ser  Gly  Thr  Gln  Tyr  Leu  Ala
                    1765                1770                     1775
```

```
Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Ser Gln Thr Leu Leu
            1795                1800                1805

Phe Asn Ile Leu Gly Gly Trp Val Ala Ala Gln Leu Ala Ala Pro Gly
        1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
                1845                1850                1855

Ala Gly Val Ala Gly Ala Leu Val Ala Phe Lys Ile Met Ser Gly Glu
                1860                1865                1870

Val Pro Ser Thr Glu Asp Leu Val Asn Leu Leu Pro Ala Ile Leu Ser
            1875                1880                1885

Pro Gly Ala Leu Val Val Gly Val Val Cys Ala Ala Ile Leu Arg Arg
            1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Leu Ser Asn Leu Thr
                1940                1945                1950

Val Thr Gln Leu Leu Arg Arg Leu His Gln Trp Ile Gly Ser Glu Cys
            1955                1960                1965

Thr Thr Pro Cys Ser Gly Ser Trp Leu Arg Asp Ile Trp Asp Trp Ile
            1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
            2020                2025                2030

Ala Glu Ile Thr Gly His Val Lys Asn Gly Thr Met Arg Ile Val Gly
            2035                2040                2045

Pro Arg Thr Cys Arg Asn Met Trp Ser Gly Thr Phe Pro Ile Asn Ala
            2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Met Thr Thr Asp Asn Leu Lys Cys
                2100                2105                2110

Pro Cys Gln Ile Pro Ser Pro Glu Phe Phe Thr Glu Leu Asp Gly Val
            2115                2120                2125

Arg Leu His Arg Phe Ala Pro Pro Cys Lys Pro Leu Leu Arg Glu Glu
            2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
                2180                2185                2190
```

```
Gly  Ser  Pro  Pro  Ser  Met  Ala  Ser  Ser  Ser  Ala  Ser  Gln  Leu  Ser  Ala
              2195                2200                2205

Pro  Ser  Leu  Lys  Ala  Thr  Cys  Thr  Thr  Asn  His  Asp  Ser  Pro  Asp  Ala
2210                2215                2220

Glu  Leu  Ile  Glu  Ala  Asn  Leu  Leu  Trp  Arg  Gln  Glu  Met  Gly  Gly  Asn
2225                2230                2235                          2240

Ile  Thr  Arg  Val  Glu  Ser  Glu  Asn  Lys  Val  Val  Ile  Leu  Asp  Ser  Phe
              2245                2250                          2255

Asp  Pro  Leu  Val  Ala  Glu  Glu  Asp  Glu  Arg  Glu  Val  Ser  Val  Pro  Ala
              2260                2265                2270

Glu  Ile  Leu  Arg  Lys  Ser  Gln  Arg  Phe  Ala  Arg  Ala  Leu  Pro  Val  Trp
              2275                2280                2285

Ala  Arg  Pro  Asp  Tyr  Asn  Pro  Pro  Leu  Ile  Glu  Thr  Trp  Lys  Glu  Pro
              2290                2295                2300

Asp  Tyr  Glu  Pro  Pro  Val  Val  His  Gly  Cys  Pro  Leu  Pro  Pro  Pro  Arg
2305                2310                2315                          2320

Ser  Pro  Pro  Val  Pro  Pro  Pro  Arg  Lys  Lys  Arg  Thr  Val  Val  Leu  Thr
              2325                2330                2335

Glu  Ser  Thr  Leu  Ser  Thr  Ala  Leu  Ala  Glu  Leu  Ala  Thr  Lys  Ser  Phe
              2340                2345                2350

Gly  Ser  Ser  Ser  Thr  Ser  Gly  Ile  Thr  Gly  Asp  Asn  Thr  Thr  Thr  Ser
              2355                2360                2365

Ser  Glu  Pro  Ala  Pro  Ser  Gly  Cys  Pro  Pro  Asp  Ser  Asp  Val  Glu  Ser
              2370                2375                2380

Tyr  Ser  Ser  Met  Pro  Pro  Leu  Glu  Gly  Glu  Pro  Gly  Asp  Pro  Asp  Phe
2385                2390                2395                          2400

Ser  Asp  Gly  Ser  Trp  Ser  Thr  Val  Ser  Ser  Gly  Ala  Asp  Thr  Glu  Asp
              2405                2410                2415

Val  Val  Cys  Cys  Ser  Met  Ser  Tyr  Ser  Trp  Thr  Gly  Ala  Leu  Val  Thr
              2420                2425                2430

Pro  Cys  Ala  Ala  Glu  Glu  Gln  Lys  Leu  Pro  Ile  Asn  Ala  Leu  Ser  Asn
              2435                2440                2445

Ser  Leu  Leu  Arg  His  His  Asn  Leu  Val  Tyr  Ser  Thr  Thr  Ser  Arg  Ser
              2450                2455                2460

Ala  Cys  Gln  Arg  Gln  Lys  Lys  Val  Thr  Phe  Asp  Arg  Leu  Gln  Val  Leu
2465                2470                2475                          2480

Asp  Ser  His  Tyr  Gln  Asp  Val  Leu  Lys  Glu  Val  Lys  Ala  Ala  Ala  Ser
              2485                2490                2495

Arg  Val  Lys  Ala  Asn  Leu  Leu  Ser  Val  Glu  Glu  Ala  Cys  Ser  Leu  Thr
              2500                2505                2510

Pro  Pro  His  Ser  Ala  Lys  Ser  Lys  Phe  Gly  Tyr  Gly  Ala  Lys  Asp  Val
              2515                2520                2525

Arg  Cys  His  Ala  Arg  Lys  Ala  Val  Ala  His  Ile  Asn  Ser  Val  Trp  Lys
              2530                2535                2540

Asp  Leu  Leu  Glu  Asp  Ser  Val  Thr  Pro  Ile  Asp  Thr  Thr  Ile  Met  Ala
2545                2550                2555                          2560

Lys  Asn  Glu  Val  Phe  Cys  Val  Gln  Pro  Glu  Lys  Gly  Gly  Arg  Lys  Pro
              2565                2570                2575

Ala  Arg  Leu  Ile  Val  Phe  Pro  Asp  Leu  Gly  Val  Arg  Val  Cys  Glu  Lys
              2580                2585                2590

Met  Ala  Leu  Tyr  Asp  Val  Val  Ser  Lys  Leu  Pro  Leu  Ala  Val  Met  Gly
              2595                2600                2605

Ser  Ser  Tyr  Gly  Phe  Gln  Tyr  Ser  Pro  Gly  Gln  Arg  Val  Glu  Phe  Leu
              2610                2615                2620
```

```
Val  Gln  Ala  Trp  Lys  Ser  Lys  Lys  Thr  Pro  Met  Gly  Phe  Ser  Tyr  Asp
2625                2630                2635                          2640

Thr  Arg  Cys  Phe  Asp  Ser  Thr  Val  Thr  Glu  Ser  Asp  Ile  Arg  Thr  Glu
               2645                2650                          2655

Glu  Ala  Ile  Tyr  Gln  Cys  Cys  Asp  Leu  Asp  Pro  Gln  Ala  Arg  Val  Ala
               2660                2665                          2670

Ile  Lys  Ser  Leu  Thr  Glu  Arg  Leu  Tyr  Val  Gly  Gly  Pro  Leu  Thr  Asn
               2675                2680                          2685

Ser  Arg  Gly  Glu  Asn  Cys  Gly  Tyr  Arg  Arg  Cys  Arg  Ala  Ser  Gly  Val
               2690                2695                          2700

Leu  Thr  Thr  Ser  Cys  Gly  Asn  Thr  Leu  Thr  Cys  Tyr  Ile  Lys  Ala  Arg
2705                2710                2715                          2720

Ala  Ala  Cys  Arg  Ala  Ala  Gly  Leu  Gln  Asp  Arg  Thr  Met  Leu  Val  Cys
               2725                2730                          2735

Gly  Asp  Asp  Leu  Val  Val  Ile  Cys  Glu  Ser  Ala  Gly  Val  Gln  Glu  Asp
               2740                2745                          2750

Ala  Ala  Ser  Leu  Arg  Ala  Phe  Thr  Glu  Ala  Met  Thr  Arg  Tyr  Ser  Ala
               2755                2760                          2765

Pro  Pro  Gly  Asp  Pro  Pro  Gln  Pro  Glu  Tyr  Asp  Leu  Glu  Leu  Ile  Thr
2770                2775                2780

Ser  Cys  Ser  Ser  Asn  Val  Ser  Val  Ala  His  Asp  Gly  Ala  Gly  Lys  Arg
2785                2790                2795                          2800

Val  Tyr  Tyr  Leu  Thr  Arg  Asp  Pro  Thr  Thr  Pro  Leu  Ala  Arg  Ala  Ala
               2805                2810                          2815

Trp  Glu  Thr  Ala  Arg  His  Thr  Pro  Val  Asn  Ser  Trp  Leu  Gly  Asn  Ile
               2820                2825                          2830

Ile  Met  Phe  Ala  Pro  Thr  Leu  Trp  Ala  Arg  Met  Ile  Leu  Met  Thr  His
               2835                2840                          2845

Phe  Phe  Ser  Val  Leu  Ile  Ala  Arg  Asp  Gln  Phe  Glu  Gln  Ala  Leu  Asn
               2850                2855                          2860

Cys  Glu  Ile  Tyr  Gly  Ala  Cys  Tyr  Ser  Ile  Glu  Pro  Leu  Asp  Leu  Pro
2865                2870                2875                          2880

Pro  Ile  Ile  Gln  Arg  Leu  His  Gly  Leu  Ser  Ala  Phe  Ser  Leu  His  Ser
               2885                2890                          2895

Tyr  Ser  Pro  Gly  Glu  Ile  Asn  Arg  Val  Ala  Ala  Cys  Leu  Arg  Lys  Leu
               2900                2905                          2910

Gly  Val  Pro  Pro  Leu  Arg  Ala  Trp  Lys  His  Arg  Ala  Arg  Ser  Val  Arg
               2915                2920                          2925

Ala  Arg  Leu  Leu  Ser  Arg  Gly  Gly  Arg  Ala  Ala  Ile  Cys  Gly  Lys  Tyr
               2930                2935                          2940

Leu  Phe  Asn  Trp  Ala  Val  Arg  Thr  Lys  Pro  Lys  Leu  Thr  Pro  Ile  Ala
2945                2950                2955                          2960

Ala  Ala  Gly  Arg  Leu  Asp  Leu  Ser  Gly  Trp  Phe  Thr  Ala  Gly  Tyr  Ser
               2965                2970                          2975

Gly  Gly  Asp  Ile  Tyr  His  Ser  Val  Ser  His  Ala  Arg  Pro  Arg  Trp  Ser
               2980                2985                          2990

Trp  Phe  Cys  Leu  Leu  Leu  Leu  Ala  Ala  Gly  Val  Gly  Ile  Tyr  Leu  Leu
               2995                3000                          3005

Pro  Asn  Arg
3010
```

( 2 ) INFORMATION FOR SEQ ID NO:2:

( i ) SEQUENCE CHARACTERISTICS:

5,610,009

31

32

-continued ( A ) LENGTH: 221 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

| Met<br>1 | Leu | Pro | Gly | Leu<br>5 | Ala | Leu | Leu | Leu | Ala<br>10 | Ala | Trp | Thr | Ala | Arg<br>15 |
|---|---|---|---|---|---|---|---|---|---|---|---|---|---|---|
| Ala | Leu | Glu | Val<br>20 | Pro | Ser | Ser | Asn | Ser<br>25 | Asp | Pro | Tyr | Gln | Val<br>30 | Arg | Asn |
| Ser | Ser | Gly<br>35 | Leu | Tyr | His | Val | Thr<br>40 | Asn | Asp | Cys | Pro | Asn<br>45 | Ser | Ser | Ile |
| Val | Tyr<br>50 | Glu | Ala | Ala | Asp | Ala<br>55 | Ile | Leu | His | Thr | Pro<br>60 | Gly | Cys | Val | Pro |
| Cys<br>65 | Val | Arg | Glu | Gly | Asn<br>70 | Ala | Ser | Arg | Cys | Trp<br>75 | Val | Ala | Val | Thr | Pro<br>80 |
| Thr | Val | Ala | Thr | Arg<br>85 | Asp | Gly | Lys | Leu | Pro<br>90 | Thr | Thr | Gln | Leu | Arg<br>95 | Arg |
| His | Ile | Asp | Leu<br>100 | Leu | Val | Gly | Ser | Ala<br>105 | Thr | Leu | Cys | Ser | Ala<br>110 | Leu | Tyr |
| Val | Gly | Asp<br>115 | Leu | Cys | Gly | Ser | Val<br>120 | Phe | Leu | Val | Gly | Gln<br>125 | Leu | Phe | Thr |
| Phe | Ser<br>130 | Pro | Arg | Arg | His | Trp<br>135 | Thr | Thr | Gln | Asp | Cys<br>140 | Asn | Cys | Ser | Ile |
| Tyr<br>145 | Pro | Gly | His | Ile | Thr<br>150 | Gly | His | Arg | Met | Ala<br>155 | Trp | Asp | Met | Met | Met<br>160 |
| Asn | Trp | Ser | Pro | Thr<br>165 | Ala | Ala | Leu | Val | Val<br>170 | Ala | Gln | Leu | Leu | Arg<br>175 | Ile |
| Pro | Gln | Ala | Ile<br>180 | Leu | Asp | Met | Ile | Ala<br>185 | Gly | Ala | His | Trp | Gly<br>190 | Val | Leu |
| Ala | Gly | Ile<br>195 | Ala | Tyr | Phe | Ser | Met<br>200 | Val | Gly | Asn | Trp | Ala<br>205 | Lys | Val | Leu |
| Val | Val<br>210 | Leu | Leu | Leu | Phe | Ala<br>215 | Gly | Val | Asp | Ala | Glu<br>220 | Ile | | | |

( 2 ) INFORMATION FOR SEQ ID NO:3:

( i ) SEQUENCE CHARACTERISTICS:
( A ) LENGTH: 4810 base pairs
( B ) TYPE: nucleic acid
( C ) STRANDEDNESS: single
( D ) TOPOLOGY: circular ( i i ) MOLECULE TYPE: DNA (genomic)

( i x ) FEATURE:
( A ) NAME/KEY: CDS
( B ) LOCATION: 2227..2910

( x i ) SEQUENCE DESCRIPTION: SEQ ID NO:3:

| GCGTAATCTG | CTGCTTGCAA | ACAAAAAAAC | CACCGCTACC | AGCGGTGGTT | TGTTTGCCGG | 60 |
| ATCAAGAGCT | ACCAACTCTT | TTTCCGAAGG | TAACTGGCTT | CAGCAGAGCG | CAGATACCAA | 120 |
| ATACTGTCCT | TCTAGTGTAG | CCGTAGTTAG | GCCACCACTT | CAAGAACTCT | GTAGCACCGC | 180 |
| CTACATACCT | CGCTCTGCTA | ATCCTGTTAC | CAGTGGCTGC | TGCCAGTGGC | GATAAGTCGT | 240 |
| GTCTTACCGG | GTTGGACTCA | AGACGATAGT | TACCGGATAA | GGCGCAGCGG | TCGGGCTGAA | 300 |
| CGGGGGGTTC | GTGCACACAG | CCCAGCTTGG | AGCGAACGAC | CTACACCGAA | CTGAGATACC | 360 |

-continued

| | | | | | |
|---|---|---|---|---|---|
| TACAGCGTGA | GCATTGAGAA | AGCGCCACGC | TTCCCGAAGG | GAGAAAGGCG | GACAGGTATC | 420 |
| CGGTAAGCGG | CAGGGTCGGA | ACAGGAGAGC | GCACGAGGGA | GCTTCCAGGG | GGAAACGCCT | 480 |
| GGTATCTTTA | TAGTCCTGTC | GGGTTTCGCC | ACCTCTGACT | TGAGCGTCGA | TTTTTGTGAT | 540 |
| GCTCGTCAGG | GGGGCGGAGC | CTATGGAAAA | ACGCCAGCAA | CGCAAGCTAG | CTTCTAGCTA | 600 |
| GAAATTGTAA | ACGTTAATAT | TTTGTTAAAA | TTCGCGTTAA | ATTTTTGTTA | AATCAGCTCA | 660 |
| TTTTTTAACC | AATAGGCCGA | AATCGGCAAA | ATCCCTTATA | AATCAAAAGA | ATAGCCCGAG | 720 |
| ATAGGGTTGA | GTGTTGTTCC | AGTTTGGAAC | AAGAGTCCAC | TATTAAAGAA | CGTGGACTCC | 780 |
| AACGTCAAAG | GGCGAAAAAC | CGTCTATCAG | GGCGATGGCC | GCCCACTACG | TGAACCATCA | 840 |
| CCCAAATCAA | GTTTTTTGGG | GTCGAGGTGC | CGTAAAGCAC | TAAATCGGAA | CCCTAAAGGG | 900 |
| AGCCCCCGAT | TTAGAGCTTG | ACGGGGAAAG | CCGGCGAACG | TGGCGAGAAA | GGAAGGGAAG | 960 |
| AAAGCGAAAG | GAGCGGGCGC | TAGGGCGCTG | GCAAGTGTAG | CGGTCACGCT | GCGCGTAACC | 1020 |
| ACCACACCCG | CCGCGCTTAA | TGCGCCGCTA | CAGGGCGCGT | ACTATGGTTG | CTTTGACGAG | 1080 |
| ACCGTATAAC | GTGCTTTCCT | CGTTGGAATC | AGAGCGGGAG | CTAAACAGGA | GGCCGATTAA | 1140 |
| AGGGATTTTA | GACAGGAACG | GTACGCCAGC | TGGATCACCG | CGGTCTTTCT | CAACGTAACA | 1200 |
| CTTTACAGCG | GCGCGTCATT | TGATATGATG | CGCCCCGCTT | CCCGATAAGG | GAGCAGGCCA | 1260 |
| GTAAAAGCAT | TACCCGTGGT | GGGGTTCCCG | AGCGGCCAAA | GGGAGCAGAC | TCTAAATCTG | 1320 |
| CCGTCATCGA | CTTCGAAGGT | TCGAATCCTT | CCCCCACCAC | CATCACTTTC | AAAAGTCCGA | 1380 |
| AAGAATCTGC | TCCCTGCTTG | TGTGTTGGAG | GTCGCTGAGT | AGTGCGCGAG | TAAAATTTAA | 1440 |
| GCTACAACAA | GGCAAGGCTT | GACCGACAAT | TGCATGAAGA | ATCTGCTTAG | GGTTAGGCGT | 1500 |
| TTTGCGCTGC | TTCGCGATGT | ACGGGCCAGA | TATACGCGTT | GACATTGATT | ATTGACTAGT | 1560 |
| TATTAATAGT | AATCAATTAC | GGGGTCATTA | GTTCATAGCC | CATATATGGA | GTTCCGCGTT | 1620 |
| ACATAACTTA | CGGTAAATGG | CCCGCCTGGC | TGACCGCCCA | ACGACCCCCG | CCCATTGACG | 1680 |
| TCAATAATGA | CGTATGTTCC | CATAGTAACG | CCAATAGGGA | CTTTCCATTG | ACGTCAATGG | 1740 |
| GTGGACTATT | TACGGTAAAC | TGCCCACTTG | GCAGTACATC | AAGTGTATCA | TATGCCAAGT | 1800 |
| ACGCCCCCTA | TTGACGTCAA | TGACGGTAAA | TGGCCCGCCT | GGCATTATGC | CCAGTACATG | 1860 |
| ACCTTATGGG | ACTTTCCTAC | TTGGCAGTAC | ATCTACGTAT | TAGTCATCGC | TATTACCATG | 1920 |
| GTGATGCGGT | TTTGGCAGTA | CATCAATGGG | CGTGGATAGC | GGTTTGACTC | ACGGGGATTT | 1980 |
| CCAAGTCTCC | ACCCCATTGA | CGTCAATGGG | AGTTTGTTTT | GGCACCAAAA | TCAACGGGAC | 2040 |
| TTTCCAAAAT | GTCGTAACAA | CTCCGCCCCA | TTGACGCAAA | TGGGCGGTAG | GCGTGTACGG | 2100 |
| TGGGAGGTCT | ATATAAGCAG | AGCTCTCTGG | CTAACTAGAG | AACCCACTGC | TTAACTGGCT | 2160 |
| TATCGAAATT | AATACGACTC | ACTATAGGGA | GACCGGAAGC | TTGGTACCGA | GCTCGGATCT | 2220 |

```
GCCACC ATG GCA ACA GGA TCA AGA ACA TCA CTG CTG CTG GCA TTT GGA          2268
       Met Ala Thr Gly Ser Arg Thr Ser Leu Leu Leu Ala Phe Gly
         1           5                  10

CTG CTG TGT CTG CCA TGG CTG CAA GAA GGA TCA GCA GCA GCA GCA GCG          2316
Leu Leu Cys Leu Pro Trp Leu Gln Glu Gly Ser Ala Ala Ala Ala Ala
 15                  20                  25                  30

AAT TCG GAT CCC TAC CAA GTG CGC AAT TCC TCG GGG CTT TAC CAT GTC          2364
Asn Ser Asp Pro Tyr Gln Val Arg Asn Ser Ser Gly Leu Tyr His Val
                     35                  40                  45

ACC AAT GAT TGC CCT AAT TCG AGT ATT GTG TAC GAG GCG GCC GAT GCC          2412
Thr Asn Asp Cys Pro Asn Ser Ser Ile Val Tyr Glu Ala Ala Asp Ala
             50                  55                  60
```

| | | | | | | | | | | | | | | | | |
|---|---|---|---|---|---|---|---|---|---|---|---|---|---|---|---|---|
| ATC | CTA | CAC | ACT | CCG | GGG | TGT | GTC | CCT | TGC | GTT | CGC | GAG | GGT | AAC | GCC | 2460 |
| Ile | Leu | His 65 | Thr | Pro | Gly | Cys | Val 70 | Pro | Cys | Val | Arg | Glu 75 | Gly | Asn | Ala | |
| TCG | AGG | TGT | TGG | GTG | GCG | GTG | ACC | CCC | ACG | GTG | GCC | ACC | AGG | GAC | GGC | 2508 |
| Ser | Arg 80 | Cys | Trp | Val | Ala | Val 85 | Thr | Pro | Thr | Val | Ala 90 | Thr | Arg | Asp | Gly | |
| AAA | CTC | CCC | ACA | ACG | CAG | CTT | CGA | CGT | CAT | ATC | GAT | CTG | CTC | GTC | GGG | 2556 |
| Lys 95 | Leu | Pro | Thr | Thr | Gln 100 | Leu | Arg | Arg | His | Ile 105 | Asp | Leu | Leu | Val | Gly 110 | |
| AGC | GCC | ACC | CTC | TGC | TCG | GCC | CTC | TAC | GTG | GGG | GAC | CTG | TGC | GGG | TCT | 2604 |
| Ser | Ala | Thr | Leu | Cys 115 | Ser | Ala | Leu | Tyr | Val 120 | Gly | Asp | Leu | Cys | Gly 125 | Ser | |
| GTC | TTT | CTT | GTT | GGT | CAA | CTG | TTT | ACC | TTC | TCT | CCC | AGG | CGC | CAC | TGG | 2652 |
| Val | Phe | Leu | Val 130 | Gly | Gln | Leu | Phe | Thr 135 | Phe | Ser | Pro | Arg | Arg 140 | His | Trp | |
| ACG | ACG | CAA | GAC | TGC | AAT | TGT | TCT | ATC | TAT | CCC | GGC | CAT | ATA | ACG | GGT | 2700 |
| Thr | Thr | Gln | Asp | Cys 145 | Asn | Cys | Ser | Ile | Tyr 150 | Pro | Gly | His | Ile | Thr 155 | Gly | |
| CAT | CGT | ATG | GCA | TGG | GAT | ATG | ATG | ATG | AAC | TGG | TCC | CCT | ACG | GCA | GCG | 2748 |
| His | Arg | Met 160 | Ala | Trp | Asp | Met | Met 165 | Met | Asn | Trp | Ser | Pro 170 | Thr | Ala | Ala | |
| TTG | GTG | GTA | GCT | CAG | CTG | CTC | CGG | ATC | CCA | CAA | GCC | ATC | TTG | GAC | ATG | 2796 |
| Leu 175 | Val | Val | Ala | Gln | Leu 180 | Leu | Arg | Ile | Pro | Gln 185 | Ala | Ile | Leu | Asp | Met 190 | |
| ATC | GCT | GGT | GCC | CAC | TGG | GGA | GTC | CTG | GCG | GGC | ATA | GCG | TAT | TTC | TCC | 2844 |
| Ile | Ala | Gly | Ala | His 195 | Trp | Gly | Val | Leu | Ala 200 | Gly | Ile | Ala | Tyr | Phe 205 | Ser | |
| ATG | GTG | GGG | AAC | TGG | GCG | AAG | GTC | CTG | GTA | GTG | CTG | CTG | CTA | TTT | GCC | 2892 |
| Met | Val | Gly | Asn 210 | Trp | Ala | Lys | Val | Leu 215 | Val | Val | Leu | Leu | Leu 220 | Phe | Ala | |
| GGC | GTT | GAC | GCG | GAG | ATC | TAATCTAGAG | GGCCCTATTC | TATAGTGTCA | | | | | | | | 2940 |
| Gly | Val | Asp | Ala | Glu 225 | Ile | | | | | | | | | | | |

| | | | | | |
|---|---|---|---|---|---|
| CCTAAATGCT | AGAGGATCTT | TGTGAAGGAA | CCTTACTTCT | GTGGTGTGAC | ATAATTGGAC | 3000 |
| AAACTACCTA | CAGAGATTTA | AAGCTCTAAG | GTAAATATAA | AATTTTTAAG | TGTATAATGT | 3060 |
| GTTAAACTAC | TGATTCTAAT | TGTTTGTGTA | TTTTAGATTC | CAACCTATGG | AACTGATGAA | 3120 |
| TGGGAGCAGT | GGTGGAATGC | CTTTAATGAG | GAAAACCTGT | TTTGCTCAGA | AGAAATGCCA | 3180 |
| TCTAGTGATG | ATGAGGCTAC | TGCTGACTCT | CAACATTCTA | CTCCTCCAAA | AAGAAGAGA | 3240 |
| AAGGTAGAAG | ACCCCAAGGA | CTTTCCTTCA | GAATTGCTAA | GTTTTTGAG | TCATGCTGTG | 3300 |
| TTTAGTAATA | GAACTCTTGC | TTGCTTTGCT | ATTTACACCA | CAAAGGAAAA | AGCTGCACTG | 3360 |
| CTATACAAGA | AAATTATGGA | AAAATATTCT | GTAACCTTTA | TAAGTAGGCA | TAACAGTTAT | 3420 |
| AATCATAACA | TACTGTTTTT | TCTTACTCCA | CACAGGCATA | GAGTGTCTGC | TATTAATAAC | 3480 |
| TATGCTCAAA | AATTGTGTAC | CTTTAGCTTT | TTAATTTGTA | AAGGGGTTAA | TAAGGAATAT | 3540 |
| TTGATGTATA | GTGCCTTGAC | TAGAGATCAT | AATCAGCCAT | ACCACATTTG | TAGAGGTTTT | 3600 |
| ACTTGCTTTA | AAAAACCTCC | CACACCTCCC | CCTGAACCTG | AAACATAAAA | TGAATGCAAT | 3660 |
| TGTTGTTGTT | AACTTGTTTA | TTGCAGCTTA | TAATGGTTAC | AAATAAAGCA | ATAGCATCAC | 3720 |
| AAATTTCACA | AATAAAGCAT | TTTTTTCACT | GCATTCTAGT | TGTGGTTTGT | CCAAACTCAT | 3780 |
| CAATGTATCT | TATCATGTCT | GGATCGATCC | CGCCATGGTA | TCAACGCCAT | ATTTCTATTT | 3840 |
| ACAGTAGGGA | CCTCTTCGTT | GTGTAGGTAC | CGCTGTATTC | CTAGGGAAAT | AGTAGAGGCA | 3900 |
| CCTTGAACTG | TCTGCATCAG | CCATATAGCC | CCCGCTGTTC | GACTTACAAA | CACAGGCACA | 3960 |
| GTACTGACAA | ACCCATACAC | CTCCTCTGAA | ATACCCATAG | TTGCTAGGGC | TGTCTCCGAA | 4020 |

-continued

| | | | | | |
|---|---|---|---|---|---|
| CTCATTACAC | CCTCCAAAGT | CAGAGCTGTA | ATTTCGCCAT | CAAGGGCAGC | GAGGGCTTCT | 4080
| CCAGATAAAA | TAGCTTCTGC | CGAGAGTCCC | GTAAGGGTAG | ACACTTCAGC | TAATCCCTCG | 4140
| ATGAGGTCTA | CTAGAATAGT | CAGTGCGGCT | CCCATTTTGA | AAATTCACTT | ACTTGATCAG | 4200
| CTTCAGAAGA | TGGCGGAGGG | CCTCCAACAC | AGTAATTTTC | CTCCCGACTC | TTAAAATAGA | 4260
| AAATGTCAAG | TCAGTTAAGC | AGGAAGTGGA | CTAACTGACG | CAGCTGGCCG | TGCGACATCC | 4320
| TCTTTTAATT | AGTTGCTAGG | CAACGCCCTC | CAGAGGGCGT | GTGGTTTTGC | AAGAGGAAGC | 4380
| AAAAGCCTCT | CCACCCAGGC | CTAGAATGTT | TCCACCCAAT | CATTACTATG | ACAACAGCTG | 4440
| TTTTTTTTAG | TATTAAGCAG | AGGCCGGGGA | CCCCTGGCCC | GCTTACTCTG | GAGAAAAAGA | 4500
| AGAGAGGCAT | TGTAGAGGCT | TCCAGAGGCA | ACTTGTCAAA | ACAGGACTGC | TTCTATTTCT | 4560
| GTCACACTGT | CTGGCCCTGT | CACAAGGTCC | AGCACCTCCA | TACCCCTTT | AATAAGCAGT | 4620
| TTGGGAACGG | GTGCGGGTCT | TACTCCGCCC | ATCCCGCCCC | TAACTCCGCC | CAGTTCCGCC | 4680
| CATTCTCCGC | CCCATGGCTG | ACTAATTTTT | TTTATTTATG | CAGAGGCCGA | GGCCGCCTCG | 4740
| GCCTCTGAGC | TATTCCAGAA | GTAGTGAGGA | GGCTTTTTG | GAGGCCTAGG | CTTTTGCAAA | 4800
| AAGCTAATTC | | | | | | 4810

( 2 ) INFORMATION FOR SEQ ID NO:4:

( i ) SEQUENCE CHARACTERISTICS:
( A ) LENGTH: 228 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Ala Ala Ala Ala Asn Ser
            20                  25                  30

Asp Pro Tyr Gln Val Arg Asn Ser Ser Gly Leu Tyr His Val Thr Asn
        35                  40                  45

Asp Cys Pro Asn Ser Ser Ile Val Tyr Glu Ala Ala Asp Ala Ile Leu
    50                  55                  60

His Thr Pro Gly Cys Val Pro Cys Val Arg Glu Gly Asn Ala Ser Arg
65                  70                  75                  80

Cys Trp Val Ala Val Thr Pro Thr Val Ala Thr Arg Asp Gly Lys Leu
                85                  90                  95

Pro Thr Thr Gln Leu Arg Arg His Ile Asp Leu Leu Val Gly Ser Ala
            100                 105                 110

Thr Leu Cys Ser Ala Leu Tyr Val Gly Asp Leu Cys Gly Ser Val Phe
        115                 120                 125

Leu Val Gly Gln Leu Phe Thr Phe Ser Pro Arg Arg His Trp Thr Thr
130                 135                 140                 145

Gln Asp Cys Asn Cys Ser Ile Tyr Pro Gly His Ile Thr Gly His Arg
                150                 155                 160

Met Ala Trp Asp Met Met Met Asn Trp Ser Pro Thr Ala Ala Leu Val
            165                 170                 175

Val Ala Gln Leu Leu Arg Ile Pro Gln Ala Ile Leu Asp Met Ile Ala
        180                 185                 190

Gly Ala His Trp Gly Val Leu Ala Gly Ile Ala Tyr Phe Ser Met Val
    195                 200                 205
```

```
Gly  Asn  Trp  Ala  Lys  Val  Leu  Val  Val  Leu  Leu  Leu  Phe  Ala  Gly  Val
210            215                      220                           225

Asp  Ala  Glu  Ile
```

(2) INFORMATION FOR SEQ ID NO:5:

(i) SEQUENCE CHARACTERISTICS:
        (A) LENGTH: 172 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met  Leu  Pro  Gly  Leu  Ala  Leu  Leu  Leu  Ala  Ala  Trp  Thr  Ala  Arg
1              5                        10                       15

Ala  Leu  Glu  Val  Pro  Ser  Ser  Asn  Ser  Asp  Pro  Tyr  Gln  Val  Arg  Asn
               20                      25                      30

Ser  Ser  Gly  Leu  Tyr  His  Val  Thr  Asn  Asp  Cys  Pro  Asn  Ser  Ser  Ile
          35                      40                      45

Val  Tyr  Glu  Ala  Ala  Asp  Ala  Ile  Leu  His  Thr  Pro  Gly  Cys  Val  Pro
     50                      55                      60

Cys  Val  Arg  Glu  Gly  Asn  Ala  Ser  Arg  Cys  Trp  Val  Ala  Val  Thr  Pro
65                       70                      75                       80

Thr  Val  Ala  Thr  Arg  Asp  Gly  Lys  Leu  Pro  Thr  Thr  Gln  Leu  Arg  Arg
                    85                      90                       95

His  Ile  Asp  Leu  Leu  Val  Gly  Ser  Ala  Thr  Leu  Cys  Ser  Ala  Leu  Tyr
               100                      105                     110

Val  Gly  Asp  Leu  Cys  Gly  Ser  Val  Phe  Leu  Val  Gly  Gln  Leu  Phe  Thr
          115                      120                     125

Phe  Ser  Pro  Arg  Arg  His  Trp  Thr  Thr  Gln  Asp  Cys  Asn  Cys  Ser  Ile
     130                     135                     140

Tyr  Pro  Gly  His  Ile  Thr  Gly  His  Arg  Met  Ala  Trp  Asp  Met  Met  Met
145                      150                     155                      160

Asn  Trp  Ser  Pro  Thr  Ala  Ala  Leu  Val  Val  Ala  Gln
                    165                     170
```

(2) INFORMATION FOR SEQ ID NO:6:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met  Leu  Pro  Gly  Leu  Ala  Leu  Leu  Leu  Ala  Ala  Trp  Thr  Ala  Arg
1              5                        10                       15

Ala  Leu  Glu  Val  Pro  Ser  Ser  Asn  Ser  Asp  Pro  Tyr  Gln  Val  Arg  Asn
               20                      25                      30

Ser  Ser  Gly  Leu  Tyr  His  Val  Thr  Asn  Asp  Cys  Pro  Asn  Ser  Ser  Ile
          35                      40                      45

Val  Tyr  Glu  Ala  Ala  Asp  Ala  Ile  Leu  His  Thr  Pro  Gly  Cys  Val  Pro
     50                      55                      60

Cys  Val  Arg  Glu  Gly  Asn  Ala  Ser  Arg  Cys  Trp  Val  Ala  Val  Thr  Pro
65                       70                      75                       80
```

| Thr | Val | Ala | Thr | Arg | Asp | Gly | Lys | Leu | Pro | Thr | Thr | Gln | Leu | Arg | Arg |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| His | Trp | Thr | Thr | Gln | Asp | Cys | Asn | Cys | Ser | Ile | Tyr | Pro | Gly | His | Ile |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Gly | His | Arg | Met | Ala | Trp | Asp | Met | Met | Met | Asn | Trp | Ser | Pro | Thr |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ala | Ala | Leu | Val | Val | Ala | Gln |
|-----|-----|-----|-----|-----|-----|-----|
| 130 |     |     |     |     |     | 135 |

(2) INFORMATION FOR SEQ ID NO:7:

(i) SEQUENCE CHARACTERISTICS:
        (A) LENGTH:337 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

| Met | Leu | Pro | Gly | Leu | Ala | Leu | Leu | Leu | Leu | Ala | Ala | Trp | Thr | Ala | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Leu | Glu | Val | Pro | Thr | Asp | Gly | Asn | Ala | Gly | Leu | Leu | Ala | Glu | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Ile | Ala | Met | Phe | Cys | Gly | Arg | Leu | Asn | Met | His | Met | Asn | Val | Gln |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Asn | Gly | Lys | Trp | Asp | Ser | Asp | Pro | Ser | Gly | Thr | Lys | Thr | Cys | Ile | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Lys | Glu | Thr | His | Val | Thr | Gly | Gly | Ser | Ala | Gly | His | Thr | Thr | Ala |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gly | Leu | Val | Arg | Leu | Leu | Ser | Pro | Gly | Ala | Lys | Gln | Asn | Ile | Gln | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ile | Asn | Thr | Asn | Gly | Ser | Trp | His | Ile | Asn | Ser | Thr | Ala | Leu | Asn | Cys |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Asn | Glu | Ser | Leu | Asn | Thr | Gly | Trp | Leu | Ala | Gly | Leu | Phe | Tyr | His | His |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Lys | Phe | Asn | Ser | Ser | Gly | Cys | Pro | Glu | Arg | Leu | Ala | Ser | Cys | Arg | Arg |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Leu | Thr | Asp | Phe | Ala | Gln | Gly | Gly | Gly | Pro | Ile | Ser | Tyr | Ala | Asn | Gly |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ser | Gly | Leu | Asp | Glu | Arg | Pro | Tyr | Cys | Trp | His | Tyr | Pro | Pro | Arg | Pro |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Cys | Gly | Ile | Val | Pro | Ala | Lys | Ser | Val | Cys | Gly | Pro | Val | Tyr | Cys | Phe |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Thr | Pro | Ser | Pro | Val | Val | Val | Gly | Thr | Thr | Asp | Arg | Ser | Gly | Ala | Pro |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Thr | Tyr | Ser | Trp | Gly | Ala | Asn | Asp | Thr | Asp | Val | Phe | Val | Leu | Asn | Asn |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Thr | Arg | Pro | Pro | Leu | Gly | Asn | Trp | Phe | Gly | Cys | Thr | Trp | Met | Asn | Ser |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Thr | Gly | Phe | Thr | Lys | Val | Cys | Gly | Ala | Pro | Pro | Cys | Val | Ile | Gly | Gly |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Val | Gly | Asn | Asn | Thr | Leu | Leu | Cys | Pro | Thr | Asp | Cys | Phe | Arg | Lys | His |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Pro | Glu | Ala | Thr | Tyr | Ser | Arg | Cys | Gly | Ser | Gly | Pro | Trp | Ile | Thr | Pro |
|-----|-----|-----|-----|-----|-----|-----|-----|-----|-----|-----|-----|-----|-----|-----|-----|
|     |     |     | 275 |     |     |     |     | 280 |     |     |     |     | 285 |     |     |

```
    Arg  Cys  Met  Val  Asp  Tyr  Pro  Tyr  Arg  Leu  Trp  His  Tyr  Pro  Cys  Thr
         290                      295                      300

Ile  Asn  Tyr  Thr  Ile  Phe  Lys  Val  Arg  Met  Tyr  Val  Gly  Gly  Val  Glu
    305                      310                      315                      320

His  Arg  Leu  Glu  Ala  Ala  Cys  Asn  Trp  Thr  Arg  Gly  Glu  Arg  Cys  Asp
                        325                      330                      335

Leu
```

( 2 ) INFORMATION FOR SEQ ID NO:8:

( i ) SEQUENCE CHARACTERISTICS:
        ( A ) LENGTH: 7106 base pairs
        ( B ) TYPE: nucleic acid
        ( C ) STRANDEDNESS: single
        ( D ) TOPOLOGY: circular ( i i ) MOLECULE TYPE: DNA (genomic)

( i x ) FEATURE:
        ( A ) NAME/KEY: CDS
        ( B ) LOCATION: 922..2022

( x i ) SEQUENCE DESCRIPTION: SEQ ID NO:8:

```
GACGGATCGG  GAGATCTCCC  GATCCCCTAT  GGTCGACTCT  CAGTACAATC  TGCTCTGATG      60
CCGCATAGTT  AAGCCAGTAT  CTGCTCCCTG  CTTGTGTGTT  GGAGGTCGCT  GAGTAGTGCG     120
CGAGCAAAAT  TTAAGCTACA  ACAAGGCAAG  GCTTGACCGA  CAATTGCATG  AAGAATCTGC     180
TTAGGGTTAG  GCGTTTTGCG  CTGCTTCGCG  ATGTACGGGC  CAGATATACG  CGTTGACATT     240
GATTATTGAC  TAGTTATTAA  TAGTAATCAA  TTACGGGGTC  ATTAGTTCAT  AGCCCATATA     300
TGGAGTTCCG  CGTTACATAA  CTTACGGTAA  ATGGCCCGCC  TGGCTGACCG  CCCAACGACC     360
CCCGCCCATT  GACGTCAATA  ATGACGTATG  TTCCCATAGT  AACGCCAATA  GGGACTTTCC     420
ATTGACGTCA  ATGGGTGGAC  TATTTACGGT  AAACTGCCCA  CTTGGCAGTA  CATCAAGTGT     480
ATCATATGCC  AAGTACGCCC  CCTATTGACG  TCAATGACGG  TAAATGGCCC  GCCTGGCATT     540
ATGCCCAGTA  CATGACCTTA  TGGGACTTTC  CTACTTGGCA  GTACATCTAC  GTATTAGTCA     600
TCGCTATTAC  CATGGTGATG  CGGTTTTGGC  AGTACATCAA  TGGGCGTGGA  TAGCGGTTTG     660
ACTCACGGGG  ATTTCCAAGT  CTCCACCCCA  TTGACGTCAA  TGGGAGTTTG  TTTTGGCACC     720
AAAATCAACG  GGACTTTCCA  AAATGTCGTA  ACAACTCCGC  CCCATTGACG  CAAATGGGCG     780
GTAGGCGTGT  ACGGTGGGAG  GTCTATATAA  GCAGAGCTCT  CTGGCTAACT  AGAGAACCCA     840
CTGCTTAACT  GGCTTATCGA  AATTAATACG  ACTCACTATA  GGGAGACCGG  AAGCTTTGCT     900
CTAGACTGGA  ATTCGGGCGC  G ATG CTG CCC GGT TTG GCA CTG CTC CTG CTG          951
            Met Leu Pro Gly Leu Ala Leu Leu Leu Leu
              1               5                  10

GCC GCC TGG ACG GCT CGG GCG CTG GAG GTA CCC ACT GAT GGT AAT GCT           999
Ala Ala Trp Thr Ala Arg Ala Leu Glu Val Pro Thr Asp Gly Asn Ala
                  15                   20                  25

GGC CTG CTG GCT GAA CCC CAG ATT GCC ATG TTC TGT GGC AGA CTG AAC          1047
Gly Leu Leu Ala Glu Pro Gln Ile Ala Met Phe Cys Gly Arg Leu Asn
              30                  35                  40

ATG CAC ATG AAT GTC CAG AAT GGG AAG TGG GAT TCA GAT CCA TCA GGG          1095
Met His Met Asn Val Gln Asn Gly Lys Trp Asp Ser Asp Pro Ser Gly
          45                   50                  55

ACC AAA ACC TGC ATT GAT ACC AAG GAA ACC CAC GTC ACC GGG GGA AGT          1143
Thr Lys Thr Cys Ile Asp Thr Lys Glu Thr His Val Thr Gly Gly Ser
      60                  65                  70
```

| | | | | | | | | | | | | | | | | |
|---|---|---|---|---|---|---|---|---|---|---|---|---|---|---|---|---|
| GCC | GGC | CAC | ACC | ACG | GCT | GGG | CTT | GTT | CGT | CTC | CTT | TCA | CCA | GGC | GCC | 1191 |
| Ala 75 | Gly | His | Thr | Thr | Ala 80 | Gly | Leu | Val | Arg | Leu 85 | Leu | Ser | Pro | Gly | Ala 90 | |
| AAG | CAG | AAC | ATC | CAA | CTG | ATC | AAC | ACC | AAC | GGC | AGT | TGG | CAC | ATC | AAT | 1239 |
| Lys | Gln | Asn | Ile | Gln 95 | Leu | Ile | Asn | Thr | Asn 100 | Gly | Ser | Trp | His | Ile 105 | Asn | |
| AGC | ACG | GCC | TTG | AAC | TGC | AAT | GAA | AGC | CTT | AAC | ACC | GGC | TGG | TTA | GCA | 1287 |
| Ser | Thr | Ala | Leu 110 | Asn | Cys | Asn | Glu | Ser 115 | Leu | Asn | Thr | Gly | Trp 120 | Leu | Ala | |
| GGG | CTC | TTC | TAT | CAC | CAC | AAA | TTC | AAC | TCT | TCA | GGT | TGT | CCT | GAG | AGG | 1335 |
| Gly | Leu | Phe 125 | Tyr | His | His | Lys | Phe 130 | Asn | Ser | Ser | Gly | Cys 135 | Pro | Glu | Arg | |
| TTG | GCC | AGC | TGC | CGA | CGC | CTT | ACC | GAT | TTT | GCC | CAG | GGC | GGG | GGT | CCT | 1383 |
| Leu | Ala 140 | Ser | Cys | Arg | Arg | Leu 145 | Thr | Asp | Phe | Ala | Gln 150 | Gly | Gly | Gly | Pro | |
| ATC | AGT | TAC | GCC | AAC | GGA | AGC | GGC | CTC | GAT | GAA | CGC | CCC | TAC | TGC | TGG | 1431 |
| Ile 155 | Ser | Tyr | Ala | Asn | Gly 160 | Ser | Gly | Leu | Asp | Glu 165 | Arg | Pro | Tyr | Cys | Trp 170 | |
| CAC | TAC | CCT | CCA | AGA | CCT | TGT | GGC | ATT | GTG | CCC | GCA | AAG | AGC | GTG | TGT | 1479 |
| His | Tyr | Pro | Pro | Arg 175 | Pro | Cys | Gly | Ile | Val 180 | Pro | Ala | Lys | Ser | Val 185 | Cys | |
| GGC | CCG | GTA | TAT | TGC | TTC | ACT | CCC | AGC | CCC | GTG | GTG | GTG | GGA | ACG | ACC | 1527 |
| Gly | Pro | Val | Tyr 190 | Cys | Phe | Thr | Pro | Ser 195 | Pro | Val | Val | Val | Gly 200 | Thr | Thr | |
| GAC | AGG | TCG | GGC | GCG | CCT | ACC | TAC | AGC | TGG | GGT | GCA | AAT | GAT | ACG | GAT | 1575 |
| Asp | Arg | Ser 205 | Gly | Ala | Pro | Thr | Tyr 210 | Ser | Trp | Gly | Ala | Asn 215 | Asp | Thr | Asp | |
| GTC | TTT | GTC | CTT | AAC | AAC | ACC | AGG | CCA | CCG | CTG | GGC | AAT | TGG | TTC | GGT | 1623 |
| Val | Phe 220 | Val | Leu | Asn | Asn | Thr 225 | Arg | Pro | Pro | Leu | Gly 230 | Asn | Trp | Phe | Gly | |
| TGC | ACC | TGG | ATG | AAC | TCA | ACT | GGA | TTC | ACC | AAA | GTG | TGC | GGA | GCG | CCC | 1671 |
| Cys 235 | Thr | Trp | Met | Asn | Ser 240 | Thr | Gly | Phe | Thr | Lys 245 | Val | Cys | Gly | Ala | Pro 250 | |
| CCT | TGT | GTC | ATC | GGA | GGG | GTG | GGC | AAC | AAC | ACC | TTG | CTC | TGC | CCC | ACT | 1719 |
| Pro | Cys | Val | Ile | Gly 255 | Gly | Val | Gly | Asn | Asn 260 | Thr | Leu | Leu | Cys | Pro 265 | Thr | |
| GAT | TGC | TTC | CGC | AAG | CAT | CCG | GAA | GCC | ACA | TAC | TCT | CGG | TGC | GGC | TCC | 1767 |
| Asp | Cys | Phe | Arg 270 | Lys | His | Pro | Glu | Ala 275 | Thr | Tyr | Ser | Arg | Cys 280 | Gly | Ser | |
| GGT | CCC | TGG | ATT | ACA | CCC | AGG | TGC | ATG | GTC | GAC | TAC | CCG | TAT | AGG | CTT | 1815 |
| Gly | Pro | Trp 285 | Ile | Thr | Pro | Arg | Cys 290 | Met | Val | Asp | Tyr | Pro 295 | Tyr | Arg | Leu | |
| TGG | CAC | TAT | CCT | TGT | ACC | ATC | AAT | TAC | ACC | ATA | TTC | AAA | GTC | AGG | ATG | 1863 |
| Trp | His 300 | Tyr | Pro | Cys | Thr | Ile 305 | Asn | Tyr | Thr | Ile | Phe 310 | Lys | Val | Arg | Met | |
| TAC | GTG | GGA | GGG | GTC | GAG | CAC | AGG | CTG | GAA | GCG | GCC | TGC | AAC | TGG | ACG | 1911 |
| Tyr | Val | Gly 315 | Gly | Val | Glu | His | Arg 320 | Leu | Glu | Ala | Ala | Cys 325 | Asn | Trp | Thr 330 | |
| CGG | GGC | GAA | CGC | TGT | GAT | CTG | GAA | GAC | AGG | GAC | AGG | TCC | GAG | CTC | AGC | 1959 |
| Arg | Gly | Glu | Arg | Cys 335 | Asp | Leu | Glu | Asp | Arg 340 | Asp | Arg | Ser | Glu | Leu 345 | Ser | |
| CCG | TTA | CTG | CTG | TCC | ACC | ACG | CAG | TGG | CAG | GTC | CTT | CCG | TGT | TCT | TTC | 2007 |
| Pro | Leu | Leu | Leu 350 | Ser | Thr | Thr | Gln | Trp 355 | Gln | Val | Leu | Pro | Cys 360 | Ser | Phe | |
| ACG | ACC | CTG | CCA | GCC | TAGATCTCTG | | AAGTGAAGAT | | GGATGCAGAA | | TTCCGACATG | | | | | 2062 |
| Thr | Thr | Leu 365 | Pro | Ala | | | | | | | | | | | | |
| ACTCAGGATA | TGAAGTTCAT | CATCAAAAAT | TGGTGTTCTT | TGCAGAAGAT | GTGGGTTCAA | 2122 |
| ACAAAGGTGC | AATCATTGGA | CTCATGGTGG | GCGGTGTTGT | CATAGCGACA | GTGATCGTCA | 2182 |

| | | | | | |
|---|---|---|---|---|---|
| TCACCTTGGT | GATGCTGAAG | AAGAAACAGT | ACACATCCAT | TCATCATGGT | GTGGTGGAGG | 2242 |
| TTGACGCCGC | TGTCACCCCA | GAGGAGCGCC | ACCTGTCCAA | GATGCAGCAG | AACGGCTACG | 2302 |
| AAAATCCAAC | CTACAAGTTC | TTTGAGCAGA | TGCAGAACTA | GACCCCCGCC | ACAGCAGCCT | 2362 |
| CTGAAGTTGG | ACAGCAAAAC | CATTGCTTCA | CTACCCATCG | GTGTCCATTT | ATAGAATAAT | 2422 |
| GTGGGAAGAA | ACAAACCCGT | TTTATGATTT | ACTCATTATC | GCCTTTTGAC | AGCTGTGCTG | 2482 |
| TAACACAAGT | AGATGCCTGA | ACTTGAATTA | ATCCACACAT | CAGTAATGTA | TTCTATCTCT | 2542 |
| CTTTACATTT | TGGTCTCTAT | ACTACATTAT | TAATGGGTTT | TGTGTACTGT | AAAGAATTTA | 2602 |
| GCTGTATCAA | ACTAGTGCAT | GAATAGGCCG | CTCGAGCATG | CATCTAGAGG | GCCCTATTCT | 2662 |
| ATAGTGTCAC | CTAAATGCTC | GCTGATCAGC | CTCGACTGTG | CCTTCTAGTT | GCCAGCCATC | 2722 |
| TGTTGTTTGC | CCCTCCCCCG | TGCCTTCCTT | GACCCTGGAA | GGTGCCACTC | CCACTGTCCT | 2782 |
| TTCCTAATAA | AATGAGGAAA | TTGCATCGCA | TTGTCTGAGT | AGGTGTCATT | CTATTCTGGG | 2842 |
| GGGTGGGGTG | GGGCAGGACA | GCAAGGGGGA | GGATTGGGAA | GACAATAGCA | GGCATGCTGG | 2902 |
| GGATGCGGTG | GGCTCTATGG | AACCAGCTGG | GGCTCGAGGG | GGGATCCCCA | CGCGCCCTGT | 2962 |
| AGCGGCGCAT | TAAGCGCGGC | GGGTGTGGTG | GTTACGCGCA | GCGTGACCGC | TACACTTGCC | 3022 |
| AGCGCCCTAG | CGCCCGCTCC | TTTCGCTTTC | TTCCCTTCCT | TTCTCGCCAC | GTTCGCCGGC | 3082 |
| TTTCCCCGTC | AAGCTCTAAA | TCGGGGCATC | CCTTTAGGGT | TCCGATTTAG | TGCTTTACGG | 3142 |
| CACCTCGACC | CCAAAAAACT | TGATTAGGGT | GATGGTTCAC | GTAGTGGGCC | ATCGCCCTGA | 3202 |
| TAGACGGTTT | TTCGCCTTTA | CTGAGCACTC | TTTAATAGTG | GACTCTTGTT | CCAAACTGGA | 3262 |
| ACAACACTCA | ACCCTATCTC | GGTCTATTCT | TTTGATTTAT | AAGATTTCCA | TCGCCATGTA | 3322 |
| AAAGTGTTAC | AATTAGCATT | AAATTACTTC | TTTATATGCT | ACTATTCTTT | TGGCTTCGTT | 3382 |
| CACGGGGTGG | GTACCGAGCT | CGAATTCTGT | GGAATGTGTG | TCAGTTAGGG | TGTGGAAAGT | 3442 |
| CCCCAGGCTC | CCCAGGCAGG | CAGAAGTATG | CAAAGCATGC | ATCTCAATTA | GTCAGCAACC | 3502 |
| AGGTGTGGAA | AGTCCCCAGG | CTCCCCAGCA | GGCAGAAGTA | TGCAAAGCAT | GCATCTCAAT | 3562 |
| TAGTCAGCAA | CCATAGTCCC | GCCCCTAACT | CCGCCCATCC | CGCCCCTAAC | TCCGCCCAGT | 3622 |
| TCCGCCCATT | CTCCGCCCCA | TGGCTGACTA | ATTTTTTTTA | TTTATGCAGA | GGCCGAGGCC | 3682 |
| GCCTCGGCCT | CTGAGCTATT | CCAGAAGTAG | TGAGGAGGCT | TTTTTGGAGG | CCTAGGCTTT | 3742 |
| TGCAAAAAGC | TCCCGGGAGC | TTGGATATCC | ATTTTCGGAT | CTGATCAAGA | GACAGGATGA | 3802 |
| GGATCGTTTC | GCATGATTGA | ACAAGATGGA | TTGCACGCAG | GTTCTCCGGC | CGCTTGGGTG | 3862 |
| GAGAGGCTAT | TCGGCTATGA | CTGGGCACAA | CAGACAATCG | GCTGCTCTGA | TGCCGCCGTG | 3922 |
| TTCCGGCTGT | CAGCGCAGGG | GCGCCCGGTT | CTTTTTGTCA | AGACCGACCT | GTCCGGTGCC | 3982 |
| CTGAATGAAC | TGCAGGACGA | GGCAGCGCGG | CTATCGTGGC | TGGCCACGAC | GGGCGTTCCT | 4042 |
| TGCGCAGCTG | TGCTCGACGT | TGTCACTGAA | GCGGGAAGGG | ACTGGCTGCT | ATTGGGCGAA | 4102 |
| GTGCCGGGGC | AGGATCTCCT | GTCATCTCAC | CTTGCTCCTG | CCGAGAAAGT | ATCCATCATG | 4162 |
| GCTGATGCAA | TGCGGCGGCT | GCATACGCTT | GATCCGGCTA | CCTGCCCATT | CGACCACCAA | 4222 |
| GCGAAACATC | GCATCGAGCG | AGCACGTACT | CGGATGGAAG | CCGGTCTTGT | CGATCAGGAT | 4282 |
| GATCTGGACG | AAGAGCATCA | GGGGCTCGCG | CCAGCCGAAC | TGTTCGCCAG | GCTCAAGGCG | 4342 |
| CGCATGCCCG | ACGGCGAGGA | TCTCGTCGTG | ACCCATGGCG | ATGCCTGCTT | GCCGAATATC | 4402 |
| ATGGTGGAAA | ATGGCCGCTT | TTCTGGATTC | ATCGACTGTG | GCCGGCTGGG | TGTGGCGGAC | 4462 |
| CGCTATCAGG | ACATAGCGTT | GGCTACCCGT | GATATTGCTG | AAGAGCTTGG | CGGCGAATGG | 4522 |
| GCTGACCGCT | TCCTCGTGCT | TTACGGTATC | GCCGCTCCCG | ATTCGCAGCG | CATCGCCTTC | 4582 |

```
TATCGCCTTC  TTGACGAGTT  CTTCTGAGCG  GGACTCTGGG  GTTCGAAATG  ACCGACCAAG   4642
CGACGCCCAA  CCTGCCATCA  CGAGATTTCG  ATTCCACCGC  CGCCTTCTAT  GAAAGGTTGG   4702
GCTTCGGAAT  CGTTTTCCGG  GACGCCGGCT  GGATGATCCT  CCAGCGCGGG  GATCTCATGC   4762
TGGAGTTCTT  CGCCCACCCC  AACTTGTTTA  TTGCAGCTTA  TAATGGTTAC  AAATAAAGCA   4822
ATAGCATCAC  AAATTTCACA  AATAAAGCAT  TTTTTCACT   GCATTCTAGT  TGTGGTTTGT   4882
CCAAACTCAT  CAATGTATCT  TATCATGTCT  GGATCCCGTC  GACCTCGAGA  GCTTGGCGTA   4942
ATCATGGTCA  TAGCTGTTTC  CTGTGTGAAA  TTGTTATCCG  CTCACAATTC  CACACAACAT   5002
ACGAGCCGGA  AGCATAAAGT  GTAAAGCCTG  GGGTGCCTAA  TGAGTGAGCT  AACTCACATT   5062
AATTGCGTTG  CGCTCACTGC  CCGCTTTCCA  GTCGGGAAAC  CTGTCGTGCC  AGCTGCATTA   5122
ATGAATCGGC  CAACGCGCGG  GGAGAGGCGG  TTTGCGTATT  GGGCGCTCTT  CCGCTTCCTC   5182
GCTCACTGAC  TCGCTGCGCT  CGGTCGTTCG  GCTGCGGCGA  GCGGTATCAG  CTCACTCAAA   5242
GGCGGTAATA  CGGTTATCCA  CAGAATCAGG  GGATAACGCA  GGAAAGAACA  TGTGAGCAAA   5302
AGGCCAGCAA  AAGGCCAGGA  ACCGTAAAAA  GGCCGCGTTG  CTGGCGTTTT  TCCATAGGCT   5362
CCGCCCCCCT  GACGAGCATC  ACAAAAATCG  ACGCTCAAGT  CAGAGGTGGC  GAAACCCGAC   5422
AGGACTATAA  AGATACCAGG  CGTTTCCCCC  TGGAAGCTCC  CTCGTGCGCT  CTCCTGTTCC   5482
GACCCTGCCG  CTTACCGGAT  ACCTGTCCGC  CTTTCTCCCT  TCGGGAAGCG  TGGCGCTTTC   5542
TCAATGCTCA  CGCTGTAGGT  ATCTCAGTTC  GGTGTAGGTC  GTTCGCTCCA  AGCTGGGCTG   5602
TGTGCACGAA  CCCCCCGTTC  AGCCCGACCG  CTGCGCCTTA  TCCGGTAACT  ATCGTCTTGA   5662
GTCCAACCCG  GTAAGACACG  ACTTATCGCC  ACTGGCAGCA  GCCACTGGTA  ACAGGATTAG   5722
CAGAGCGAGG  TATGTAGGCG  GTGCTACAGA  GTTCTTGAAG  TGGTGGCCTA  ACTACGGCTA   5782
CACTAGAAGG  ACAGTATTTG  GTATCTGCGC  TCTGCTGAAG  CCAGTTACCT  TCGGAAAAAG   5842
AGTTGGTAGC  TCTTGATCCG  GCAAACAAAC  CACCGCTGGT  AGCGGTGGTT  TTTTGTTTG   5902
CAAGCAGCAG  ATTACGCGCA  GAAAAAAGG   ATCTCAAGAA  GATCCTTTGA  TCTTTTCTAC   5962
GGGGTCTGAC  GCTCAGTGGA  ACGAAAACTC  ACGTTAAGGG  ATTTTGGTCA  TGAGATTATC   6022
AAAAGGATC   TTCACCTAGA  TCCTTTTAAA  TTAAAAATGA  AGTTTTAAAT  CAATCTAAAG   6082
TATATATGAG  TAAACTTGGT  CTGACAGTTA  CCAATGCTTA  ATCAGTGAGG  CACCTATCTC   6142
AGCGATCTGT  CTATTTCGTT  CATCCATAGT  TGCCTGACTC  CCCGTCGTGT  AGATAACTAC   6202
GATACGGGAG  GGCTTACCAT  CTGGCCCCAG  TGCTGCAATG  ATACCGCGAG  ACCCACGCTC   6262
ACCGGCTCCA  GATTTATCAG  CAATAAACCA  GCCAGCCGGA  AGGGCCGAGC  GCAGAAGTGG   6322
TCCTGCAACT  TTATCCGCCT  CCATCCAGTC  TATTAATTGT  TGCCGGGAAG  CTAGAGTAAG   6382
TAGTTCGCCA  GTTAATAGTT  TGCGCAACGT  TGTTGCCATT  GCTACAGGCA  TCGTGGTGTC   6442
ACGCTCGTCG  TTTGGTATGG  CTTCATTCAG  CTCCGGTTCC  CAACGATCAA  GGCGAGTTAC   6502
ATGATCCCCC  ATGTTGTGCA  AAAAAGCGGT  TAGCTCCTTC  GGTCCTCCGA  TCGTTGTCAG   6562
AAGTAAGTTG  GCCGCAGTGT  TATCACTCAT  GGTTATGGCA  GCACTGCATA  ATTCTCTTAC   6622
TGTCATGCCA  TCCGTAAGAT  GCTTTTCTGT  GACTGGTGAG  TACTCAACCA  AGTCATTCTG   6682
AGAATAGTGT  ATGCGGCGAC  CGAGTTGCTC  TTGCCCGGCG  TCAATACGGG  ATAATACCGC   6742
GCCACATAGC  AGAACTTTAA  AAGTGCTCAT  CATTGGAAAA  CGTTCTTCGG  GGCGAAAACT   6802
CTCAAGGATC  TTACCGCTGT  TGAGATCCAG  TTCGATGTAA  CCCACTCGTG  CACCCAACTG   6862
ATCTTCAGCA  TCTTTTACTT  TCACCAGCGT  TTCTGGGTGA  GCAAAAACAG  GAAGGCAAAA   6922
TGCCGCAAAA  AAGGGAATAA  GGGCGACACG  GAAATGTTGA  ATACTCATAC  TCTTCCTTTT   6982
```

```
TCAATATTAT TGAAGCATTT ATCAGGGTTA TTGTCTCATG AGCGGATACA TATTTGAATG    7042

TATTTAGAAA AATAAACAAA TAGGGGTTCC GCGCACATTT CCCCGAAAAG TGCCACCTGA    7102

CGTC                                                                 7106
```

( 2 ) INFORMATION FOR SEQ ID NO:9:

( i ) SEQUENCE CHARACTERISTICS:
        ( A ) LENGTH: 367 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Thr His Val Thr Gly Gly Ser Ala Gly His Thr Thr Ala
65                  70                  75                  80

Gly Leu Val Arg Leu Leu Ser Pro Gly Ala Lys Gln Asn Ile Gln Leu
                85                  90                  95

Ile Asn Thr Asn Gly Ser Trp His Ile Asn Ser Thr Ala Leu Asn Cys
            100                 105                 110

Asn Glu Ser Leu Asn Thr Gly Trp Leu Ala Gly Leu Phe Tyr His His
        115                 120                 125

Lys Phe Asn Ser Ser Gly Cys Pro Glu Arg Leu Ala Ser Cys Arg Arg
    130                 135                 140

Leu Thr Asp Phe Ala Gln Gly Gly Gly Pro Ile Ser Tyr Ala Asn Gly
145                 150                 155                 160

Ser Gly Leu Asp Glu Arg Pro Tyr Cys Trp His Tyr Pro Pro Arg Pro
                165                 170                 175

Cys Gly Ile Val Pro Ala Lys Ser Val Cys Gly Pro Val Tyr Cys Phe
            180                 185                 190

Thr Pro Ser Pro Val Val Val Gly Thr Thr Asp Arg Ser Gly Ala Pro
        195                 200                 205

Thr Tyr Ser Trp Gly Ala Asn Asp Thr Asp Val Phe Val Leu Asn Asn
    210                 215                 220

Thr Arg Pro Pro Leu Gly Asn Trp Phe Gly Cys Thr Trp Met Asn Ser
225                 230                 235                 240

Thr Gly Phe Thr Lys Val Cys Gly Ala Pro Pro Cys Val Ile Gly Gly
                245                 250                 255

Val Gly Asn Asn Thr Leu Leu Cys Pro Thr Asp Cys Phe Arg Lys His
            260                 265                 270

Pro Glu Ala Thr Tyr Ser Arg Cys Gly Ser Gly Pro Trp Ile Thr Pro
        275                 280                 285

Arg Cys Met Val Asp Tyr Pro Tyr Arg Leu Trp His Tyr Pro Cys Thr
    290                 295                 300

Ile Asn Tyr Thr Ile Phe Lys Val Arg Met Tyr Val Gly Gly Val Glu
305                 310                 315                 320

His Arg Leu Glu Ala Ala Cys Asn Trp Thr Arg Gly Glu Arg Cys Asp
                325                 330                 335
```

```
Leu Glu Asp Arg Asp Arg Ser Glu Leu Ser Pro Leu Leu Leu Ser Thr
        340             345             350

Thr Gln Trp Gln Val Leu Pro Cys Ser Phe Thr Thr Leu Pro Ala
        355             360             365
```

(2) INFORMATION FOR SEQ ID NO:10:

(i) SEQUENCE CHARACTERISTICS:
        (A) LENGTH: 434 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Leu Pro Gly Leu Ala Leu Leu Leu Ala Ala Trp Thr Ala Arg
1               5                   10                  15

Ala Leu Glu Val Pro Ser Ser Asn Ser Asp Pro Tyr Gln Val Arg Asn
        20              25              30

Ser Ser Gly Leu Tyr His Val Thr Asn Asp Cys Pro Asn Ser Ser Ile
        35              40              45

Val Tyr Glu Ala Ala Asp Ala Ile Leu His Thr Pro Gly Cys Val Pro
    50              55              60

Cys Val Arg Glu Gly Asn Ala Ser Arg Cys Trp Val Ala Val Thr Pro
65              70              75                      80

Thr Val Ala Thr Arg Asp Gly Lys Leu Pro Thr Thr Gln Leu Arg Arg
            85              90                  95

His Ile Asp Leu Leu Val Gly Ser Ala Thr Leu Cys Ser Ala Leu Tyr
            100             105             110

Val Gly Asp Leu Cys Gly Ser Val Phe Leu Val Gly Gln Leu Phe Thr
            115             120             125

Phe Ser Pro Arg Arg His Trp Thr Thr Gln Asp Cys Asn Cys Ser Ile
    130             135             140

Tyr Pro Gly His Ile Thr Gly His Arg Met Ala Trp Asp Met Met Met
145             150             155                     160

Asn Trp Ser Pro Thr Ala Ala Leu Val Val Ala Gln Gly His Thr Thr
                165             170                 175

Ala Gly Leu Val Arg Leu Leu Ser Pro Gly Ala Lys Gln Asn Ile Gln
            180             185             190

Leu Ile Asn Thr Asn Gly Ser Trp His Ile Asn Ser Thr Ala Leu Asn
        195             200             205

Cys Asn Glu Ser Leu Asn Thr Gly Trp Leu Ala Gly Leu Phe Tyr His
    210             215             220

His Lys Phe Asn Ser Ser Gly Cys Pro Glu Arg Leu Ala Ser Cys Arg
225             230             235             240

Arg Leu Thr Asp Phe Ala Gln Gly Gly Gly Pro Ile Ser Tyr Ala Asn
            245             250             255

Gly Ser Gly Leu Asp Glu Arg Pro Tyr Cys Trp His Tyr Pro Pro Arg
            260             265             270

Pro Cys Gly Ile Val Pro Ala Lys Ser Val Cys Gly Pro Val Tyr Cys
        275             280             285

Phe Thr Pro Ser Pro Val Val Val Gly Thr Thr Asp Arg Ser Gly Ala
    290             295             300

Pro Thr Tyr Ser Trp Gly Ala Asn Asp Thr Asp Val Phe Val Leu Asn
305             310             315             320
```

|       |       |       |       |       |       |       |       |       |       |       |       |       |       |       |
|-------|-------|-------|-------|-------|-------|-------|-------|-------|-------|-------|-------|-------|-------|-------|
| Asn   | Thr   | Arg   | Pro   | Pro<br>325 | Leu | Gly | Asn | Trp | Phe<br>330 | Gly | Cys | Thr | Trp | Met<br>335 | Asn |
| Ser   | Thr   | Gly   | Phe<br>340 | Thr | Lys | Val | Cys | Gly<br>345 | Ala | Pro | Pro | Cys | Val<br>350 | Ile | Gly |
| Gly   | Val   | Gly<br>355 | Asn | Asn | Thr | Leu | Leu<br>360 | Cys | Pro | Thr | Asp | Cys<br>365 | Phe | Arg | Lys |
| His   | Pro<br>370 | Glu | Ala | Thr | Tyr | Ser<br>375 | Arg | Cys | Gly | Ser | Gly<br>380 | Pro | Trp | Ile | Thr |
| Pro<br>385 | Arg | Cys | Met | Val | Asp<br>390 | Tyr | Pro | Tyr | Arg | Leu<br>395 | Trp | His | Tyr | Pro | Cys<br>400 |
| Thr   | Ile   | Asn   | Tyr   | Thr<br>405 | Ile | Phe | Lys | Val | Arg<br>410 | Met | Tyr | Val | Gly | Gly<br>415 | Val |
| Glu   | His   | Arg   | Leu<br>420 | Glu | Ala | Ala | Cys | Asn<br>425 | Trp | Thr | Arg | Gly | Glu<br>430 | Arg | Cys |
| Asp   | Leu   |       |       |       |       |       |       |       |       |       |       |       |       |       |       |

( 2 ) INFORMATION FOR SEQ ID NO:11:

( i ) SEQUENCE CHARACTERISTICS:
( A ) LENGTH: 397 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:11:

|       |       |       |       |       |       |       |       |       |       |       |       |       |       |       |
|-------|-------|-------|-------|-------|-------|-------|-------|-------|-------|-------|-------|-------|-------|-------|
| Met<br>1 | Leu | Pro | Gly | Leu<br>5 | Ala | Leu | Leu | Leu<br>10 | Ala | Ala | Trp | Thr | Ala<br>15 | Arg |
| Ala | Leu | Glu | Val<br>20 | Pro | Ser | Ser | Asn | Ser<br>25 | Asp | Pro | Tyr | Gln | Val<br>30 | Arg | Asn |
| Ser | Ser | Gly<br>35 | Leu | Tyr | His | Val | Thr<br>40 | Asn | Asp | Cys | Pro | Asn<br>45 | Ser | Ser | Ile |
| Val | Tyr<br>50 | Glu | Ala | Ala | Asp | Ala<br>55 | Ile | Leu | His | Thr | Pro<br>60 | Gly | Cys | Val | Pro |
| Cys<br>65 | Val | Arg | Glu | Gly | Asn<br>70 | Ala | Ser | Arg | Cys | Trp<br>75 | Val | Ala | Val | Thr | Pro<br>80 |
| Thr | Val | Ala | Thr | Arg<br>85 | Asp | Gly | Lys | Leu | Pro<br>90 | Thr | Thr | Gln | Leu | Arg<br>95 | Arg |
| His | Trp | Thr | Thr<br>100 | Gln | Asp | Cys | Asn | Cys<br>105 | Ser | Ile | Tyr | Pro | Gly<br>110 | His | Ile |
| Thr | Gly | His<br>115 | Arg | Met | Ala | Trp | Asp<br>120 | Met | Met | Met | Asn | Trp | Ser<br>125 | Pro | Thr |
| Ala | Ala<br>130 | Leu | Val | Val | Ala | Gln<br>135 | Gly | His | Thr | Thr | Ala<br>140 | Gly | Leu | Val | Arg |
| Leu<br>145 | Leu | Ser | Pro | Gly | Ala<br>150 | Lys | Gln | Asn | Ile | Gln<br>155 | Leu | Ile | Asn | Thr | Asn<br>160 |
| Gly | Ser | Trp | His | Ile<br>165 | Asn | Ser | Thr | Ala | Leu<br>170 | Asn | Cys | Asn | Glu | Ser<br>175 | Leu |
| Asn | Thr | Gly | Trp<br>180 | Leu | Ala | Gly | Leu | Phe<br>185 | Tyr | His | His | Lys | Phe<br>190 | Asn | Ser |
| Ser | Gly | Cys<br>195 | Pro | Glu | Arg | Leu | Ala<br>200 | Ser | Cys | Arg | Arg | Leu<br>205 | Thr | Asp | Phe |
| Ala | Gln<br>210 | Gly | Gly | Gly | Pro | Ile<br>215 | Ser | Tyr | Ala | Asn | Gly<br>220 | Ser | Gly | Leu | Asp |
| Glu<br>225 | Arg | Pro | Tyr | Cys | Trp<br>230 | His | Tyr | Pro | Pro | Arg<br>235 | Pro | Cys | Gly | Ile | Val<br>240 |

|     |     |     |     |     |     |     |     |     |     |     |     |     |     |     |
| --- | --- | --- | --- | --- | --- | --- | --- | --- | --- | --- | --- | --- | --- | --- |
| Pro | Ala | Lys | Ser | Val<br>245 | Cys | Gly | Pro | Val<br>250 | Cys | Phe | Thr | Pro | Ser<br>255 | Pro |
| Val | Val | Val | Gly<br>260 | Thr | Thr | Asp | Arg | Ser<br>265 | Gly | Ala | Pro | Thr | Tyr<br>270 | Ser | Trp |
| Gly | Ala | Asn<br>275 | Asp | Thr | Asp | Val | Phe<br>280 | Val | Leu | Asn | Asn | Thr<br>285 | Arg | Pro | Pro |
| Leu | Gly<br>290 | Asn | Trp | Phe | Gly | Cys<br>295 | Thr | Trp | Met | Asn | Ser | Thr<br>300 | Gly | Phe | Thr |
| Lys<br>305 | Val | Cys | Gly | Ala | Pro<br>310 | Pro | Cys | Val | Ile | Gly<br>315 | Gly | Val | Gly | Asn | Asn<br>320 |
| Thr | Leu | Leu | Cys | Pro<br>325 | Thr | Asp | Cys | Phe | Arg<br>330 | Lys | His | Pro | Glu | Ala<br>335 | Thr |
| Tyr | Ser | Arg | Cys<br>340 | Gly | Ser | Gly | Pro | Trp<br>345 | Ile | Thr | Pro | Arg | Cys<br>340 | Met | Val |
| Asp | Tyr | Pro<br>355 | Tyr | Arg | Leu | Trp | His<br>360 | Tyr | Pro | Cys | Thr | Ile<br>365 | Asn | Tyr | Thr |
| Ile | Phe<br>370 | Lys | Val | Arg | Met | Tyr<br>375 | Val | Gly | Gly | Val | Glu<br>380 | His | Arg | Leu | Glu |
| Ala<br>385 | Ala | Cys | Asn | Trp | Thr<br>390 | Arg | Gly | Glu | Arg | Cys<br>395 | Asp | Leu |

(2) INFORMATION FOR SEQ ID NO:12:

(i) SEQUENCE CHARACTERISTICS:
(A) LENGTH: 1648 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:12:

|     |     |     |     |     |     |     |     |     |     |     |     |     |     |     |
| --- | --- | --- | --- | --- | --- | --- | --- | --- | --- | --- | --- | --- | --- | --- |
| Met<br>1 | Ser | Thr | Asn | Pro<br>5 | Lys | Pro | Gln | Arg | Lys<br>10 | Thr | Lys | Arg | Asn | Thr<br>15 | Asn |
| Arg | Arg | Pro | Gln<br>20 | Asp | Val | Lys | Phe | Pro<br>25 | Gly | Gly | Gly | Gln | Ile<br>30 | Val | Gly |
| Gly | Val | Tyr<br>35 | Leu | Leu | Pro | Arg | Arg<br>40 | Gly | Pro | Arg | Leu | Gly<br>45 | Val | Arg | Ala |
| Thr | Arg<br>50 | Lys | Thr | Ser | Glu | Arg<br>55 | Ser | Gln | Pro | Arg | Gly<br>60 | Arg | Arg | Gln | Pro |
| Ile<br>65 | Pro | Lys | Ala | Arg | Arg<br>70 | Pro | Glu | Gly | Arg | Thr<br>75 | Trp | Ala | Gln | Pro | Gly<br>80 |
| Tyr | Pro | Trp | Pro | Leu<br>85 | Tyr | Gly | Asn | Glu | Gly<br>90 | Cys | Gly | Trp | Ala | Gly<br>95 | Trp |
| Leu | Leu | Ser | Pro<br>100 | Arg | Gly | Ser | Arg | Pro<br>105 | Ser | Trp | Gly | Pro | Thr<br>110 | Asp | Pro |
| Arg | Arg | Arg<br>115 | Ser | Arg | Asn | Leu | Gly<br>120 | Lys | Val | Ile | Asp | Thr<br>125 | Leu | Thr | Cys |
| Gly | Phe<br>130 | Ala | Asp | Leu | Met | Gly<br>135 | Tyr | Ile | Pro | Leu | Val<br>140 | Gly | Ala | Pro | Leu |
| Gly<br>145 | Gly | Ala | Ala | Arg | Ala<br>150 | Leu | Ala | His | Gly | Val<br>155 | Arg | Val | Leu | Glu | Asp<br>160 |
| Gly | Val | Asn | Tyr | Ala<br>165 | Thr | Gly | Asn | Leu | Pro<br>170 | Gly | Cys | Ser | Phe | Ser<br>175 | Ile |
| Phe | Leu | Leu | Ala<br>180 | Leu | Leu | Ser | Cys | Leu<br>185 | Thr | Val | Pro | Ala | Ser<br>190 | Ala | Tyr |

```
Gln  Val  Arg  Asn  Ser  Ser  Gly  Leu  Tyr  His  Val  Thr  Asn  Asp  Cys  Pro
          195                      200                     205
Asn  Ser  Ser  Ile  Val  Tyr  Glu  Ala  Ala  Asp  Ala  Ile  Leu  His  Thr  Pro
     210                      215                     220
Gly  Cys  Val  Pro  Cys  Val  Arg  Glu  Gly  Asn  Ala  Ser  Arg  Cys  Trp  Val
225                      230                     235                          240
Ala  Val  Thr  Pro  Thr  Val  Ala  Thr  Arg  Asp  Gly  Lys  Leu  Pro  Thr  Thr
                    245                     250                          255
Gln  Leu  Arg  Arg  His  Ile  Asp  Leu  Leu  Val  Gly  Ser  Ala  Thr  Leu  Cys
               260                      265                     270
Ser  Ala  Leu  Tyr  Val  Gly  Asp  Leu  Cys  Gly  Ser  Val  Phe  Leu  Val  Gly
          275                      280                     285
Gln  Leu  Phe  Thr  Phe  Ser  Pro  Arg  Arg  His  Trp  Thr  Thr  Gln  Asp  Cys
     290                      295                     300
Asn  Cys  Ser  Ile  Tyr  Pro  Gly  His  Ile  Thr  Gly  His  Arg  Met  Ala  Trp
305                      310                     315                          320
Asp  Met  Met  Met  Asn  Trp  Ser  Pro  Thr  Ala  Ala  Leu  Val  Val  Ala  Gln
                    325                     330                          335
Leu  Leu  Arg  Ile  Pro  Gln  Ala  Ile  Leu  Asp  Met  Ile  Ala  Gly  Ala  His
               340                      345                     350
Trp  Gly  Val  Leu  Ala  Gly  Ile  Ala  Tyr  Phe  Ser  Met  Val  Gly  Asn  Trp
          355                      360                     365
Ala  Lys  Val  Leu  Val  Val  Leu  Leu  Leu  Phe  Ala  Gly  Val  Asp  Ala  Glu
     370                      375                     380
Thr  His  Val  Thr  Gly  Gly  Ser  Ala  Gly  His  Thr  Thr  Ala  Gly  Leu  Val
385                      390                     395                          400
Arg  Leu  Leu  Ser  Pro  Gly  Ala  Lys  Gln  Asn  Ile  Gln  Leu  Ile  Asn  Thr
                    405                     410                          415
Asn  Gly  Ser  Trp  His  Ile  Asn  Ser  Thr  Ala  Leu  Asn  Cys  Asn  Glu  Ser
               420                      425                     430
Leu  Asn  Thr  Gly  Trp  Leu  Ala  Gly  Leu  Phe  Tyr  His  His  Lys  Phe  Asn
          435                      440                     445
Ser  Ser  Gly  Cys  Pro  Glu  Arg  Leu  Ala  Ser  Cys  Arg  Arg  Leu  Thr  Asp
     450                      455                     460
Phe  Ala  Gln  Gly  Gly  Gly  Pro  Ile  Ser  Tyr  Ala  Asn  Gly  Ser  Gly  Leu
465                      470                     475                          480
Asp  Glu  Arg  Pro  Tyr  Cys  Trp  His  Tyr  Pro  Pro  Arg  Pro  Cys  Gly  Ile
                    485                     490                          495
Val  Pro  Ala  Lys  Ser  Val  Cys  Gly  Pro  Val  Tyr  Cys  Phe  Thr  Pro  Ser
               500                      505                     510
Pro  Val  Val  Val  Gly  Thr  Thr  Asp  Arg  Ser  Gly  Ala  Pro  Thr  Tyr  Ser
          515                      520                     525
Trp  Gly  Ala  Asn  Asp  Thr  Asp  Val  Phe  Val  Leu  Asn  Asn  Thr  Arg  Pro
     530                      535                     540
Pro  Leu  Gly  Asn  Trp  Phe  Gly  Cys  Thr  Trp  Met  Asn  Ser  Thr  Gly  Phe
545                      550                     555                          560
Thr  Lys  Val  Cys  Gly  Ala  Pro  Pro  Cys  Val  Ile  Gly  Gly  Val  Gly  Asn
                    565                     570                          575
Asn  Thr  Leu  Leu  Cys  Pro  Thr  Asp  Cys  Phe  Arg  Lys  His  Pro  Glu  Ala
               580                      585                     590
Thr  Tyr  Ser  Arg  Cys  Gly  Ser  Gly  Pro  Trp  Ile  Thr  Pro  Arg  Cys  Met
          595                      600                     605
Val  Asp  Tyr  Pro  Tyr  Arg  Leu  Trp  His  Tyr  Pro  Cys  Thr  Ile  Asn  Tyr
610                      615                     620
```

```
Thr  Ile  Phe  Lys  Val  Arg  Met  Tyr  Val  Gly  Gly  Val  Glu  His  Arg  Leu
625                 630                 635                      640

Glu  Ala  Ala  Cys  Asn  Trp  Thr  Arg  Gly  Glu  Arg  Cys  Asp  Leu  Glu  Asp
               645                      650                      655

Arg  Asp  Arg  Ser  Glu  Leu  Ser  Pro  Leu  Leu  Leu  Ser  Thr  Thr  Gln  Trp
               660                      665                      670

Gln  Val  Leu  Pro  Cys  Ser  Phe  Thr  Thr  Leu  Pro  Ala  Leu  Ser  Thr  Gly
          675                      680                      685

Leu  Ile  His  Leu  His  Gln  Asn  Ile  Val  Asp  Val  Gln  Tyr  Leu  Tyr  Gly
          690                      695                      700

Val  Gly  Ser  Ser  Ile  Ala  Ser  Trp  Ala  Ile  Lys  Trp  Glu  Tyr  Val  Val
705                 710                      715                      720

Leu  Leu  Phe  Leu  Leu  Leu  Ala  Asp  Ala  Arg  Val  Cys  Ser  Cys  Leu  Trp
               725                      730                      735

Met  Met  Leu  Leu  Ile  Ser  Gln  Ala  Glu  Ala  Ala  Leu  Glu  Asn  Leu  Val
               740                      745                      750

Ile  Leu  Asn  Ala  Ala  Ser  Leu  Ala  Gly  Thr  His  Gly  Phe  Val  Ser  Phe
          755                      760                      765

Leu  Val  Phe  Phe  Cys  Phe  Ala  Trp  Tyr  Leu  Lys  Gly  Arg  Trp  Val  Pro
770                      775                      780

Gly  Ala  Ala  Tyr  Ala  Leu  Tyr  Gly  Ile  Trp  Pro  Leu  Leu  Leu  Leu  Leu
785                      790                      795                      800

Leu  Ala  Leu  Pro  Gln  Arg  Ala  Tyr  Ala  Leu  Asp  Thr  Glu  Val  Ala  Ala
               805                      810                      815

Ser  Cys  Gly  Gly  Val  Val  Leu  Val  Gly  Leu  Met  Ala  Leu  Thr  Leu  Ser
               820                      825                      830

Pro  Tyr  Tyr  Lys  Arg  Tyr  Ile  Ser  Trp  Cys  Met  Trp  Trp  Leu  Gln  Tyr
          835                      840                      845

Phe  Leu  Thr  Arg  Val  Glu  Ala  Gln  Leu  His  Val  Trp  Val  Pro  Pro  Leu
850                      855                      860

Asn  Val  Arg  Gly  Gly  Arg  Asp  Ala  Val  Ile  Leu  Leu  Met  Cys  Ala  Val
865                      870                      875                      880

His  Pro  Thr  Leu  Val  Phe  Asp  Ile  Thr  Lys  Leu  Leu  Leu  Ala  Ile  Phe
               885                      890                      895

Gly  Pro  Leu  Trp  Ile  Leu  Gln  Ala  Ser  Leu  Leu  Lys  Val  Pro  Tyr  Phe
               900                      905                      910

Val  Arg  Val  Gln  Gly  Leu  Leu  Arg  Ile  Cys  Ala  Leu  Ala  Arg  Lys  Ile
          915                      920                      925

Ala  Gly  Gly  His  Tyr  Val  Gln  Met  Ile  Phe  Ile  Lys  Leu  Gly  Ala  Leu
          930                      935                      940

Thr  Gly  Thr  Tyr  Val  Tyr  Asn  His  Leu  Thr  Pro  Leu  Arg  Asp  Trp  Ala
945                      950                      955                      960

His  Asn  Gly  Leu  Arg  Asp  Leu  Ala  Val  Ala  Val  Glu  Pro  Val  Val  Phe
               965                      970                      975

Ser  Arg  Met  Glu  Thr  Lys  Leu  Ile  Thr  Trp  Gly  Ala  Asp  Thr  Ala  Ala
               980                      985                      990

Cys  Gly  Asp  Ile  Ile  Asn  Gly  Leu  Pro  Val  Ser  Ala  Arg  Arg  Gly  Gln
          995                      1000                     1005

Glu  Ile  Leu  Leu  Gly  Pro  Ala  Asp  Gly  Met  Val  Ser  Lys  Gly  Trp  Arg
     1010                     1015                     1020

Leu  Leu  Ala  Pro  Ile  Thr  Ala  Tyr  Ala  Gln  Gln  Thr  Arg  Gly  Leu  Leu
1025                     1030                     1035                     1040
```

-continued

| | | | | | | | | | | | | | | |
|---|---|---|---|---|---|---|---|---|---|---|---|---|---|---|
| Gly | Cys | Ile | Ile | Thr | Ser | Leu | Thr | Gly | Arg | Asp | Lys | Asn | Gln | Val | Glu |
| | | | | 1045 | | | | 1050 | | | | | 1055 | | |

Gly Cys Ile Ile Thr Ser Leu Thr Gly Arg Asp Lys Asn Gln Val Glu
                1045                1050                    1055

Gly Glu Val Gln Ile Val Ser Thr Ala Thr Gln Thr Phe Leu Ala Thr
                1060                1065                    1070

Cys Ile Asn Gly Val Cys Trp Thr Val Tyr His Gly Ala Gly Thr Arg
            1075                1080                    1085

Thr Ile Ala Ser Pro Lys Gly Pro Val Ile Gln Met Tyr Thr Asn Val
    1090                    1095                1100

Asp Gln Asp Leu Val Gly Trp Pro Ala Pro Gln Gly Ser Arg Ser Leu
1105                1110                    1115                    1120

Thr Pro Cys Thr Cys Gly Ser Ser Asp Leu Tyr Leu Val Thr Arg His
            1125                1130                    1135

Ala Asp Val Ile Pro Val Arg Arg Gln Gly Asp Ser Arg Gly Ser Leu
            1140                1145                    1150

Leu Ser Pro Arg Pro Ile Ser Tyr Leu Lys Gly Ser Ser Gly Gly Pro
        1155                1160                    1165

Leu Leu Cys Pro Ala Gly His Ala Val Gly Leu Phe Arg Ala Ala Val
        1170                1175                    1180

Cys Thr Arg Gly Val Ala Lys Ala Val Asp Phe Ile Pro Val Glu Asn
1185                1190                    1195                    1200

Leu Glu Thr Thr Met Arg Ser Pro Val Phe Thr Asp Asn Ser Ser Pro
                1205                1210                    1215

Pro Ala Val Pro Gln Ser Phe Gln Val Ala His Leu His Ala Pro Thr
            1220                1225                    1230

Gly Ser Gly Lys Ser Thr Lys Val Pro Ala Ala Tyr Ala Ala Gln Gly
        1235                1240                    1245

Tyr Lys Val Leu Val Leu Asn Pro Ser Val Ala Ala Thr Leu Gly Phe
    1250                    1255                1260

Gly Ala Tyr Met Ser Lys Ala His Gly Val Asp Pro Asn Ile Arg Thr
1265                1270                    1275                    1280

Gly Val Arg Thr Ile Thr Thr Gly Ser Pro Ile Thr Tyr Ser Thr Tyr
                1285                1290                    1295

Gly Lys Phe Leu Ala Asp Gly Gly Cys Ser Gly Gly Ala Tyr Asp Ile
            1300                1305                    1310

Ile Ile Cys Asp Glu Cys His Ser Thr Asp Ala Thr Ser Ile Leu Gly
        1315                1320                    1325

Ile Gly Thr Val Leu Asp Gln Ala Glu Thr Ala Gly Ala Arg Leu Val
    1330                    1335                1340

Val Leu Ala Thr Ala Thr Pro Pro Gly Ser Val Thr Val Pro His Pro
1345                1350                    1355                    1360

Asn Ile Glu Glu Val Ala Leu Ser Thr Thr Gly Glu Ile Pro Phe Tyr
                1365                1370                    1375

Gly Lys Ala Ile Pro Leu Glu Val Ile Lys Gly Gly Arg His Leu Ile
            1380                1385                    1390

Phe Cys His Ser Lys Lys Lys Cys Asp Glu Leu Ala Ala Lys Leu Val
        1395                1400                    1405

Ala Leu Gly Ile Asn Ala Val Ala Tyr Tyr Arg Gly Leu Asp Val Ser
    1410                    1415                1420

Val Ile Pro Ala Ser Gly Asp Val Val Val Ser Thr Asp Ala Leu
1425                1430                    1435                    1440

Met Thr Gly Phe Thr Gly Asp Phe Asp Pro Val Ile Asp Cys Asn Thr
                1445                1450                    1455

Cys Val Thr Gln Thr Val Asp Phe Ser Leu Asp Pro Thr Phe Thr Ile
            1460                1465                    1470

```
Glu  Thr  Thr  Thr  Leu  Pro  Gln  Asp  Ala  Val  Ser  Arg  Thr  Gln  Arg  Arg
          1475                1480                1485

Gly  Arg  Thr  Gly  Arg  Gly  Lys  Pro  Gly  Ile  Tyr  Arg  Phe  Val  Ala  Pro
     1490                1495                1500

Gly  Glu  Arg  Pro  Ser  Gly  Met  Phe  Asp  Ser  Ser  Val  Leu  Cys  Glu  Cys
1505                1510                1515                          1520

Tyr  Asp  Ala  Gly  Cys  Ala  Trp  Tyr  Glu  Leu  Thr  Pro  Ala  Glu  Thr  Thr
               1525                1530                          1535

Val  Arg  Leu  Arg  Ala  Tyr  Met  Asn  Thr  Pro  Gly  Leu  Pro  Val  Cys  Gln
          1540                1545                          1550

Asp  His  Leu  Glu  Phe  Trp  Glu  Gly  Val  Phe  Thr  Gly  Leu  Thr  His  Ile
          1555                1560                          1565

Asp  Ala  His  Phe  Leu  Ser  Gln  Thr  Lys  Gln  Ser  Gly  Glu  Asn  Phe  Pro
          1570                1575                1580

Tyr  Leu  Val  Ala  Tyr  Gln  Ala  Thr  Val  Cys  Ala  Arg  Ala  Gln  Ala  Pro
1585                1590                1595                          1600

Pro  Pro  Ser  Trp  Asp  Gln  Met  Trp  Lys  Cys  Leu  Ile  Arg  Leu  Lys  Pro
               1605                1610                          1615

Thr  Leu  His  Gly  Pro  Thr  Pro  Leu  Leu  Tyr  Arg  Leu  Gly  Ala  Val  Gln
          1620                1625                          1630

Asn  Glu  Ile  Thr  Leu  Thr  His  Pro  Val  Thr  Lys  Tyr  Ile  Met  Thr  Cys
          1635                1640                          1645
```

(2) INFORMATION FOR SEQ ID NO:13:

(i) SEQUENCE CHARACTERISTICS:
        (A) LENGTH: 967 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Met  Ser  Thr  Asn  Pro  Lys  Pro  Gln  Arg  Lys  Thr  Lys  Arg  Asn  Thr  Asn
1              5                   10                       15

Arg  Arg  Pro  Gln  Asp  Val  Lys  Phe  Pro  Gly  Gly  Gly  Gln  Ile  Val  Gly
               20                  25                       30

Gly  Val  Tyr  Leu  Leu  Pro  Arg  Arg  Gly  Pro  Arg  Leu  Gly  Val  Arg  Ala
               35                  40                       45

Thr  Arg  Lys  Thr  Ser  Glu  Arg  Ser  Gln  Pro  Arg  Gly  Arg  Arg  Gln  Pro
          50                  55                       60

Ile  Pro  Lys  Ala  Arg  Arg  Pro  Glu  Gly  Arg  Thr  Trp  Ala  Gln  Pro  Gly
65                       70                  75                            80

Tyr  Pro  Trp  Pro  Leu  Tyr  Gly  Asn  Glu  Gly  Cys  Gly  Trp  Ala  Gly  Trp
                    85                  90                       95

Leu  Leu  Ser  Pro  Arg  Gly  Ser  Arg  Pro  Ser  Trp  Gly  Pro  Thr  Asp  Pro
               100                 105                      110

Arg  Arg  Arg  Ser  Arg  Asn  Leu  Gly  Lys  Val  Ile  Asp  Thr  Leu  Thr  Cys
          115                 120                      125

Gly  Phe  Ala  Asp  Leu  Met  Gly  Tyr  Ile  Pro  Leu  Val  Gly  Ala  Pro  Leu
     130                 135                      140

Gly  Gly  Ala  Ala  Arg  Ala  Leu  Ala  His  Gly  Val  Arg  Val  Leu  Glu  Asp
145                      150                 155                           160

Gly  Val  Asn  Tyr  Ala  Thr  Gly  Asn  Leu  Pro  Gly  Cys  Ser  Phe  Ser  Ile
               165                 170                      175
```

```
Phe  Leu  Leu  Ala  Leu  Leu  Ser  Cys  Leu  Thr  Val  Pro  Ala  Ser  Ala  Tyr
               180                      185                      190

Gln  Val  Arg  Asn  Ser  Ser  Gly  Leu  Tyr  His  Val  Thr  Asn  Asp  Cys  Pro
          195                      200                      205

Asn  Ser  Ser  Ile  Val  Tyr  Glu  Ala  Ala  Asp  Ala  Ile  Leu  His  Thr  Pro
     210                      215                      220

Gly  Cys  Val  Pro  Cys  Val  Arg  Glu  Gly  Asn  Ala  Ser  Arg  Cys  Trp  Val
225                      230                      235                      240

Ala  Val  Thr  Pro  Thr  Val  Ala  Thr  Arg  Asp  Gly  Lys  Leu  Pro  Thr  Thr
               245                      250                      255

Gln  Leu  Arg  Arg  His  Ile  Asp  Leu  Leu  Val  Gly  Ser  Ala  Thr  Leu  Cys
          260                      265                      270

Ser  Ala  Leu  Tyr  Val  Gly  Asp  Leu  Cys  Gly  Ser  Val  Phe  Leu  Val  Gly
               275                      280                      285

Gln  Leu  Phe  Thr  Phe  Ser  Pro  Arg  Arg  His  Trp  Thr  Thr  Gln  Asp  Cys
290                      295                      300

Asn  Cys  Ser  Ile  Tyr  Pro  Gly  His  Ile  Thr  Gly  His  Arg  Met  Ala  Trp
305                      310                      315                      320

Asp  Met  Met  Met  Asn  Trp  Ser  Pro  Thr  Ala  Ala  Leu  Val  Val  Ala  Gln
                    325                      330                      335

Leu  Leu  Arg  Ile  Pro  Gln  Ala  Ile  Leu  Asp  Met  Ile  Ala  Gly  Ala  His
          340                      345                      350

Trp  Gly  Val  Leu  Ala  Gly  Ile  Ala  Tyr  Phe  Ser  Met  Val  Gly  Asn  Trp
          355                      360                      365

Ala  Lys  Val  Leu  Val  Val  Leu  Leu  Leu  Phe  Ala  Gly  Val  Asp  Ala  Glu
     370                      375                      380

Thr  His  Val  Thr  Gly  Gly  Ser  Ala  Gly  His  Thr  Thr  Ala  Gly  Leu  Val
385                      390                      395                      400

Arg  Leu  Leu  Ser  Pro  Gly  Ala  Lys  Gln  Asn  Ile  Gln  Leu  Ile  Asn  Thr
               405                      410                      415

Asn  Gly  Ser  Trp  His  Ile  Asn  Ser  Thr  Ala  Leu  Asn  Cys  Asn  Glu  Ser
               420                      425                      430

Leu  Asn  Thr  Gly  Trp  Leu  Ala  Gly  Leu  Phe  Tyr  His  His  Lys  Phe  Asn
          435                      440                      445

Ser  Ser  Gly  Cys  Pro  Glu  Arg  Leu  Ala  Ser  Cys  Arg  Arg  Leu  Thr  Asp
     450                      455                      460

Phe  Ala  Gln  Gly  Gly  Gly  Pro  Ile  Ser  Tyr  Ala  Asn  Gly  Ser  Gly  Leu
465                      470                      475                      480

Asp  Glu  Arg  Pro  Tyr  Cys  Trp  His  Tyr  Pro  Pro  Arg  Pro  Cys  Gly  Ile
               485                      490                      495

Val  Pro  Ala  Lys  Ser  Val  Cys  Gly  Pro  Val  Tyr  Cys  Phe  Thr  Pro  Ser
               500                      505                      510

Pro  Val  Val  Val  Gly  Thr  Thr  Asp  Arg  Ser  Gly  Ala  Pro  Thr  Tyr  Ser
          515                      520                      525

Trp  Gly  Ala  Asn  Asp  Thr  Asp  Val  Phe  Val  Leu  Asn  Asn  Thr  Arg  Pro
     530                      535                      540

Pro  Leu  Gly  Asn  Trp  Phe  Gly  Cys  Thr  Trp  Met  Asn  Ser  Thr  Gly  Phe
545                      550                      555                      560

Thr  Lys  Val  Cys  Gly  Ala  Pro  Pro  Cys  Val  Ile  Gly  Gly  Val  Gly  Asn
               565                      570                      575

Asn  Thr  Leu  Leu  Cys  Pro  Thr  Asp  Cys  Phe  Arg  Lys  His  Pro  Glu  Ala
               580                      585                      590

Thr  Tyr  Ser  Arg  Cys  Gly  Ser  Gly  Pro  Trp  Ile  Thr  Pro  Arg  Cys  Met
               595                      600                      605
```

```
Val  Asp  Tyr  Pro  Tyr  Arg  Leu  Trp  His  Tyr  Pro  Cys  Thr  Ile  Asn  Tyr
     610                      615                     620

Thr  Ile  Phe  Lys  Val  Arg  Met  Tyr  Val  Gly  Gly  Val  Glu  His  Arg  Leu
625                      630                     635                         640

Glu  Ala  Ala  Cys  Asn  Trp  Thr  Arg  Gly  Glu  Arg  Cys  Asp  Leu  Glu  Asp
               645                      650                          655

Arg  Asp  Arg  Ser  Glu  Leu  Ser  Pro  Leu  Leu  Leu  Ser  Thr  Thr  Gln  Trp
               660                     665                     670

Gln  Val  Leu  Pro  Cys  Ser  Phe  Thr  Thr  Leu  Pro  Ala  Leu  Ser  Thr  Gly
               675                     680                     685

Leu  Ile  His  Leu  His  Gln  Asn  Ile  Val  Asp  Val  Gln  Tyr  Leu  Tyr  Gly
     690                      695                          700

Val  Gly  Ser  Ser  Ile  Ala  Ser  Trp  Ala  Ile  Lys  Trp  Glu  Tyr  Val  Val
705                      710                     715                         720

Leu  Leu  Phe  Leu  Leu  Leu  Ala  Asp  Ala  Arg  Val  Cys  Ser  Cys  Leu  Trp
               725                     730                          735

Met  Met  Leu  Leu  Ile  Ser  Gln  Ala  Glu  Ala  Ala  Leu  Glu  Asn  Leu  Val
               740                     745                          750

Ile  Leu  Asn  Ala  Ala  Ser  Leu  Ala  Gly  Thr  His  Gly  Phe  Val  Ser  Phe
          755                     760                          765

Leu  Val  Phe  Phe  Cys  Phe  Ala  Trp  Tyr  Leu  Lys  Gly  Arg  Trp  Val  Pro
     770                      775                     780

Gly  Ala  Ala  Tyr  Ala  Leu  Tyr  Gly  Ile  Trp  Pro  Leu  Leu  Leu  Leu  Leu
785                      790                     795                         800

Leu  Ala  Leu  Pro  Gln  Arg  Ala  Tyr  Ala  Leu  Asp  Thr  Glu  Val  Ala  Ala
               805                     810                          815

Ser  Cys  Gly  Gly  Val  Val  Leu  Val  Gly  Leu  Met  Ala  Leu  Thr  Leu  Ser
               820                     825                          830

Pro  Tyr  Tyr  Lys  Arg  Tyr  Ile  Ser  Trp  Cys  Met  Trp  Trp  Leu  Gln  Tyr
          835                     840                     845

Phe  Leu  Thr  Arg  Val  Glu  Ala  Gln  Leu  His  Val  Trp  Val  Pro  Pro  Leu
     850                      855                     860

Asn  Val  Arg  Gly  Gly  Arg  Asp  Ala  Val  Ile  Leu  Leu  Met  Cys  Ala  Val
865                      870                     875                         880

His  Pro  Thr  Leu  Val  Phe  Asp  Ile  Thr  Lys  Leu  Leu  Leu  Ala  Ile  Phe
               885                     890                          895

Gly  Pro  Leu  Trp  Ile  Leu  Gln  Ala  Ser  Leu  Leu  Lys  Val  Pro  Tyr  Phe
               900                     905                          910

Val  Arg  Val  Gln  Gly  Leu  Leu  Arg  Ile  Cys  Ala  Leu  Ala  Arg  Lys  Ile
          915                     920                     925

Ala  Gly  Gly  His  Tyr  Val  Gln  Met  Ile  Phe  Ile  Lys  Leu  Gly  Ala  Leu
     930                      935                     940

Thr  Gly  Thr  Tyr  Val  Tyr  Asn  His  Leu  Thr  Pro  Leu  Arg  Asp  Trp  Ala
945                      950                     955                         960

His  Asn  Gly  Leu  Arg  Asp  Leu
                    965
```

( 2 ) INFORMATION FOR SEQ ID NO:14:

( i ) SEQUENCE CHARACTERISTICS:
        ( A ) LENGTH: 687 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

| | | | | | | | | | | | | | | |
|---|---|---|---|---|---|---|---|---|---|---|---|---|---|---|
| Asn | Ser | Thr | Met | Asp | Leu | Ala | Val | Ala | Val | Glu | Pro | Val | Val | Phe | Ser |
| 1 | | | | 5 | | | | | 10 | | | | | 15 | |
| Arg | Met | Glu | Thr | Lys | Leu | Ile | Thr | Trp | Gly | Ala | Asp | Thr | Ala | Ala | Cys |
| | | | 20 | | | | | 25 | | | | | 30 | | |
| Gly | Asp | Ile | Ile | Asn | Gly | Leu | Pro | Val | Ser | Ala | Arg | Arg | Gly | Gln | Glu |
| | | | 35 | | | | 40 | | | | | 45 | | | |
| Ile | Leu | Leu | Gly | Pro | Ala | Asp | Gly | Met | Val | Ser | Lys | Gly | Trp | Arg | Leu |
| | 50 | | | | | 55 | | | | | 60 | | | | |
| Leu | Ala | Pro | Ile | Thr | Ala | Tyr | Ala | Gln | Gln | Thr | Arg | Gly | Leu | Leu | Gly |
| 65 | | | | | 70 | | | | | 75 | | | | | 80 |
| Cys | Ile | Ile | Thr | Ser | Leu | Thr | Gly | Arg | Asp | Lys | Asn | Gln | Val | Glu | Gly |
| | | | | 85 | | | | | 90 | | | | | 95 | |
| Glu | Val | Gln | Ile | Val | Ser | Thr | Ala | Thr | Gln | Thr | Phe | Leu | Ala | Thr | Cys |
| | | | 100 | | | | | 105 | | | | | 110 | | |
| Ile | Asn | Gly | Val | Cys | Trp | Thr | Val | Tyr | His | Gly | Ala | Gly | Thr | Arg | Thr |
| | | | 115 | | | | | 120 | | | | | 125 | | |
| Ile | Ala | Ser | Pro | Lys | Gly | Pro | Val | Ile | Gln | Met | Tyr | Thr | Asn | Val | Asp |
| | 130 | | | | | 135 | | | | | 140 | | | | |
| Gln | Asp | Leu | Val | Gly | Trp | Pro | Ala | Pro | Gln | Gly | Ser | Arg | Ser | Leu | Thr |
| 145 | | | | | 150 | | | | | 155 | | | | | 160 |
| Pro | Cys | Thr | Cys | Gly | Ser | Ser | Asp | Leu | Tyr | Leu | Val | Thr | Arg | His | Ala |
| | | | | 165 | | | | | 170 | | | | | 175 | |
| Asp | Val | Ile | Pro | Val | Arg | Arg | Gln | Gly | Asp | Ser | Arg | Gly | Ser | Leu | Leu |
| | | | 180 | | | | | 185 | | | | | 190 | | |
| Ser | Pro | Arg | Pro | Ile | Ser | Tyr | Leu | Lys | Gly | Ser | Ser | Gly | Gly | Pro | Leu |
| | | | 195 | | | | | 200 | | | | | 205 | | |
| Leu | Cys | Pro | Ala | Gly | His | Ala | Val | Gly | Leu | Phe | Arg | Ala | Ala | Val | Cys |
| | 210 | | | | | 215 | | | | | 220 | | | | |
| Thr | Arg | Gly | Val | Ala | Lys | Ala | Val | Asp | Phe | Ile | Pro | Val | Glu | Asn | Leu |
| 225 | | | | | 230 | | | | | 235 | | | | | 240 |
| Glu | Thr | Thr | Met | Arg | Ser | Pro | Val | Phe | Thr | Asp | Asn | Ser | Ser | Pro | Pro |
| | | | | 245 | | | | | 250 | | | | | 255 | |
| Ala | Val | Pro | Gln | Ser | Phe | Gln | Val | Ala | His | Leu | His | Ala | Pro | Thr | Gly |
| | | | 260 | | | | | 265 | | | | | 270 | | |
| Ser | Gly | Lys | Ser | Thr | Lys | Val | Pro | Ala | Ala | Tyr | Ala | Ala | Gln | Gly | Tyr |
| | | | 275 | | | | | 280 | | | | | 285 | | |
| Lys | Val | Leu | Val | Leu | Asn | Pro | Ser | Val | Ala | Ala | Thr | Leu | Gly | Phe | Gly |
| | 290 | | | | | 295 | | | | | 300 | | | | |
| Ala | Tyr | Met | Ser | Lys | Ala | His | Gly | Val | Asp | Pro | Asn | Ile | Arg | Thr | Gly |
| 305 | | | | | 310 | | | | | 315 | | | | | 320 |
| Val | Arg | Thr | Ile | Thr | Thr | Gly | Ser | Pro | Ile | Thr | Tyr | Ser | Thr | Tyr | Gly |
| | | | | 325 | | | | | 330 | | | | | 335 | |
| Lys | Phe | Leu | Ala | Asp | Gly | Gly | Cys | Ser | Gly | Gly | Ala | Tyr | Asp | Ile | Ile |
| | | | 340 | | | | | 345 | | | | | 350 | | |
| Ile | Cys | Asp | Glu | Cys | His | Ser | Thr | Asp | Ala | Thr | Ser | Ile | Leu | Gly | Ile |
| | | | 355 | | | | | 360 | | | | | 365 | | |
| Gly | Thr | Val | Leu | Asp | Gln | Ala | Glu | Thr | Ala | Gly | Ala | Arg | Leu | Val | Val |
| | 370 | | | | | 375 | | | | | 380 | | | | |
| Leu | Ala | Thr | Ala | Thr | Pro | Pro | Gly | Ser | Val | Thr | Val | Pro | His | Pro | Asn |
| 385 | | | | | 390 | | | | | 395 | | | | | 400 |
| Ile | Glu | Glu | Val | Ala | Leu | Ser | Thr | Thr | Gly | Glu | Ile | Pro | Phe | Tyr | Gly |
| | | | | 405 | | | | | 410 | | | | | 415 | |

|        |     |     |     |     |     |     |     |     |     |     |     |     |     |     |     |
|--------|-----|-----|-----|-----|-----|-----|-----|-----|-----|-----|-----|-----|-----|-----|-----|
| Lys | Ala | Ile | Pro | Leu | Glu | Val | Ile | Lys | Gly | Gly | Arg | His | Leu | Ile | Phe |
|     |     |     | 420 |     |     |     |     | 425 |     |     |     |     |     | 430 |     |
| Cys | His | Ser | Lys | Lys | Lys | Cys | Asp | Glu | Leu | Ala | Ala | Lys | Leu | Val | Ala |
|     |     | 435 |     |     |     |     | 440 |     |     |     |     | 445 |     |     |     |
| Leu | Gly | Ile | Asn | Ala | Val | Ala | Tyr | Tyr | Arg | Gly | Leu | Asp | Val | Ser | Val |
|     |     | 450 |     |     |     | 455 |     |     |     |     | 460 |     |     |     |     |
| Ile | Pro | Ala | Ser | Gly | Asp | Val | Val | Val | Ser | Thr | Asp | Ala | Leu | Met |     |
| 465 |     |     |     |     | 470 |     |     |     | 475 |     |     |     |     | 480 |     |
| Thr | Gly | Phe | Thr | Gly | Asp | Phe | Asp | Pro | Val | Ile | Asp | Cys | Asn | Thr | Cys |
|     |     |     |     | 485 |     |     |     |     | 490 |     |     |     |     | 495 |     |
| Val | Thr | Gln | Thr | Val | Asp | Phe | Ser | Leu | Asp | Pro | Thr | Phe | Thr | Ile | Glu |
|     |     |     | 500 |     |     |     |     | 505 |     |     |     |     | 510 |     |     |
| Thr | Thr | Thr | Leu | Pro | Gln | Asp | Ala | Val | Ser | Arg | Thr | Gln | Arg | Arg | Gly |
|     |     |     | 515 |     |     |     | 520 |     |     |     |     | 525 |     |     |     |
| Arg | Thr | Gly | Arg | Gly | Lys | Pro | Gly | Ile | Tyr | Arg | Phe | Val | Ala | Pro | Gly |
|     |     | 530 |     |     |     | 535 |     |     |     |     | 540 |     |     |     |     |
| Glu | Arg | Pro | Ser | Gly | Met | Phe | Asp | Ser | Ser | Val | Leu | Cys | Glu | Cys | Tyr |
| 545 |     |     |     |     | 550 |     |     |     |     | 555 |     |     |     |     | 560 |
| Asp | Ala | Gly | Cys | Ala | Trp | Tyr | Glu | Leu | Thr | Pro | Ala | Glu | Thr | Thr | Val |
|     |     |     |     | 565 |     |     |     |     | 570 |     |     |     |     | 575 |     |
| Arg | Leu | Arg | Ala | Tyr | Met | Asn | Thr | Pro | Gly | Leu | Pro | Val | Cys | Gln | Asp |
|     |     |     | 580 |     |     |     |     | 585 |     |     |     |     | 590 |     |     |
| His | Leu | Glu | Phe | Trp | Glu | Gly | Val | Phe | Thr | Gly | Leu | Thr | His | Ile | Asp |
|     |     | 595 |     |     |     |     | 600 |     |     |     |     | 605 |     |     |     |
| Ala | His | Phe | Leu | Ser | Gln | Thr | Lys | Gln | Ser | Gly | Glu | Asn | Phe | Pro | Tyr |
|     | 610 |     |     |     |     | 615 |     |     |     |     | 620 |     |     |     |     |
| Leu | Val | Ala | Tyr | Gln | Ala | Thr | Val | Cys | Ala | Arg | Ala | Gln | Ala | Pro | Pro |
| 625 |     |     |     |     | 630 |     |     |     |     | 635 |     |     |     |     | 640 |
| Pro | Ser | Trp | Asp | Gln | Met | Trp | Lys | Cys | Leu | Ile | Arg | Leu | Lys | Pro | Thr |
|     |     |     |     | 645 |     |     |     |     | 650 |     |     |     |     | 655 |     |
| Leu | His | Gly | Pro | Thr | Pro | Leu | Leu | Tyr | Arg | Leu | Gly | Ala | Val | Gln | Asn |
|     |     |     | 660 |     |     |     |     | 665 |     |     |     |     | 670 |     |     |
| Glu | Ile | Thr | Leu | Thr | His | Pro | Val | Thr | Lys | Tyr | Ile | Met | Thr | Cys |     |
|     |     | 675 |     |     |     |     | 680 |     |     |     |     | 685 |     |     |     |

( 2 ) INFORMATION FOR SEQ ID NO:15:

( i ) SEQUENCE CHARACTERISTICS:
 ( A ) LENGTH: 490 amino acids
 ( B ) TYPE: amino acid
 ( C ) STRANDEDNESS: single
 ( D ) TOPOLOGY: linear ( i i ) MOLECULE TYPE: protein ( x i ) SEQUENCE DESCRIPTION: SEQ ID NO:15:

|        |     |     |     |     |     |     |     |     |     |     |     |     |     |     |     |
|--------|-----|-----|-----|-----|-----|-----|-----|-----|-----|-----|-----|-----|-----|-----|-----|
| Met | Leu | Pro | Gly | Leu | Ala | Leu | Leu | Leu | Ala | Ala | Trp | Thr | Ala | Arg |     |
| 1 |     |     |     | 5 |     |     |     |     | 10 |     |     |     |     | 15 |     |
| Ala | Leu | Glu | Val | Pro | Ser | Ser | Asn | Ser | Asp | Pro | Tyr | Gln | Val | Arg | Asn |
|     |     |     | 20 |     |     |     |     | 25 |     |     |     |     | 30 |     |     |
| Ser | Ser | Gly | Leu | Tyr | His | Val | Thr | Asn | Asp | Cys | Pro | Asn | Ser | Ser | Ile |
|     |     | 35 |     |     |     |     | 40 |     |     |     |     | 45 |     |     |     |
| Val | Tyr | Glu | Ala | Ala | Asp | Ala | Ile | Leu | His | Thr | Pro | Gly | Cys | Val | Pro |
|     | 50 |     |     |     |     | 55 |     |     |     |     | 60 |     |     |     |     |
| Cys | Val | Arg | Glu | Gly | Asn | Ala | Ser | Arg | Cys | Trp | Val | Ala | Val | Thr | Pro |
| 65 |     |     |     |     | 70 |     |     |     |     | 75 |     |     |     |     | 80 |

```
Thr Val Ala Thr Arg Asp Gly Lys Leu Pro Thr Thr Gln Leu Arg Arg
             85                  90                  95

His Ile Asp Leu Leu Val Gly Ser Ala Thr Leu Cys Ser Ala Leu Tyr
             100                 105                 110

Val Gly Asp Leu Cys Gly Ser Val Phe Leu Val Gly Gln Leu Phe Thr
             115                 120                 125

Phe Ser Pro Arg Arg His Trp Thr Thr Gln Asp Cys Asn Cys Ser Ile
         130                 135                 140

Tyr Pro Gly His Ile Thr Gly His Arg Met Ala Trp Asp Met Met Met
145                 150                 155                 160

Asn Trp Ser Pro Thr Ala Ala Leu Val Val Ala Gln Leu Leu Arg Ile
                165                 170                 175

Pro Gln Ala Ile Leu Asp Met Ile Ala Gly Ala His Trp Gly Val Leu
             180                 185                 190

Ala Gly Ile Ala Tyr Phe Ser Met Val Gly Asn Trp Ala Lys Val Leu
             195                 200                 205

Val Val Leu Leu Leu Phe Ala Gly Val Asp Ala Glu Thr His Val Thr
         210                 215                 220

Gly Gly Ser Ala Gly His Thr Thr Ala Gly Leu Val Arg Leu Leu Ser
225                 230                 235                 240

Pro Gly Ala Lys Gln Asn Ile Gln Leu Ile Asn Thr Asn Gly Ser Trp
             245                 250                 255

His Ile Asn Ser Thr Ala Leu Asn Cys Asn Glu Ser Leu Asn Thr Gly
             260                 265                 270

Trp Leu Ala Gly Leu Phe Tyr His His Lys Phe Asn Ser Ser Gly Cys
         275                 280                 285

Pro Glu Arg Leu Ala Ser Cys Arg Arg Leu Thr Asp Phe Ala Gln Gly
    290                 295                 300

Gly Gly Pro Ile Ser Tyr Ala Asn Gly Ser Gly Leu Asp Glu Arg Pro
305                 310                 315                 320

Tyr Cys Trp His Tyr Pro Pro Arg Pro Cys Gly Ile Val Pro Ala Lys
             325                 330                 335

Ser Val Cys Gly Pro Val Tyr Cys Phe Thr Pro Ser Pro Val Val Val
             340                 345                 350

Gly Thr Thr Asp Arg Ser Gly Ala Pro Thr Tyr Ser Trp Gly Ala Asn
         355                 360                 365

Asp Thr Asp Val Phe Val Leu Asn Asn Thr Arg Pro Pro Leu Gly Asn
    370                 375                 380

Trp Phe Gly Cys Thr Trp Met Asn Ser Thr Gly Phe Thr Lys Val Cys
385                 390                 395                 400

Gly Ala Pro Pro Cys Val Ile Gly Gly Val Gly Asn Asn Thr Leu Leu
             405                 410                 415

Cys Pro Thr Asp Cys Phe Arg Lys His Pro Glu Ala Thr Tyr Ser Arg
             420                 425                 430

Cys Gly Ser Gly Pro Trp Ile Thr Pro Arg Cys Met Val Asp Tyr Pro
         435                 440                 445

Tyr Arg Leu Trp His Tyr Pro Cys Thr Ile Asn Tyr Thr Ile Phe Lys
    450                 455                 460

Val Arg Met Tyr Val Gly Gly Val Glu His Arg Leu Glu Ala Ala Cys
465                 470                 475                 480

Asn Trp Thr Arg Gly Glu Arg Cys Asp Leu
             485                 490
```

( 2 ) INFORMATION FOR SEQ ID NO:16:

( i ) SEQUENCE CHARACTERISTICS:
   ( A ) LENGTH: 453 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:16:

```
Met Leu Pro Gly Leu Ala Leu Leu Leu Leu Ala Ala Trp Thr Ala Arg
 1               5                  10                  15

Ala Leu Glu Val Pro Ser Ser Asn Ser Asp Pro Tyr Gln Val Arg Asn
            20                  25                  30

Ser Ser Gly Leu Tyr His Val Thr Asn Asp Cys Pro Asn Ser Ser Ile
        35                  40                  45

Val Tyr Glu Ala Ala Asp Ala Ile Leu His Thr Pro Gly Cys Val Pro
    50                  55                  60

Cys Val Arg Glu Gly Asn Ala Ser Arg Cys Trp Val Ala Val Thr Pro
65                  70                  75                  80

Thr Val Ala Thr Arg Asp Gly Lys Leu Pro Thr Thr Gln Leu Arg Arg
                85                  90                  95

His Trp Thr Thr Gln Asp Cys Asn Cys Ser Ile Tyr Pro Gly His Ile
               100                 105                 110

Thr Gly His Arg Met Ala Trp Asp Met Met Met Asn Trp Ser Pro Thr
            115                 120                 125

Ala Ala Leu Val Val Ala Gln Leu Leu Arg Ile Pro Gln Ala Ile Leu
130                 135                 140

Asp Met Ile Ala Gly Ala His Trp Gly Val Leu Ala Gly Ile Ala Tyr
145                 150                 155                 160

Phe Ser Met Val Gly Asn Trp Ala Lys Val Leu Val Val Leu Leu Leu
                165                 170                 175

Phe Ala Gly Val Asp Ala Glu Thr His Val Thr Gly Gly Ser Ala Gly
            180                 185                 190

His Thr Thr Ala Gly Leu Val Arg Leu Leu Ser Pro Gly Ala Lys Gln
        195                 200                 205

Asn Ile Gln Leu Ile Asn Thr Asn Gly Ser Trp His Ile Asn Ser Thr
    210                 215                 220

Ala Leu Asn Cys Asn Glu Ser Leu Asn Thr Gly Trp Leu Ala Gly Leu
225                 230                 235                 240

Phe Tyr His His Lys Phe Asn Ser Ser Gly Cys Pro Glu Arg Leu Ala
                245                 250                 255

Ser Cys Arg Arg Leu Thr Asp Phe Ala Gln Gly Gly Gly Pro Ile Ser
            260                 265                 270

Tyr Ala Asn Gly Ser Gly Leu Asp Glu Arg Pro Tyr Cys Trp His Tyr
        275                 280                 285

Pro Pro Arg Pro Cys Gly Ile Val Pro Ala Lys Ser Val Cys Gly Pro
    290                 295                 300

Val Tyr Cys Phe Thr Pro Ser Pro Val Val Val Gly Thr Thr Asp Arg
305                 310                 315                 320

Ser Gly Ala Pro Thr Tyr Ser Trp Gly Ala Asn Asp Thr Asp Val Phe
                325                 330                 335

Val Leu Asn Asn Thr Arg Pro Pro Leu Gly Asn Trp Phe Gly Cys Thr
            340                 345                 350

Trp Met Asn Ser Thr Gly Phe Thr Lys Val Cys Gly Ala Pro Pro Cys
        355                 360                 365
```

|     |     |     |     |     |     |     |     |     |     |     |     |     |     |     |
|---|---|---|---|---|---|---|---|---|---|---|---|---|---|---|
| Val | Ile | Gly | Gly | Val | Gly | Asn | Asn | Thr | Leu | Leu | Cys | Pro | Thr | Asp | Cys |
|     | 370 |     |     |     | 375 |     |     |     |     | 380 |     |     |     |     |
| Phe | Arg | Lys | His | Pro | Glu | Ala | Thr | Tyr | Ser | Arg | Cys | Gly | Ser | Gly | Pro |
| 385 |     |     |     |     | 390 |     |     |     |     | 395 |     |     |     |     | 400 |
| Trp | Ile | Thr | Pro | Arg | Cys | Met | Val | Asp | Tyr | Pro | Tyr | Arg | Leu | Trp | His |
|     |     |     |     | 405 |     |     |     |     | 410 |     |     |     |     | 415 |     |
| Tyr | Pro | Cys | Thr | Ile | Asn | Tyr | Thr | Ile | Phe | Lys | Val | Arg | Met | Tyr | Val |
|     |     |     | 420 |     |     |     |     | 425 |     |     |     |     | 430 |     |     |
| Gly | Gly | Val | Glu | His | Arg | Leu | Glu | Ala | Ala | Cys | Asn | Trp | Thr | Arg | Gly |
|     |     |     | 435 |     |     |     | 440 |     |     |     |     | 445 |     |     |     |
| Glu | Arg | Cys | Asp | Leu |
|     |     |     |     |     |
|     |     |     |     | 450 |

(2) INFORMATION FOR SEQ ID NO:17:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

|     |     |     |     |     |     |     |     |     |     |     |     |     |     |     |     |
|---|---|---|---|---|---|---|---|---|---|---|---|---|---|---|---|
| Met | Leu | Pro | Gly | Leu | Ala | Leu | Leu | Leu | Ala | Ala | Trp | Thr | Ala | Arg |
| 1 |     |     |     | 5 |     |     |     |     | 10 |     |     |     |     | 15 |
| Ala | Leu | Glu | Val | Pro | Ser | Ser | Asn | Ser | Asp | Pro | Tyr | Gln | Val | Arg | Asn |
|     |     |     | 20 |     |     |     |     | 25 |     |     |     |     | 30 |     |     |
| Ser | Ser | Gly | Leu | Tyr | His | Val | Thr | Asn | Asp | Cys | Pro | Asn | Ser | Ser | Ile |
|     |     | 35 |     |     |     |     | 40 |     |     |     |     | 45 |     |     |     |
| Val | Tyr | Glu | Ala | Ala | Asp | Ala | Ile | Leu | His | Thr | Pro | Gly | Cys | Val | Pro |
|     | 50 |     |     |     |     | 55 |     |     |     |     | 60 |     |     |     |     |
| Cys | Val | Arg | Glu | Gly | Asn | Ala | Ser | Arg | Cys | Trp | Val | Ala | Val | Thr | Pro |
| 65 |     |     |     |     | 70 |     |     |     |     | 75 |     |     |     |     | 80 |
| Thr | Val | Ala | Thr | Arg | Asp | Gly | Lys | Leu | Pro | Thr | Thr | Gln | Leu | Arg | Arg |
|     |     |     |     | 85 |     |     |     |     | 90 |     |     |     |     | 95 |     |
| His | Ile | Asp | Leu | Leu | Val | Gly | Ser | Ala | Thr | Leu | Cys | Ser | Ala | Leu | Tyr |
|     |     |     | 100 |     |     |     |     | 105 |     |     |     |     | 110 |     |     |
| Val | Gly | Asp | Gly | His | Thr | Thr | Ala | Gly | Leu | Val | Arg | Leu | Leu | Ser | Pro |
|     |     | 115 |     |     |     |     | 120 |     |     |     |     | 125 |     |     |     |
| Gly | Ala | Lys | Gln | Asn | Ile | Gln | Leu | Ile | Asn | Thr | Asn | Gly | Ser | Trp | His |
|     | 130 |     |     |     |     | 135 |     |     |     |     | 140 |     |     |     |     |
| Ile | Asn | Ser | Thr | Ala | Leu | Asn | Cys | Asn | Glu | Ser | Leu | Asn | Thr | Gly | Trp |
| 145 |     |     |     |     | 150 |     |     |     |     | 155 |     |     |     |     | 160 |
| Leu | Ala | Gly | Leu | Phe | Tyr | His | His | Lys | Phe | Asn | Ser | Ser | Gly | Cys | Pro |
|     |     |     |     | 165 |     |     |     |     | 170 |     |     |     |     | 175 |     |
| Glu | Arg | Leu | Ala | Ser | Cys | Arg | Arg | Leu | Thr | Asp | Phe | Ala | Gln | Gly | Gly |
|     |     |     | 180 |     |     |     |     | 185 |     |     |     |     | 190 |     |     |
| Gly | Pro | Ile | Ser | Tyr | Ala | Asn | Gly | Ser | Gly | Leu | Asp | Glu | Arg | Pro | Tyr |
|     |     |     | 195 |     |     |     |     | 200 |     |     |     |     | 205 |     |     |
| Cys | Trp | His | Tyr | Pro | Pro | Arg | Pro | Cys | Gly | Ile | Val | Pro | Ala | Lys | Ser |
|     | 210 |     |     |     |     | 215 |     |     |     |     | 220 |     |     |     |     |
| Val | Cys | Gly | Pro | Val | Tyr | Cys | Phe | Thr | Pro | Ser | Pro | Val | Val | Val | Gly |
| 225 |     |     |     |     | 230 |     |     |     |     | 235 |     |     |     |     | 240 |
| Thr | Thr | Asp | Arg | Ser | Gly | Ala | Pro | Thr | Tyr | Ser | Trp | Gly | Ala | Asn | Asp |
|     |     |     |     | 245 |     |     |     |     | 250 |     |     |     |     | 255 |     |

```
Thr  Asp  Val  Phe  Val  Leu  Asn  Asn  Thr  Arg  Pro  Pro  Leu  Gly  Asn  Trp
          260                      265                     270

Phe  Gly  Cys  Thr  Trp  Met  Asn  Ser  Thr  Gly  Phe  Thr  Lys  Val  Cys  Gly
          275                      280                     285

Ala  Pro  Pro  Cys  Val  Ile  Gly  Gly  Val  Gly  Asn  Asn  Thr  Leu  Leu  Cys
     290                      295                     300

Pro  Thr  Asp  Cys  Phe  Arg  Lys  His  Pro  Glu  Ala  Thr  Tyr  Ser  Arg  Cys
305                           310                 315                      320

Gly  Ser  Gly  Pro  Trp  Ile  Thr  Pro  Arg  Cys  Met  Val  Asp  Tyr  Pro  Tyr
                    325                      330                      335

Arg  Leu  Trp  His  Tyr  Pro  Cys  Thr  Ile  Asn  Tyr  Thr  Ile  Phe  Lys  Val
               340                      345                      350

Arg  Met  Tyr  Val  Gly  Gly  Val  Glu  His  Arg  Leu  Glu  Ala  Ala  Cys  Asn
          355                      360                      365

Trp  Thr  Arg  Gly  Glu  Arg  Cys  Asp  Leu
     370                      375
```

( 2 ) INFORMATION FOR SEQ ID NO:18:

( i ) SEQUENCE CHARACTERISTICS:
        ( A ) LENGTH: 410 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
Met  Leu  Pro  Gly  Leu  Ala  Leu  Leu  Leu  Leu  Ala  Ala  Trp  Thr  Ala  Arg
1                   5                        10                      15

Ala  Leu  Glu  Val  Pro  Ser  Ser  Asn  Ser  Asp  Pro  Tyr  Gln  Val  Arg  Asn
          20                      25                      30

Ser  Ser  Gly  Leu  Tyr  His  Val  Thr  Asn  Asp  Cys  Pro  Asn  Ser  Ser  Ile
          35                      40                      45

Val  Tyr  Glu  Ala  Ala  Asp  Ala  Ile  Leu  His  Thr  Pro  Gly  Cys  Val  Pro
     50                      55                      60

Cys  Val  Arg  Glu  Gly  Asn  Ala  Ser  Arg  Cys  Trp  Val  Ala  Val  Thr  Pro
65                       70                       75                       80

Thr  Val  Ala  Thr  Arg  Asp  Gly  Lys  Leu  Pro  Thr  Thr  Gln  Leu  Arg  Arg
               85                       90                       95

His  Trp  Thr  Thr  Gln  Asp  Cys  Asn  Cys  Ser  Ile  Tyr  Pro  Gly  His  Ile
               100                      105                      110

Thr  Gly  His  Arg  Met  Ala  Trp  Asp  Met  Met  Met  Asn  Trp  Ser  Pro  Thr
          115                      120                      125

Ala  Ala  Leu  Val  Val  Ala  Gln  Gly  Val  Asp  Ala  Glu  Thr  His  Val  Thr
     130                      135                      140

Gly  Gly  Ser  Ala  Gly  His  Thr  Thr  Ala  Gly  Leu  Val  Arg  Leu  Leu  Ser
145                      150                      155                      160

Pro  Gly  Ala  Lys  Gln  Asn  Ile  Gln  Leu  Ile  Asn  Thr  Asn  Gly  Ser  Trp
                    165                      170                      175

His  Ile  Asn  Ser  Thr  Ala  Leu  Asn  Cys  Asn  Glu  Ser  Leu  Asn  Thr  Gly
               180                      185                      190

Trp  Leu  Ala  Gly  Leu  Phe  Tyr  His  His  Lys  Phe  Asn  Ser  Ser  Gly  Cys
          195                      200                      205

Pro  Glu  Arg  Leu  Ala  Ser  Cys  Arg  Arg  Leu  Thr  Asp  Phe  Ala  Gln  Gly
     210                      215                      220
```

| | | | | | | | | | | | | | | |
|---|---|---|---|---|---|---|---|---|---|---|---|---|---|---|
| Gly 225 | Gly | Pro | Ile | Ser | Tyr 230 | Ala | Asn | Gly | Ser | Gly 235 | Leu | Asp | Glu | Arg Pro 240 |
| Tyr | Cys | Trp | His | Tyr 245 | Pro | Pro | Arg | Pro | Cys 250 | Gly | Ile | Val | Pro | Ala Lys 255 |
| Ser | Val | Cys | Gly 260 | Pro | Val | Tyr | Cys | Phe 265 | Thr | Pro | Ser | Pro | Val 270 | Val Val |
| Gly | Thr | Thr 275 | Asp | Arg | Ser | Gly | Ala 280 | Pro | Thr | Tyr | Ser | Trp 285 | Gly | Ala Asn |
| Asp | Thr 290 | Asp | Val | Phe | Val | Leu 295 | Asn | Asn | Thr | Arg | Pro 300 | Pro | Leu | Gly Asn |
| Trp 305 | Phe | Gly | Cys | Thr | Trp 310 | Met | Asn | Ser | Thr | Gly 315 | Phe | Thr | Lys | Val Cys 320 |
| Gly | Ala | Pro | Pro | Cys 325 | Val | Ile | Gly | Gly | Val 330 | Gly | Asn | Asn | Thr | Leu Leu 335 |
| Cys | Pro | Thr | Asp 340 | Cys | Phe | Arg | Lys | His 345 | Pro | Glu | Ala | Thr | Tyr 350 | Ser Arg |
| Cys | Gly | Ser 355 | Gly | Pro | Trp | Ile | Thr 360 | Pro | Arg | Cys | Met | Val 365 | Asp | Tyr Pro |
| Tyr | Arg 370 | Leu | Trp | His | Tyr | Pro 375 | Cys | Thr | Ile | Asn | Tyr 380 | Thr | Ile | Phe Lys |
| Val 385 | Arg | Met | Tyr | Val | Gly 390 | Gly | Val | Glu | His | Arg 395 | Leu | Glu | Ala | Ala Cys 400 |
| Asn | Trp | Thr | Arg | Gly 405 | Glu | Arg | Cys | Asp | Leu 410 | | | | | |

( 2 ) INFORMATION FOR SEQ ID NO:19:

( i ) SEQUENCE CHARACTERISTICS:
        ( A ) LENGTH: 417 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

| | | | | | | | | | | | | | | |
|---|---|---|---|---|---|---|---|---|---|---|---|---|---|---|
| Met 1 | Leu | Pro | Gly | Leu 5 | Ala | Leu | Leu | Leu | Ala 10 | Ala | Trp | Thr | Ala 15 | Arg |
| Ala | Leu | Glu | Val 20 | Pro | Ser | Ser | Asn | Ser 25 | Asp | Pro | Tyr | Gln | Val 30 | Arg Asn |
| Ser | Ser | Gly 35 | Leu | Tyr | His | Val | Thr 40 | Asn | Asp | Cys | Pro | Asn 45 | Ser | Ser Ile |
| Val | Tyr 50 | Glu | Ala | Ala | Asp | Ala 55 | Ile | Leu | His | Thr | Pro 60 | Gly | Cys | Val Pro |
| Cys 65 | Val | Arg | Glu | Gly | Asn 70 | Ala | Ser | Arg | Cys | Trp 75 | Val | Ala | Val | Thr Pro 80 |
| Thr | Val | Ala | Thr | Arg 85 | Asp | Gly | Lys | Leu | Pro 90 | Thr | Thr | Gln | Leu | Arg Arg 95 |
| His | Trp | Thr | Thr 100 | Gln | Asp | Cys | Asn | Cys 105 | Ser | Ile | Tyr | Pro | Gly 110 | His Ile |
| Thr | Gly | His 115 | Arg | Met | Ala | Trp | Asp 120 | Met | Met | Met | Asn | Trp 125 | Ser | Met Val |
| Gly | Asn 130 | Trp | Ala | Lys | Val | Leu 135 | Val | Val | Leu | Leu | Leu 140 | Phe | Ala | Gly Val |
| Asp 145 | Ala | Glu | Thr | His | Val 150 | Thr | Gly | Gly | Ser | Ala 155 | Gly | His | Thr | Thr Ala 160 |

```
Gly  Leu  Val  Arg  Leu  Leu  Ser  Pro  Gly  Ala  Lys  Gln  Asn  Ile  Gln  Leu
               165                 170                     175

Ile  Asn  Thr  Asn  Gly  Ser  Trp  His  Ile  Asn  Ser  Thr  Ala  Leu  Asn  Cys
                    180                      185                 190

Asn  Glu  Ser  Leu  Asn  Thr  Gly  Trp  Leu  Ala  Gly  Leu  Phe  Tyr  His  His
          195                      200                      205

Lys  Phe  Asn  Ser  Ser  Gly  Cys  Pro  Glu  Arg  Leu  Ala  Ser  Cys  Arg  Arg
     210                      215                 220

Leu  Thr  Asp  Phe  Ala  Gln  Gly  Gly  Pro  Ile  Ser  Tyr  Ala  Asn  Gly
225                      230                 235                           240

Ser  Gly  Leu  Asp  Glu  Arg  Pro  Tyr  Cys  Trp  His  Tyr  Pro  Pro  Arg  Pro
               245                      250                           255

Cys  Gly  Ile  Val  Pro  Ala  Lys  Ser  Val  Cys  Gly  Pro  Val  Tyr  Cys  Phe
               260                 265                      270

Thr  Pro  Ser  Pro  Val  Val  Val  Gly  Thr  Thr  Asp  Arg  Ser  Gly  Ala  Pro
          275                      280                      285

Thr  Tyr  Ser  Trp  Gly  Ala  Asn  Asp  Thr  Asp  Val  Phe  Val  Leu  Asn  Asn
          290                 295                      300

Thr  Arg  Pro  Pro  Leu  Gly  Asn  Trp  Phe  Gly  Cys  Thr  Trp  Met  Asn  Ser
305                      310                      315                      320

Thr  Gly  Phe  Thr  Lys  Val  Cys  Gly  Ala  Pro  Pro  Cys  Val  Ile  Gly  Gly
                    325                      330                      335

Val  Gly  Asn  Asn  Thr  Leu  Leu  Cys  Pro  Thr  Asp  Cys  Phe  Arg  Lys  His
               340                      345                      350

Pro  Glu  Ala  Thr  Tyr  Ser  Arg  Cys  Gly  Ser  Gly  Pro  Trp  Ile  Thr  Pro
               355                      360                      365

Arg  Cys  Met  Val  Asp  Tyr  Pro  Tyr  Arg  Leu  Trp  His  Tyr  Pro  Cys  Thr
370                           375                      380

Ile  Asn  Tyr  Thr  Ile  Phe  Lys  Val  Arg  Met  Tyr  Val  Gly  Gly  Val  Glu
385                      390                      395                      400

His  Arg  Leu  Glu  Ala  Ala  Cys  Asn  Trp  Thr  Arg  Gly  Glu  Arg  Cys  Asp
                         405                           410                      415

Leu
```

(2) INFORMATION FOR SEQ ID NO:20:

( i ) SEQUENCE CHARACTERISTICS:
        ( A ) LENGTH: 447 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

```
Met  Leu  Pro  Gly  Leu  Ala  Leu  Leu  Leu  Ala  Ala  Trp  Thr  Ala  Arg
1                5                           10                      15

Ala  Leu  Glu  Val  Pro  Ser  Ser  Asn  Ser  Asp  Pro  Tyr  Gln  Val  Arg  Asn
               20                      25                      30

Ser  Ser  Gly  Leu  Tyr  His  Val  Thr  Asn  Asp  Cys  Pro  Asn  Ser  Ser  Ile
               35                      40                      45

Val  Tyr  Glu  Ala  Ala  Asp  Ala  Ile  Leu  His  Thr  Pro  Gly  Cys  Val  Pro
          50                      55                      60

Cys  Val  Arg  Glu  Gly  Asn  Ala  Ser  Arg  Cys  Trp  Val  Ala  Val  Thr  Pro
65                       70                      75                       80

Thr  Val  Ala  Thr  Arg  Asp  Gly  Lys  Leu  Pro  Thr  Thr  Gln  Leu  Arg  Arg
               85                      90                      95
```

| | | | | | | | | | | | | | | |
|---|---|---|---|---|---|---|---|---|---|---|---|---|---|---|
| His | Ile | Asp | Leu | Leu | Val | Gly | Ser | Ala | Thr | Leu | Cys | Ser | Ala | Leu | Tyr |
| | | | 100 | | | | | 105 | | | | | 110 | | |
| Val | Gly | Asp | Leu | Cys | Gly | Ser | Val | Phe | Leu | Val | Gly | Gln | Leu | Phe | Thr |
| | | | 115 | | | | 120 | | | | | 125 | | | |
| Phe | Ser | Pro | Arg | Arg | His | Trp | Thr | Thr | Gln | Asp | Cys | Asn | Cys | Ser | Ile |
| | | 130 | | | | | 135 | | | | 140 | | | | |
| Tyr | Pro | Gly | His | Ile | Thr | Gly | His | Arg | Met | Ala | Trp | Asp | Met | Met | Met |
| 145 | | | | | 150 | | | | | 155 | | | | | 160 |
| Asn | Trp | Ser | Pro | Thr | Ala | Ala | Leu | Val | Val | Ala | Gln | Gly | Val | Asp | Ala |
| | | | | 165 | | | | | 170 | | | | | 175 | |
| Glu | Thr | His | Val | Thr | Gly | Gly | Ser | Ala | Gly | His | Thr | Thr | Ala | Gly | Leu |
| | | | 180 | | | | | 185 | | | | | 190 | | |
| Val | Arg | Leu | Leu | Ser | Pro | Gly | Ala | Lys | Gln | Asn | Ile | Gln | Leu | Ile | Asn |
| | | 195 | | | | | 200 | | | | | 205 | | | |
| Thr | Asn | Gly | Ser | Trp | His | Ile | Asn | Ser | Thr | Ala | Leu | Asn | Cys | Asn | Glu |
| | 210 | | | | | 215 | | | | | 220 | | | | |
| Ser | Leu | Asn | Thr | Gly | Trp | Leu | Ala | Gly | Leu | Phe | Tyr | His | His | Lys | Phe |
| 225 | | | | | 230 | | | | 235 | | | | | | 240 |
| Asn | Ser | Ser | Gly | Cys | Pro | Glu | Arg | Leu | Ala | Ser | Cys | Arg | Arg | Leu | Thr |
| | | | | 245 | | | | | 250 | | | | | 255 | |
| Asp | Phe | Ala | Gln | Gly | Gly | Gly | Pro | Ile | Ser | Tyr | Ala | Asn | Gly | Ser | Gly |
| | | | 260 | | | | | 265 | | | | | 270 | | |
| Leu | Asp | Glu | Arg | Pro | Tyr | Cys | Trp | His | Tyr | Pro | Pro | Arg | Pro | Cys | Gly |
| | | | 275 | | | | | 280 | | | | | 285 | | |
| Ile | Val | Pro | Ala | Lys | Ser | Val | Cys | Gly | Pro | Val | Tyr | Cys | Phe | Thr | Pro |
| | 290 | | | | | 295 | | | | | 300 | | | | |
| Ser | Pro | Val | Val | Val | Gly | Thr | Thr | Asp | Arg | Ser | Gly | Ala | Pro | Thr | Tyr |
| 305 | | | | | 310 | | | | | 315 | | | | | 320 |
| Ser | Trp | Gly | Ala | Asn | Asp | Thr | Asp | Val | Phe | Val | Leu | Asn | Asn | Thr | Arg |
| | | | | 325 | | | | | 330 | | | | | 335 | |
| Pro | Pro | Leu | Gly | Asn | Trp | Phe | Gly | Cys | Thr | Trp | Met | Asn | Ser | Thr | Gly |
| | | | 340 | | | | | 345 | | | | | 350 | | |
| Phe | Thr | Lys | Val | Cys | Gly | Ala | Pro | Pro | Cys | Val | Ile | Gly | Gly | Val | Gly |
| | | 355 | | | | | 360 | | | | | 365 | | | |
| Asn | Asn | Thr | Leu | Leu | Cys | Pro | Thr | Asp | Cys | Phe | Arg | Lys | His | Pro | Glu |
| | 370 | | | | | 375 | | | | | 380 | | | | |
| Ala | Thr | Tyr | Ser | Arg | Cys | Gly | Ser | Gly | Pro | Trp | Ile | Thr | Pro | Arg | Cys |
| 385 | | | | | 390 | | | | | 395 | | | | | 400 |
| Met | Val | Asp | Tyr | Pro | Tyr | Arg | Leu | Trp | His | Tyr | Pro | Cys | Thr | Ile | Asn |
| | | | | 405 | | | | | 410 | | | | | 415 | |
| Tyr | Thr | Ile | Phe | Lys | Val | Arg | Met | Tyr | Val | Gly | Gly | Val | Glu | His | Arg |
| | | | 420 | | | | | 425 | | | | | 430 | | |
| Leu | Glu | Ala | Ala | Cys | Asn | Trp | Thr | Arg | Gly | Glu | Arg | Cys | Asp | Leu | |
| | | 435 | | | | | 440 | | | | | 445 | | | |

( 2 ) INFORMATION FOR SEQ ID NO:21:

( i ) SEQUENCE CHARACTERISTICS:
        ( A ) LENGTH: 441 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

| | | | | | | | | | | | | | | |
|---|---|---|---|---|---|---|---|---|---|---|---|---|---|---|
| Met | Leu | Pro | Gly | Leu | Ala | Leu | Leu | Leu | Ala | Ala | Trp | Thr | Ala | Arg |
| 1 | | | | 5 | | | | 10 | | | | | 15 | |
| Ala | Leu | Glu | Val | Pro | Ser | Ser | Asn | Ser | Asp | Pro | Tyr | Gln | Val | Arg | Asn |
| | | | 20 | | | | | 25 | | | | | 30 | | |
| Ser | Ser | Gly | Leu | Tyr | His | Val | Thr | Asn | Asp | Cys | Pro | Asn | Ser | Ser | Ile |
| | | 35 | | | | | 40 | | | | | 45 | | | |
| Val | Tyr | Glu | Ala | Ala | Asp | Ala | Ile | Leu | His | Thr | Pro | Gly | Cys | Val | Pro |
| | 50 | | | | 55 | | | | | 60 | | | | | |
| Cys | Val | Arg | Glu | Gly | Asn | Ala | Ser | Arg | Cys | Trp | Val | Ala | Val | Thr | Pro |
| 65 | | | | | 70 | | | | 75 | | | | | | 80 |
| Thr | Val | Ala | Thr | Arg | Asp | Gly | Lys | Leu | Pro | Thr | Thr | Gln | Leu | Arg | Arg |
| | | | | 85 | | | | | 90 | | | | | 95 | |
| His | Trp | Thr | Thr | Gln | Asp | Cys | Asn | Cys | Ser | Ile | Tyr | Pro | Gly | His | Ile |
| | | | 100 | | | | | 105 | | | | | 110 | | |
| Thr | Gly | His | Arg | Met | Ala | Trp | Asp | Met | Met | Met | Asn | Trp | Ser | Ile | Pro |
| | | 115 | | | | | 120 | | | | | 125 | | | |
| Gln | Ala | Ile | Leu | Asp | Met | Ile | Ala | Gly | Ala | His | Trp | Gly | Val | Leu | Ala |
| | 130 | | | | 135 | | | | | 140 | | | | | |
| Gly | Ile | Ala | Tyr | Phe | Ser | Met | Val | Gly | Asn | Trp | Ala | Lys | Val | Leu | Val |
| 145 | | | | | 150 | | | | | 155 | | | | | 160 |
| Val | Leu | Leu | Leu | Phe | Ala | Gly | Val | Asp | Ala | Glu | Thr | His | Val | Thr | Gly |
| | | | | 165 | | | | | 170 | | | | | 175 | |
| Gly | Ser | Ala | Gly | His | Thr | Thr | Ala | Gly | Leu | Val | Arg | Leu | Leu | Ser | Pro |
| | | | 180 | | | | | 185 | | | | | 190 | | |
| Gly | Ala | Lys | Gln | Asn | Ile | Gln | Leu | Ile | Asn | Thr | Asn | Gly | Ser | Trp | His |
| | | 195 | | | | | 200 | | | | | 205 | | | |
| Ile | Asn | Ser | Thr | Ala | Leu | Asn | Cys | Asn | Glu | Ser | Leu | Asn | Thr | Gly | Trp |
| | 210 | | | | 215 | | | | | 220 | | | | | |
| Leu | Ala | Gly | Leu | Phe | Tyr | His | His | Lys | Phe | Asn | Ser | Ser | Gly | Cys | Pro |
| 225 | | | | | 230 | | | | | 235 | | | | | 240 |
| Glu | Arg | Leu | Ala | Ser | Cys | Arg | Arg | Leu | Thr | Asp | Phe | Ala | Gln | Gly | Gly |
| | | | | 245 | | | | | 250 | | | | | 255 | |
| Gly | Pro | Ile | Ser | Tyr | Ala | Asn | Gly | Ser | Gly | Leu | Asp | Glu | Arg | Pro | Tyr |
| | | | 260 | | | | | 265 | | | | | 270 | | |
| Cys | Trp | His | Tyr | Pro | Pro | Arg | Pro | Cys | Gly | Ile | Val | Pro | Ala | Lys | Ser |
| | | 275 | | | | | 280 | | | | | 285 | | | |
| Val | Cys | Gly | Pro | Val | Tyr | Cys | Phe | Thr | Pro | Ser | Pro | Val | Val | Val | Gly |
| | 290 | | | | 295 | | | | | 300 | | | | | |
| Thr | Thr | Asp | Arg | Ser | Gly | Ala | Pro | Thr | Tyr | Ser | Trp | Gly | Ala | Asn | Asp |
| 305 | | | | | 310 | | | | | 315 | | | | | 320 |
| Thr | Asp | Val | Phe | Val | Leu | Asn | Asn | Thr | Arg | Pro | Pro | Leu | Gly | Asn | Trp |
| | | | | 325 | | | | | 330 | | | | | 335 | |
| Phe | Gly | Cys | Thr | Trp | Met | Asn | Ser | Thr | Gly | Phe | Thr | Lys | Val | Cys | Gly |
| | | | 340 | | | | | 345 | | | | | 350 | | |
| Ala | Pro | Pro | Cys | Val | Ile | Gly | Gly | Val | Gly | Asn | Asn | Thr | Leu | Leu | Cys |
| | | 355 | | | | | 360 | | | | | 365 | | | |
| Pro | Thr | Asp | Cys | Phe | Arg | Lys | His | Pro | Glu | Ala | Thr | Tyr | Ser | Arg | Cys |
| | 370 | | | | 375 | | | | | 380 | | | | | |
| Gly | Ser | Gly | Pro | Trp | Ile | Thr | Pro | Arg | Cys | Met | Val | Asp | Tyr | Pro | Tyr |
| 385 | | | | | 390 | | | | | 395 | | | | | 400 |
| Arg | Leu | Trp | His | Tyr | Pro | Cys | Thr | Ile | Asn | Tyr | Thr | Ile | Phe | Lys | Val |
| | | | | 405 | | | | | 410 | | | | | 415 | |
| Arg | Met | Tyr | Val | Gly | Gly | Val | Glu | His | Arg | Leu | Glu | Ala | Ala | Cys | Asn |
| | | | 420 | | | | | 425 | | | | | 430 | | |

-continued

```
        Trp  Thr  Arg  Gly  Glu  Arg  Cys  Asp  Leu
                  435                      440
```

( 2 ) INFORMATION FOR SEQ ID NO:22:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

```
   Leu  Leu  Arg  Ile  Pro  Gln  Ala  Ile  Leu  Asp  Met  Ile  Ala  Gly  Ala  His
   1                   5                        10                       15

Trp  Gly  Val  Leu  Ala  Gly  Ile  Ala  Tyr  Phe  Ser  Met  Val  Gly  Asn  Trp
                  20                       25                       30

Ala  Lys  Val  Leu  Val  Val  Leu  Leu  Phe  Ala
                  35                       40
```